(12) United States Patent
Cashman et al.

(10) Patent No.: US 10,759,837 B2
(45) Date of Patent: *Sep. 1, 2020

(54) ANTI-AMYLOID BETA ANTIBODIES BINDING TO A CYCLIC AMYLOID BETA PEPTIDE

(71) Applicant: The University of British Columbia, Vancouver (CA)

(72) Inventors: Neil R. Cashman, Vancouver (CA); Steven S. Plotkin, Vancouver (CA)

(73) Assignee: The University of British Columbia, Vancouver (CA)

(*) Notice: Subject to any disclaimer, the term of this patent is extended or adjusted under 35 U.S.C. 154(b) by 0 days.

This patent is subject to a terminal disclaimer.

(21) Appl. No.: 15/774,778

(22) PCT Filed: Nov. 9, 2016

(86) PCT No.: PCT/CA2016/051305
§ 371 (c)(1),
(2) Date: May 9, 2018

(87) PCT Pub. No.: WO2017/079835
PCT Pub. Date: May 18, 2017

(65) Prior Publication Data
US 2018/0346535 A1    Dec. 6, 2018

Related U.S. Application Data

(60) Provisional application No. 62/253,044, filed on Nov. 9, 2015, provisional application No. 62/289,893, filed
(Continued)

(51) Int. Cl.
*A61K 39/395* (2006.01)
*A61K 39/00* (2006.01)
(Continued)

(52) U.S. Cl.
CPC ...... *C07K 14/4711* (2013.01); *A61K 39/0008* (2013.01); *A61K 47/643* (2017.08); *A61K 47/646* (2017.08); *A61K 51/1018* (2013.01); *A61P 25/28* (2018.01); *C07K 5/1021* (2013.01); *C07K 5/1024* (2013.01); *C07K 7/64* (2013.01); *C07K 16/18* (2013.01); *G01N 33/6896* (2013.01); *A61K 38/00* (2013.01); *A61K 38/05* (2013.01); *A61K 38/07* (2013.01); *A61K 38/08* (2013.01); *A61K 38/12* (2013.01); *A61K 39/00* (2013.01); *A61K 39/0007* (2013.01); *A61K 39/385* (2013.01); *A61K 39/39* (2013.01); *A61K 39/395* (2013.01); *A61K 39/3955* (2013.01); *A61K 39/39533* (2013.01); *A61K 45/05* (2013.01); *A61K 45/06* (2013.01); *A61K 47/6803* (2017.08); *A61K 47/6921* (2017.08); *A61K 49/1818* (2013.01); *A61K 51/088* (2013.01); *A61K 51/10* (2013.01); *A61K 2039/505* (2013.01); *A61K 2039/55505* (2013.01); *A61K 2039/6081* (2013.01); *A61K 2300/00* (2013.01); *A61L 27/227* (2013.01); *A61L 27/34* (2013.01); *A61L 29/085* (2013.01);
(Continued)

(58) Field of Classification Search
CPC .. A61K 38/00; A61K 2039/505; A61K 45/06; A61K 38/12; A61K 39/3955; A61K 38/07; A61K 38/08; A61K 39/007; A61K 39/395; A61K 39/39533; A61K 47/6921; A61K 49/1818; A61K 49/1866; A61K 38/05; A61K 39/00; A61K 39/39; A61K 45/05; A61K 47/6803; A61K 51/10; C07K 16/18; C07K 14/4711; C07K 14/47; C07K 7/08; C07K 7/06; C07K 2317/24; C07K 2317/34; C07K 2317/92; C07K 2317/565; C07K 2317/76; C07K 2317/56; C07K 2317/55; C07K 2317/20; C07K 2317/524; C07K 2317/526; C07K 2317/54; C07K 2317/624; C07K 2317/70; C07K 2317/94; C07K 2317/30; C07K 2317/31; C07K 2317/33; C07K 2317/569; C07K 2317/626; C07K 16/00; G01N 33/6896; G01N 2800/2821; G01N 2800/28; G01N 2800/387; G01N 2333/4709; A61L 27/227; A61L 27/34; A61L 29/085; A61L 29/16; A61L 31/10; A61L 31/16; A61P 25/28

See application file for complete search history.

(56) References Cited

U.S. PATENT DOCUMENTS 5,283,185 A   2/1994 Epand et al.
5,593,846 A   1/1997 Schenk et al.
(Continued)

FOREIGN PATENT DOCUMENTS

EP    2377860 A1   10/2011
WO   88/09336 A1    5/1988
(Continued)

OTHER PUBLICATIONS

Rudikoff et al., Proc Natl Acad Sci USA 1982; 79:1979-1983.*
(Continued)

*Primary Examiner* — Chang-Yu Wang
(74) *Attorney, Agent, or Firm* — Carmela De Luca; Bereskin & Parr LLP

(57) ABSTRACT

The disclosure pertains to epitopes identified in A-beta including conformational epitopes, antibodies thereto and methods of making and using immunogens and antibodies specific thereto.

9 Claims, 31 Drawing Sheets

Specification includes a Sequence Listing.

Related U.S. Application Data on Feb. 1, 2016, provisional application No. 62/365,634, filed on Jul. 22, 2016, provisional application No. 62/393,615, filed on Sep. 12, 2016.

(51) Int. Cl.

| | | |
|---|---|---|
| *A61K 49/00* | (2006.01) | |
| *A61K 49/16* | (2006.01) | |
| *C07K 16/00* | (2006.01) | |
| *C12P 21/08* | (2006.01) | |
| *G01N 33/53* | (2006.01) | |
| *C07K 14/47* | (2006.01) | |
| *C07K 16/18* | (2006.01) | |
| *C07K 5/117* | (2006.01) | |
| *C07K 5/113* | (2006.01) | |
| *A61K 47/64* | (2017.01) | |
| *A61P 25/28* | (2006.01) | |
| *A61K 51/10* | (2006.01) | |
| *C07K 7/64* | (2006.01) | |
| *G01N 33/68* | (2006.01) | |
| *A61K 39/385* | (2006.01) | |
| *A61K 51/08* | (2006.01) | |
| *A61K 45/06* | (2006.01) | |
| *A61K 39/39* | (2006.01) | |
| *A61K 38/05* | (2006.01) | |
| *A61K 49/18* | (2006.01) | |
| *A61K 38/12* | (2006.01) | |
| *A61K 47/68* | (2017.01) | |
| *A61K 38/07* | (2006.01) | |
| *A61K 47/69* | (2017.01) | |
| *A61K 38/00* | (2006.01) | |
| *A61K 38/08* | (2019.01) | |
| *A61K 45/00* | (2006.01) | |
| *A61L 27/34* | (2006.01) | |
| *A61L 29/16* | (2006.01) | |
| *A61L 31/10* | (2006.01) | |
| *A61L 29/08* | (2006.01) | |
| *A61L 27/22* | (2006.01) | |
| *A61L 31/16* | (2006.01) | |
| *C07K 7/08* | (2006.01) | |
| *C07K 7/06* | (2006.01) | |
| *C07K 5/103* | (2006.01) | |
| *C07K 14/435* | (2006.01) | |
| *G01N 33/50* | (2006.01) | |

(52) U.S. Cl.
CPC ............ *A61L 29/16* (2013.01); *A61L 31/10* (2013.01); *A61L 31/16* (2013.01); *C07K 5/101* (2013.01); *C07K 7/06* (2013.01); *C07K 7/08* (2013.01); *C07K 14/435* (2013.01); *C07K 16/00* (2013.01); *C07K 2317/20* (2013.01); *C07K 2317/24* (2013.01); *C07K 2317/30* (2013.01); *C07K 2317/33* (2013.01); *C07K 2317/34* (2013.01); *C07K 2317/524* (2013.01); *C07K 2317/526* (2013.01); *C07K 2317/54* (2013.01); *C07K 2317/55* (2013.01); *C07K 2317/56* (2013.01); *C07K 2317/565* (2013.01); *C07K 2317/569* (2013.01); *C07K 2317/624* (2013.01); *C07K 2317/626* (2013.01); *C07K 2317/70* (2013.01); *C07K 2317/76* (2013.01); *C07K 2317/92* (2013.01); *C07K 2317/94* (2013.01); *C07K 2319/00* (2013.01); *G01N 33/5058* (2013.01); *G01N 2333/4709* (2013.01); *G01N 2800/28* (2013.01); *G01N 2800/2821* (2013.01); *G01N 2800/387* (2013.01)

(56) References Cited

U.S. PATENT DOCUMENTS

| | | | |
|---|---|---|---|
| 5,770,429 A | 6/1998 | Lonberg et al. | |
| 5,814,014 A | 9/1998 | Elsberry et al. | |
| 6,043,283 A * | 3/2000 | Giulian | A61K 51/0406 514/617 |
| 6,071,493 A * | 6/2000 | Giulian | A61K 51/0406 424/9.1 |
| 6,114,598 A | 9/2000 | Kucherlapati et al. | |
| 6,150,584 A | 11/2000 | Kucherlapati et al. | |
| 6,451,544 B2 * | 9/2002 | Giulian | A61K 51/0406 435/7.2 |
| 6,475,742 B2 * | 11/2002 | Giulian | A61K 51/0406 435/7.1 |
| 6,475,745 B1 * | 11/2002 | Giulian | A61K 51/0406 435/7.2 |
| 6,875,434 B1 * | 4/2005 | Schenk | A61K 38/1709 424/184.1 |
| 6,890,535 B1 * | 5/2005 | Schenk | A61K 38/1709 424/184.1 |
| 6,913,745 B1 * | 7/2005 | Schenk | A61K 38/1709 424/130.1 |
| 6,923,964 B1 * | 8/2005 | Schenk | A61K 38/1709 424/185.1 |
| 7,012,061 B1 | 3/2006 | Reiss et al. | |
| 7,179,892 B2 * | 2/2007 | Basi | C07K 16/18 424/133.1 |
| 7,189,819 B2 * | 3/2007 | Basi | A61K 38/1709 530/387.3 |
| 7,256,273 B2 * | 8/2007 | Basi | C07K 16/18 530/387.3 |
| 7,288,523 B2 | 10/2007 | Nordstedt et al. | |
| 7,575,880 B1 * | 8/2009 | Schenk | A61K 39/395 435/7.21 |
| 7,582,733 B2 * | 9/2009 | Basi | A61K 38/1709 530/387.1 |
| 7,588,766 B1 * | 9/2009 | Schenk | A61K 38/1709 424/192.1 |
| 7,625,560 B2 * | 12/2009 | Basi | C07K 16/18 424/145.1 |
| 7,700,751 B2 * | 4/2010 | Basi | C07K 16/18 530/387.1 |
| 7,790,856 B2 * | 9/2010 | Schenk | C07K 16/18 424/130.1 |
| 7,871,615 B2 * | 1/2011 | Basi | C07K 16/18 424/133.1 |
| 7,893,214 B2 * | 2/2011 | Schenk | A61K 47/646 424/133.1 |
| 7,932,048 B2 | 4/2011 | Mendez | |
| 7,964,192 B1 * | 6/2011 | Schenk | A61K 38/1709 424/133.1 |
| 7,977,316 B2 * | 7/2011 | Schenk | A61K 39/0007 514/21.2 |
| 8,003,097 B2 * | 8/2011 | Schroeter | C07K 16/18 424/133.1 |
| 8,034,339 B2 * | 10/2011 | Schenk | A61K 47/646 424/133.1 |
| 8,124,081 B2 * | 2/2012 | Schenk | A61K 39/0007 424/133.1 |
| 8,128,928 B2 * | 3/2012 | Basi | C07K 16/18 424/133.1 |
| 8,216,577 B2 | 7/2012 | Bardoff et al. | |
| 8,613,920 B2 * | 12/2013 | Lieberburg | C07K 16/18 424/133.1 |
| 8,623,365 B2 | 1/2014 | Davies | |
| 8,784,810 B2 * | 7/2014 | Lieberburg | C07K 16/18 424/133.1 |
| 8,916,165 B2 * | 12/2014 | Basi | C07K 16/18 424/133.1 |
| 9,051,363 B2 * | 6/2015 | Basi | A61K 47/646 |
| 9,067,981 B1 * | 6/2015 | Basi | C07K 16/18 |
| 9,084,832 B2 | 7/2015 | Nordstrom et al. | |
| 9,221,812 B2 | 12/2015 | Kroth et al. | |
| 9,334,303 B2 | 5/2016 | Mediannikov et al. | |

(56) References Cited

U.S. PATENT DOCUMENTS

| | | | |
|---|---|---|---|
| 9,493,496 B2 | 11/2016 | Geng et al. | |
| 9,535,076 B2 | 1/2017 | Kayed et al. | |
| 9,644,025 B2* | 5/2017 | Black | C07K 16/18 |
| 2001/0016326 A1* | 8/2001 | Giulian | A61K 51/0406 |
| | | | 435/7.2 |
| 2001/0016327 A1* | 8/2001 | Giulian | A61K 51/0406 |
| | | | 435/7.2 |
| 2003/0091577 A1* | 5/2003 | Gilbert | A61K 39/092 |
| | | | 424/184.1 |
| 2005/0267029 A1* | 12/2005 | Ancsin | A61K 38/1709 |
| | | | 435/29 |
| 2007/0110750 A1 | 5/2007 | Glabe et al. | |
| 2008/0107649 A1* | 5/2008 | Zurbriggen | C07K 14/4711 |
| | | | 424/133.1 |
| 2008/0299111 A1 | 12/2008 | Delacourte | |
| 2009/0246191 A1 | 10/2009 | O'Nuallain et al. | |
| 2011/0171243 A1 | 7/2011 | Mandler et al. | |
| 2012/0047601 A1* | 2/2012 | Scheller | A01H 5/10 |
| | | | 800/278 |
| 2013/0136747 A1 | 5/2013 | Bardroff et al. | |
| 2013/0252901 A1* | 9/2013 | Mediannikov | C07K 5/1019 |
| | | | 514/17.8 |
| 2015/0105344 A1 | 4/2015 | Geng et al. | |
| 2015/0322143 A1 | 11/2015 | Kayed | |
| 2017/0021020 A1 | 1/2017 | Bollyky et al. | |
| 2018/0125920 A1* | 5/2018 | Cashman | C07K 5/0808 |
| 2018/0319856 A1* | 11/2018 | Cashman | C07K 16/18 |
| 2018/0330045 A1* | 11/2018 | Plotkin | G16B 15/20 |
| 2018/0346535 A1* | 12/2018 | Cashman | C07K 16/18 |
| 2019/0151401 A1* | 5/2019 | Cashman | A61K 38/07 |

FOREIGN PATENT DOCUMENTS

| | | |
|---|---|---|
| WO | 90/14387 A1 | 5/1990 |
| WO | 91/17271 A1 | 5/1991 |
| WO | 92/01047 A1 | 7/1991 |
| WO | 96/14831 A1 | 11/1994 |
| WO | 95/17211 A1 | 12/1994 |
| WO | 1995/006477 A1 | 3/1995 |
| WO | 95/34323 A2 | 6/1995 |
| WO | 96/06627 A1 | 7/1995 |
| WO | 2001062801 A2 | 8/2001 |
| WO | 2004/058239 A1 | 7/2003 |
| WO | 2003/070760 A2 | 8/2003 |
| WO | 2004/029629 A1 | 4/2004 |
| WO | 2004/071408 A2 | 8/2004 |
| WO | 2006/066089 A1 | 12/2005 |
| WO | 2006/095041 A1 | 9/2006 |
| WO | 2006125324 A1 | 11/2006 |
| WO | 2007/059000 A2 | 5/2007 |
| WO | 2007/068429 A1 | 6/2007 |
| WO | 2008/060364 A2 | 5/2008 |
| WO | 2008/088983 A1 | 7/2008 |
| WO | 2008/156621 A1 | 12/2008 |
| WO | 2008/156622 A1 | 12/2008 |
| WO | 2009086539 A2 | 12/2008 |
| WO | 2009/048537 A2 | 4/2009 |
| WO | 2009/048538 A2 | 4/2009 |
| WO | 2009/052439 A2 | 4/2009 |
| WO | 2009/065054 A2 | 5/2009 |
| WO | 2009/149487 A2 | 12/2009 |
| WO | 2009149487 A2 | 12/2009 |
| WO | 2010/002251 A1 | 1/2010 |
| WO | 2010/040209 A1 | 4/2010 |
| WO | 2010119704 A1 | 10/2010 |
| WO | 2010/128139 A1 | 11/2010 |
| WO | 2011016238 A1 | 2/2011 |
| WO | 2011/033046 A1 | 3/2011 |
| WO | 2011/106885 A1 | 9/2011 |
| WO | 2011104696 A1 | 9/2011 |
| WO | 2012/104824 A1 | 8/2012 |
| WO | 2002/096937 A2 | 12/2012 |
| WO | 2013/020723 | 2/2013 |
| WO | 2013/071267 A1 | 5/2013 |
| WO | 2014/031697 A3 | 2/2014 |
| WO | 2014/161875 A1 | 4/2014 |
| WO | 2015/017900 A1 | 2/2015 |
| WO | 2015031698 A1 | 3/2015 |
| WO | 2015/113169 A1 | 8/2015 |
| WO | 2017/079831 A1 | 5/2017 |
| WO | 2017/079832 A1 | 5/2017 |
| WO | 2017/079833 A1 | 5/2017 |
| WO | 2017/079834 A1 | 5/2017 |
| WO | 2017/079836 A1 | 5/2017 |
| WO | 2018/014126 A1 | 1/2018 |

OTHER PUBLICATIONS

MacCallunn et al., J. Mol. Biol., 1996; 262: 732-745.*
Pascalis et al., The Journal of Immunology, 2002; 169: 3076-3084.*
Casset et al., BBRC, 2003; 307:198-205.*
Vajdos et al., J. Mol. Med., 2002; 320: 415-428.*
Holm et al., Mol. Immunol., 2007; 44: 1075-1084.*
Chen et al., J. Mol. Bio., 1999; 293: 865-881.*
Wu et al., J. Mol. Biol.,1999; 294: 151-162.*
Burgess et al., J of Cell Bio. 1990, 111:2129-2138.*
Bowie et al., Science, 1990, 247:1306-1310.*
Pawson et al., Science, 2003, 300:445-452.*
Alaoui-Ismaili et al., Cytokine Growth Factor Rev. 2009; 20:501-507.*
Guo et al., PNAS 2004; 101:9205-9210.*
Krafft, Grant et al. ACU-193: A candidate therapeutic antibody that selectively targets soluble beta-amyloid oligomers, Alzheimer's & Dementia: The Journal of the Alzheimer's Association, Jan. 1, 2013, pp. P326-P326.
Hillen, Heinz et al. Generation and Therapeutic Efficacy of Highly Oligomer-Specific beta-Amyloid Antibodies, the Journal of Neuroscience, Society for Neuroscience, US, vol. 30, No. 31, Aug. 4, 2010, pp. 10369-10379.
Hoogerhout, Peter et al. A Cyclic Undecamer Peptide Mimics a Turn in Folded Alzheimer Amyloid β and Elicits Antibodies against Oligomeric and Fibrillar Amyloid and Plaques, Plos One, vol. 6, No. 4, Jan. 1, 2011, pp. e19110-e19110.
Arai, Tadamasa et al. A Cyclic KLVFF-Derived Peptide Aggregation Inhibitor Induces the Formation of Less-Toxic Off-Pathway Amyloid-β Oligomers, Chembiochem, vol. 15, No. 17, Sep. 26, 2014, pp. 2577-2583.
Cho, Patricia Y. et al. A Cyclic Peptide Mimic of the β-Amyloid Binding Domain on Transthyretin, ACS Chemical Neuroscience, vol. 6, No. 5, Mar. 9, 2015, pp. 778-789.
Liu, Cong et al. Characteristics of Amyloid-Related Oligomers Revealed by Crystal Structures of Macrocyclic β-Sheet Mimics⇌, Journal of the American Chemical Society, vol. 133, No. 17, May 4, 2011, pp. 6736-6744.
Perez De La Lastra, J. M. et al. Epitope mapping of 10 monoclonal antibodies against the pig analogue of human membrane cofactor protein (MCP), Immunology, vol. 96, No. 4, Apr. 1, 1999, pp. 663-670.
Fritschi, Sarah K. et al. Highly potent soluble amyloid-β seeds in human Alzheimer brain but not cerebrospinal fluid. Brain: a journal of neurology 137: Pt 11. 2909-2915 Nov. 2014.
Kaplan Johanne. Harnessing the Power of Precision Medicine to Conquer Neurodegenerative Diseases. Presented Sep. 14, 2016.
Wilcock, Donna M. et al. Passive immunotherapy against Aβ in aged APP-transgenic mice reverses cognitive deficits and depletes parenchymal amyloid deposits in spite of increased vascular amyloid and microhemorrhage. Journal of Neuroinflammation, 2004, 1:24.
Racke, Margaret M. et al. Exacerbation of Cerebral Amyloid Angiopathy-Associated Microhemorrhage in Amyloid Precursor Protein Transgenic Mice by Immunotherapy is Dependent on Antibody Recognition of Deposited Forms of Amyloid β. The Journal of Neuroscience, Jan. 19, 2005. 25(3):629-636.
Pfeifer M. et al. Cerebral Hemorrhage After Passive Anti-Aβ Immunotherapy. Science. vol. 298 Nov. 15, 2002.
Wilcock, Donna M. et al. Deglycosylated Anti-Amyloid-β Antibodies Eliminate Cognitive Deficits and Reduce Parenchymal Amyloid

(56) References Cited

OTHER PUBLICATIONS with Minimal Vascular Consequences in Aged Amyloid Precursor Protein Transgenic Mice. Journal of Neuroscience. May 17, 2006. 26(20):5340-5346.
Goni, Fernando et al. Production of Monoclonal Antibodies to Pathologic β-sheet Oligomeric Conformers in Neurodegenerative Diseases. Scientific Reports. Aug. 2017.
Langer, Franziska et al. Soluble Aβ Seeds are Potent Inducers of Cerebral β-Amyloid Deposition. J Neurosci 31: 41. 14488-14495 Oct. 2011.
Tjernberg Lo, et al. Arrest of Aβ1-40 Fibril Formation by an Aβ Ligand. The Journal of Biological Chemistry. vol. 271, No. 15, Issue of Apr. 12, pp. 8545-8548, 1996.
Sardar Sinha, Maitrayee et al. Alzheimer's disease pathology propagation by exosomes containing toxic amyloid-beta oligomers. Acta Neuropathologica. Jun. 2018.
Kaplan, Johanne. Pre-Clinical: Basic Therapeutics—Targeting Amyloid or TAU. Presented at the Alzheimer's International Conference Jul. 2007.
Aprile, Francesco A. et al. Selective targeting of primary and secondary nucleation pathways in Aβ42 aggregation using a rational antibody scanning method. Molecular Neuroscience, Science Advances; 2017, 3. Jun. 21, 2017.
Wang, J. et al. Effects of an amyloid-beta 1-42 oligomers antibody screened from a phage display library in APP/PSI transgenic mice. Brain Res. Mar. 15, 2016, vol. 1635, pp. 169-179.
Silverman, Judith et al. Novel Amyloid-β Oligomer-Specific Epitopes: A Hypothesis Drivin Aproach to Alzheimer's Immunotherapeutics. Abstract presented at the Alzheimer's Association International Conference Jul. 2016.
Gibbs, Ebrima et al. Rational generation of Aβ oligomer-specific antibodies through computational identification of conformational epitopes. Abstract presented at the Alzheimer's Association International Conference on Jul. 2017.
Plotkin, Steven et al. A computational Method to Predict Disease-Specific Epitopes in Aβ, and its Application to Oligomer-Selective Antibodies for Alzheimer's Immunotherapy. Presented at the Alzheimer's association international conference on Jul. 27, 2016.
Hollta, Mikko et al. Evaluating Amyloid-β Oligomers in Cerebrospinal Fluid as a Biomarker for Alzheimer's Disease. Plos One. Jun. 2013, vol. 8, Issue 6.
Plotkin, Steven et al. Achieving the optimal profile for Alzheimer's immunotherapy: Rational generation of antibodies specific for toxic Aβ oligomers. Abstract presented at the American Academy of Neurology conference on Apr. 2017.
Cashman, Neil et al. Epitope Identification of Toxic Propagating Strains of Aβ Oligomers. presented at PRION 2017, the International Conference Deciphering Neurodegenerative Disorders in Edinburgh, Scottland on May 25, 2017.
Fukumoto, H. et al. High-molecular-weight beta-amyloid oligomers are elevated in cerebrospinal fluid of Alzheimer patients. the FASEB Journal 24, 2716-2726, 2010.
Lesne, S. E. et al. Brain amyloid-beta oligomers in ageing and Alzheimer's disease. Brain 136, 1383-1398, 2013.
Ferreira, S. T., et al. Soluble amyloid-b oligomers as synaptotoxins leading to cognitive impairment in Alzheimer's disease. Frontiers in Cellular Neuroscience 9, (2015).
Figueiredo, C. P. et al. Memantine rescues transient cognitive impairment caused by high-molecular-weight abeta oligorners but not the persistent impairment induced by low-molecular-weight oligomers. J Neurosci 33, 9626-9634, 2013.
Tapiola, Tero, et al. Cerebrospinal Fluid β-Amyloid 42 and Tau Proteins as Biomarkers of Alzheimer-Type Pathologic Changes in the Brain. Arch Neurol. 2009, 66(3):382-389.
Zola, Stuart M. et al. "A Behavioral Task Predicts Conversion to Mild Cognitive Impairment and Alzheimer's Disease." American Journal of Alzheimer's Disease & Other Dementias. 28(2) 179-184 (2012).
Lu, J.X. et al. "Molecular Structure of Beta-Amyloid Fibrils in Alzheimer's Disease Brain Tissue" Cell vol. 154(6) p. 1257 (2013).
Xiao, Y. et al. A Beta (1-42) Fibril Structure Illuminates Self-Recognition and Replication of Amyloid in Alzheimer's Disease. Nat.Struct.Mol.Biol. vol. 22(6) p. 499-505 (2015).
Petkova, A.et al. Experimental Constraints on Quaternary Structure in Alzheimer's Beta-Amyloid Fibrils Biochemistry. vol. 45 p. 498 (2006).
Giulian, D. "The HHQK domain of β-amyloid provides a structural basis for the immunopathology of Alzheimer's disease." J. Biol. Chem. 1998, 273(45), 29719-26.
Winkler, K. "Competition of Aβ amyloid peptide and apolipoprotein E for receptor-mediated endocytosis." J. Lipid Res. 1999, 40(3), 447-55.
Crespi, Gabriela A. N. et al. "Molecular basis for mid-region amyloid-b capture by leading Alzheimer's disease immunotherapies." Scientific Reports. 5 : 9649, 2015.
Hilser, Vincent J. et al. "Structure-based calculation of the equilibrium folding pathway of proteins. correlation with hydrogen exchange protection factors." J. Mol. Biol., 262:756-772, 1996.
Cohen, Samuel I. A. et al. Proliferation of amyloid-β42 aggregates occurs through a secondary nucleation mechanism. Proc. Natl.l Acad. Sci. USA, 110(24):9758-9763, 2013.
Sormanni, Pietro et al. The camsol method of rational design of protein mutants with enhanced solubility. Journal of Molecular Biology, 427(2):478-490, 2015.
Blacker, Deborah et al. Reliability and Validity of NINCDS-ADRDA Criteria for Alzheimer's Disease the National Institute of Mental Health Genetics Initiative. Arch Neurol. 51(12):1198-1204 (1994).
Hamley, I.W. "PEG-Peptide Conjugates" 2014; 15, 1543-1559; dx.doi.org/10.1021/bm500246w.
Roberts, MJ. et al. "Chemistry for peptide and protein PEGylation" 64: 116-127.
Karlin, Samuel et al. Methods for assessing the statistical significance of molecular sequence features by using general scoring schemes. Proc. Natl. Acad. Sci. U.S.A. 87:2264-2268.
Karlin, Samuel et al. Applications and statistics for multiple high-scoring segments in molecular sequences. 1993, Proc. Natl. Acad. Sci. U.S.A. 90:5873-5877.
Altschul et al. Basic Local Alignment Search Tool. 1990, J. Mol. Biol. 215:403.
Altschul et al. Gapped BLAST and PSI-BLAST: a new generation of protein database search programs. 1997, Nucleic Acids Res. 25:3389-3402.
Myers et al. Optimal alignments in linear space. 1988, Cabios 4:11-17.
Kohler G. et al. Continuous cultures of fused cells secreting antibody of predefined specificity. Nature 256:495-497, 1975.
Ward et al. Binding activities of a repertoire of single immuno-globulin variable domains secreted from *Escherichia coli*. Nature 41:544-546 1989.
Riechmann et al. Reshaping human antibodies for therapy. Nature, 332:323-327, 1988.
Wang, J. et al. Effects of an amyloid-beta 1-42 oligomers antibody screened from a phage display library in APP/PS1 transgenic mice. Brain Res. Mar. 15, 2016, vol. 1635, pp. 169-179.
Yu YZ, et al. Strikingly reduced amyloid burden and improved behavioral performance in Alzheimer's disease mice immunized with recombinant chimeric vaccines by hexavalent foldable A_1-15 fused to toxin-derived carrier proteins. J Alzheimers Dis 2014;41:243-60.
Wang, HC, et al.Peripherally administered sera antibodies recognizing amyloid-beta oligomers mitigate Alzheimer's disease-like pathology and cognitive decline in aged 3x Tg-AD mice, Vaccine 2016.
Paganetti PA et al. Amyloid precursor protein truncated at any of the γ-secretase sites is not cleaved to β-amyloid, J.Neurosci. Res. 46 (1996) 283-293.
Kahlert H. et al. Characterization of major allergens of Parietaria officinalis. Int Arch Allergy Immunol Feb. 1996; 109(2):141-9.
Kaplan, Johanne. Targeting of Toxic Amyloid-Beta Oligomer Species by Monoclonal Antibody PMN310: Precision Drug Design for

(56) References Cited

OTHER PUBLICATIONS

Alzheimer's Disease. Abstract and slides presented at the Alzheimer's Association International Conference Jul. 17, 2017 in London, England.
NCBI Blast: Protein Sequence (8 letters). CDR-H1 GYSFTSYW. Retrieved on Feb. 8, 2017 from <<https://blast.ncbi.nlm.nih.gov/Blast.cgi>>.
NCBI Blast: Protein Sequence (9 letters). CDR-H2 VHPGRGVST. Retrieved on Feb. 8, 2017 from <<https://blast.ncbi.nlm.nih.gov/Blast.cgi>>.
NCBI Blast: Protein Sequence (13 letters). CDR-H3 SRSHGNTYWFFDV. Retrieved on Feb. 8, 2017 from <<https://blast.ncbi.nlm.nih.gov/Blast.cgi>>.
NCBI Blast: Protein Sequence (11 letters). CDR-L1 QSIVHSNGNTY. Retrieved on Feb. 8, 2017 from <<https://blast.ncbi.nlm.nih.gov/Blast.cgi>>.
NCBI Blast: Protein Sequence (3 letters). CDR-L2 KVS. Retrieved on Feb. 8, 2017 from <<https://blast.ncbi.nlm.nih.gov/Blast.cgi>>.
NCBI Blast: Protein Sequence (9 letters). CDR-L3 FQGSHVPFT. Retrieved on Feb. 8, 2017 from <<https://blast.ncbi.nlm.nih.gov/Blast.cgi>>.
European Patent Application No. 16863268.5 Extended European Search Report dated Apr. 15, 2019.
Rudikoff et al., Single amino acid substitution altering antigen-binding specificity. Proc Natl Acad Sci USA 1982; 79:1979-1983.
MacCallum et al., Antibody-antigen Interactions: Contact Analysis and Binding Site Topography. J. Mol. Biol., 1996;262:732-745.
Pascalis et al., Grafting of "Abbreviated" Complementarity-Determining Regions Containing Specificity-Determining Regions Containing Specificity-Determining Residues Essential for Ligand Contact to Engineer a Less Immunogenic Humanized Monoclonal Antibody. The Journal of Immunology, 2002; 169: 3076-3084.
Casset et al., A peptide mimetic of an anti-CD4 monoclonal antibody by rational design. BBRC, 2003; 307:198-205.
Vajdos et al., Comprehensive Functional Maps of the Antigen-binding Site of an Anti-ErbB2 Antibody Obtained with Shotgun Scanning Mutagenesis. J. Mol. Med., 2002; 320: 415-428.
Holm et al., Functional mapping and single chain construction of the anti-cytokeratin 8 monoclonal antibody TS1. Mol. Immunol., 2007; 44: 1075-1084.
Chen et al., Selection and Analysis of an Optimized Anti-VEGF Antibody: Crystal Structure of an Affinity-matured Fab in Complex with Antigen. J. Mol. Bio., 1999; 293: 865-881.
Wu et al., Humanization of a Murine Monoclonal Antibody by Simultaneousl Optimization of Framework and CDR Residues. J. Mol. Biol.,1999; 294: 151-162.
Burgess et al., Possible Dissociation of the Heparin-binding and Mitogenic Activities of Heparin-binding (Acidic Fibroblast) Growth Factor-1 from its Receptor-binding Activities by Site-directed Mutagenesis of a Single Lysine Residue. J of Cell Bio. 1990, 111:2129-2138.
Bowie et al., Deciphering the Message in Protein Sequences: Tikerance to Amino Acid Substitutions. Science, 1990, 247:1306-1310.
Pawson et al., Assembly of Cell Regulatory Systems Through Protein Interaction Domains. Science, 2003, 300:445-452.
Alaoui-Ismaili et al., Design of second generation therapeutic recombinant bone morphogenetic proteins. Cytokine Growth Factor Rev. 2009; 20:501-507.
Guo et al., Protein tolerance to random amino acid change. PNAS 2004; 101:9205-9210.

\* cited by examiner

B

A. Cyclo(CGQKLVG)

Chemical Formula: $C_{29}H_{51}N_9O_8S$
Molecular Weight: 685.84

B.  Cyclo(C-PEG2-QKLVG)

Chemical Formula: $C_{33}H_{59}N_9O_{10}S$
Molecular Weight: 773.94 c.   Cyclo(CGQKLV-PEG2)

Chemical Formula: $C_{33}H_{59}N_9O_{10}S$
Molecular Weight: 773.94

A.

B.

A.

B.

C.

D.

A.

B.

C.

A.

B.

ANTI-AMYLOID BETA ANTIBODIES BINDING TO A CYCLIC AMYLOID BETA PEPTIDE

RELATED APPLICATIONS

This application is a national phase entry of PCT/CA2016/051305, filed Nov. 9, 2016, which claims the benefit of priority of U.S. Patent Application Ser. No. 62/253,044, filed Nov. 9, 2015; U.S. Patent Application Ser. No. 62/289,893, filed on Feb. 1, 2016; U.S. Patent Application Ser. No. 62/365,634, filed on Jul. 22, 2016; and U.S. Patent Application Ser. No. 62/393,615, filed on Sep. 12, 2016, each of which are incorporated herein by reference.

FIELD

The present disclosure relates to Amyloid beta (A-beta or Aβ) epitopes and antibodies thereto and more specifically to conformational A-beta epitopes that are predicted to be selectively accessible in A-beta oligomers, and related antibody compositions and uses thereof.

BACKGROUND

Amyloid-beta (A-beta), which exists as a 36-43 amino acid peptide, is a product released from amyloid precursor protein (APP) by the enzymes β and γ secretase. In AD patients, A-beta can be present in soluble monomers, insoluble fibrils and soluble oligomers. In monomer form, A-beta exists as a predominantly unstructured polypeptide chain. In fibril form, A-beta can aggregate into distinct morphologies, often referred to as strains. Several of these structures have been determined by solid-state NMR.

For, example, structures for several stains of fibrils are available in the Protein Data Bank (PDB), a crystallographic database of atomic resolution three dimensional structural data, including a 3-fold symmetric Aβ structure (PDB entry, 2M4J); a two-fold symmetric structure of Aβ-40 monomers (PDB entry 2LMN), and a single-chain, parallel in-register structure of Aβ-42 monomers (PDB entry 2MXU).

The structure of 2M4J is reported in J. X. LU, W. QIANG, W. M. YAU, C. D. SCHWIETERS, S. C. MEREDITH, R. TYCKO, MOLECULAR STRUCTURE OF BETA-AMYLOID FIBRILS IN ALZHEIMER'S DISEASE BRAIN TISSUE. CELL Vol. 154 p. 1257 (2013) and the structure of 2MXU is reported in Y. XIAO, B. MA, D. MCELHENY, S. PARTHASARATHY, F. LONG, M. HOSHI, R. NUSSINOV, Y. ISHII A BETA (1-42) FIBRIL STRUCTURE ILLUMINATES SELF-RECOGNITION AND REPLICATION OF AMYLOID IN ALZHEIMER'S DISEASE. NAT. STRUCT. MOL. BIOL. Vol. 22 p. 499 (2015).

A-beta oligomers have been shown to kill cell lines and neurons in culture and block a critical synaptic activity that subserves memory, referred to as long term potentiation (LTP), in slice cultures and living animals.

The structure of the oligomer has not been determined to date. Moreover, NMR and other evidence indicates that the oligomer exists not in a single well-defined structure, but in a conformationally-plastic, malleable structural ensemble with limited regularity. Moreover, the concentration of toxic oligomer species is far below either that of the monomer or fibril (estimates vary but on the order of 1000-fold below or more), making this target elusive.

U.S. Pat. Nos. 5,766,846; 5,837,672; and 5,593,846 (which are incorporated herein by reference) describe the production of murine monoclonal antibodies to the central domain of the Aβ peptide. WO 01/62801 describes antibodies that bind A-beta between amino acids 13-28. WO2004071408 discloses humanized antibodies. WO2008088983A1 describes an antibody fragment that binds amyloid beta (A-beta) peptide and is covalently attached to one or more molecules of polyethylene glycol (PEG), the antibody fragment specifically binding human A-beta peptide between amino acid positions 13-28. Solanezumab and Crenezumab bind amino acids 16-26 on A-beta. Crenezumab interacts with the monomer, oligomer and fibril. Midregion antibodies, including solanezumab (picomolar affinity) and crenezumab (nanomolar affinity), appear to preferentially bind monomeric A-beta [1].

Antibodies that preferentially or selectively bind A-beta oligomers are desirable.

SUMMARY

Described herein is an epitope, optionally a conformational epitope, in A-beta consisting of residues QKLV (SEQ ID NO: 1) or a part thereof, and antibodies thereto. The epitope is identified as selectively exposed in the oligomeric species of A-beta, in a conformation that distinguishes it from that in the monomer.

An aspect includes a compound, preferably a cyclic compound comprising an A-beta peptide the peptide comprising QKL and up to 8, 7 or 6 A-beta residues, and a linker, wherein the linker is covalently coupled to the A-beta peptide N-terminus residue and the A-beta C-terminus residue.

In an embodiment, the A-beta peptide is selected from a peptide having a sequence of any one of SEQ ID NOS: 1-10, optionally selected from QKLV (SEQ ID NO: 1), HQKLV (SEQ ID NO: 2), HQKLVF (SEQ ID NO: 9) and QKLVF (SEQ ID NO: 10).

In another embodiment, the cyclic compound is a cyclic peptide.

In another embodiment, the cyclic compound comprises i) at least Q in an alternate conformation compared to Q in the context of a corresponding linear compound and/or ii) a conformation for Q, and/or K, and/or L as measured by entropy that is at least 10%, at least 20%, at least 25%, at least 30%, at least 35%, at least 40% more constrained compared to a corresponding linear compound.

In another embodiment, the A-beta peptide is QKLV (SEQ ID NO: 1).

In another embodiment, the compound further comprises a detectable label.

In another embodiment, the linker comprises or consists of 1-8 amino acids and/or equivalently functioning molecules and/or one or more functionalizable moieties.

In another embodiment, the linker amino acids are selected from A and G, and/or wherein the functionalizable moiety is C.

In another embodiment, the linker comprises or consists of amino acids GCG or CGC.

In another embodiment, the linker comprises a PEG molecule.

In another embodiment, the cyclic compound is selected from the following structures:

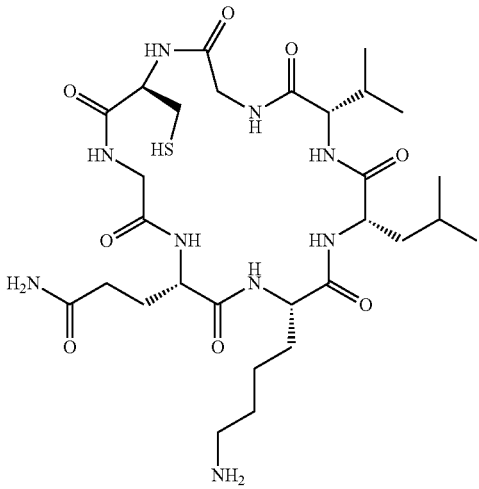

Cyclo(CGQKLVG)
Chemical Formula: $C_{29}H_{51}N_9O_8S$
Molecular Weight: 685.84

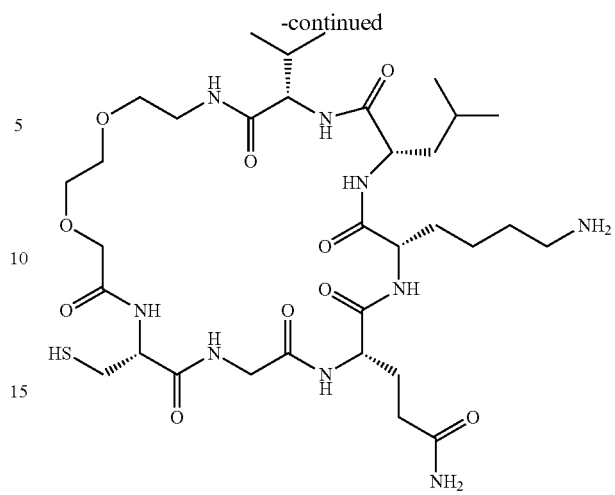

Cyclo(CGKLV-PEG2)
Chemical Formula: $C_{33}H_{59}N_9O_{10}S$
Molecular Weight: 773.94 and

An aspect includes an immunogen comprising the cyclic compound described herein.

In an embodiment, the cyclic compound is coupled to a carrier protein or immunogenicity enhancing agent.

In an embodiment, the carrier protein is bovine serum albumin (BSA) or the immunogenicity-enhancing agent is keyhole limpet haemocyanin (KLH).

An aspect includes a composition comprising the compound described herein or the immunogen described herein.

In an embodiment, the composition described herein, further comprises an adjuvant.

In another embodiment, the adjuvant is aluminum phosphate or aluminum hydroxide.

An aspect includes isolated antibody that specifically binds to an A-beta peptide having a sequence of QKLV (SEQ ID NO: 1) or a related epitope sequence, optionally as set forth in any one of SEQ ID NOS: 1-10.

In an embodiment, the antibody specifically binds an epitope on A-beta, wherein the epitope comprises at least two consecutive amino acid residues predominantly involved in binding to the antibody, wherein the at least two consecutive amino acids are QK embedded within QKLV (SEQ ID NO: 1).

In another embodiment, the epitope comprises or consists of QKLV (SEQ ID NO: 1), HQKLV (SEQ ID NO: 2), HQKLVF (SEQ ID NO: 9) or QKLVF (SEQ ID NO: 10).

In another embodiment, the antibody is a conformation specific and/or selective antibody that specifically or selectively binds to AEDV or a related epitope peptide presented in a cyclic compound, optionally a cyclic compound described herein, preferably a cyclic peptide having a sequence as set forth in SEQ ID NO: 3.

In another embodiment, the antibody selectively binds A-beta oligomer over A-beta monomer and/or A-beta fibril.

In another embodiment, the selectivity is at least 3 fold, at least 5 fold, at least 10 fold, at least 20 fold, at least 30 fold, at least 40 fold, at least 50 fold, at least 100 fold, at least 500 fold, at least 1000 fold more selective for A-beta oligomer over A-beta monomer and/or A-beta fibril.

In another embodiment, the antibody does not specifically and/or selectively bind a linear peptide comprising sequence QKLV (SEQ ID NO: 1) or a related epitope, optionally

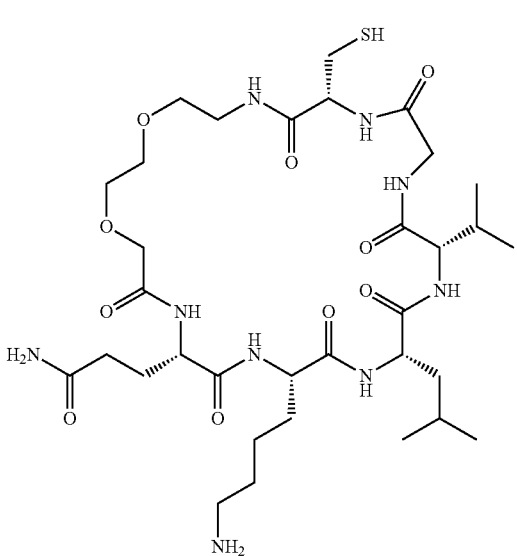

Cyclo(C-PEG2-QKLVG)
Chemical Formula: $C_{33}H_{59}N_9O_{10}S$
Molecular Weight: 773.94 wherein the sequence of the linear peptide is a linear version of a cyclic compound used to raise the antibody, optionally a linear peptide having a sequence as set forth in SEQ ID NO: 3.

In another embodiment, the antibody lacks or has negligible binding to A-beta monomer and/or A-beta fibril plaques in situ.

In an embodiment, the antibody is produced using a cyclic compound described herein, optionally a cyclic peptide described herein.

In another embodiment, the antibody is a monoclonal antibody or a polyclonal antibody.

In another embodiment, the antibody is a humanized antibody.

In another embodiment, the antibody is an antibody binding fragment selected from Fab, Fab', F(ab')2, scFv, dsFv, ds-scFv, dimers, nanobodies, minibodies, diabodies, and multimers thereof.

In another embodiment, the antibody described herein, comprises a light chain variable region and a heavy chain variable region, optionally fused, the heavy chain variable region comprising complementarity determining regions CDR-H1, CDR-H2 and CDR-H3, the light chain variable region comprising complementarity determining region CDR-L1, CDR-L2 and CDR-L3 and with the amino acid sequences of said CDRs comprising the sequences:

```
CDR-H1
                                  (SEQ ID NO: 11)
GYTFTDYE

CDR-H2
                                  (SEQ ID NO: 12)
IDPETGDT

CDR-H3
                                  (SEQ ID NO: 13)
TSPIYYDYDWFAY

CDR-L1
                                  (SEQ ID NO: 14)
QSLLNNRTRKNY

CDR-L2
                                  (SEQ ID NO: 15)
WAS

CDR-L3
                                  (SEQ ID NO: 16)
KQSYNLRT

CDR-H1
                                  (SEQ ID NO: 21)
GFSLSTSGMG

CDR-H2
                                  (SEQ ID NO: 22)
IWWDDDK

CDR-H3
                                  (SEQ ID NO: 23)
ARSITTVVATPFDY

CDR-L1
                                  (SEQ ID NO: 24)
QNVRSA

CDR-L2
                                  (SEQ ID NO: 25)
LAS

CDR-L3
                                  (SEQ ID NO: 26)
LQHWNSPFT
```

In another embodiment, the antibody comprises a heavy chain variable region comprising: i) an amino acid sequence as set forth in SEQ ID NO: 18 or 28; ii) an amino acid sequence with at least 50%, at least 60%, at least 70%, at least 80% or at least 90% sequence identity to SEQ ID NO: 18 or 28, wherein the CDR sequences are as set forth in SEQ ID NO:11, 12, 13, 21, 22 and 23, or iii) a conservatively substituted amino acid sequence i).

In another embodiment, the antibody comprises a light chain variable region comprising i) an amino acid sequence as set forth in SEQ ID NO: 20 or 30, ii) an amino acid sequence with at least 50%, at least 60%, at least 70%, at least 80% or at least 90% sequence identity to SEQ ID NO: 20 or 30, wherein the CDR sequences are as set forth in SEQ ID NO: 14, 15, 16, 24, 25 and 26, or iii) a conservatively substituted amino acid sequence of i).

In another embodiment, the heavy chain variable region amino acid sequence is encoded by a nucleotide sequence as set forth in SEQ ID NO: 17 or 27 or a codon degenerate or optimized version thereof; and/or the antibody comprises a light chain variable region amino acid sequence encoded by a nucleotide sequence as set out in SEQ ID NO: 19 or 29 or a codon degenerate or optimized version thereof.

In another embodiment, the heavy chain variable region comprises or consists of an amino acid sequence as set forth in SEQ ID NO:18 or 28 and/or the light chain variable region comprises or consists of an amino acid sequence as set forth in SEQ ID NO: 20 or 30.

In another embodiment, the antibody competes for binding to human A-beta with an antibody comprising the CDR sequences as recited in Table 6 and/or 8.

An aspect includes an immunoconjugate comprising the antibody described herein and a detectable label or cytotoxic agent.

In an embodiment, the detectable label comprises a positron emitting radionuclide, optionally for use in subject imaging such as PET imaging.

An aspect includes a composition comprising the antibody described herein, or the immunoconjugate described herein, optionally with a diluent.

An aspect includes a nucleic acid molecule encoding a proteinaceous portion of the compound or immunogen described herein, the antibody described herein or proteinaceous immunoconjugates described herein.

An aspect includes a vector comprising the nucleic acid described herein.

An aspect includes a cell expressing an antibody described herein, optionally wherein the cell is a hybridoma comprising the vector described herein.

An aspect includes a kit comprising the compound described herein, the immunogen described herein, the antibody described herein, the immunoconjugate described herein, the composition described herein, the nucleic acid molecule described herein, the vector described herein or the cell described herein.

An aspect includes a method of making the antibody described herein, comprising administering the compound or immunogen described herein or a composition comprising said compound or immunogen to a subject and isolating antibody and/or cells expressing antibody specific or selective for the compound or immunogen administered and/or A-beta oligomers, optionally lacking or having negligible binding to a linear peptide comprising the A-beta peptide and/or lacking or having negligible plaque binding.

An aspect includes a method of determining if a biological sample comprises A-beta, the method comprising:

a. contacting the biological sample with an antibody described herein or the immunoconjugate described herein; and
b. detecting the presence of any antibody complex.

In an embodiment, the biological sample contains A-beta oligomer the method comprising:
a. contacting the sample with the antibody described herein or the immunoconjugate described herein that is specific and/or selective for A-beta oligomers under conditions permissive for forming an antibody: A-beta oligomer complex; and
b. detecting the presence of any complex;
wherein the presence of detectable complex is indicative that the sample may contain A-beta oligomer.

In another embodiment, the amount of complex is measured.

In another embodiment, the sample comprises brain tissue or an extract thereof, whole blood, plasma, serum and/or CSF.

In another embodiment, the sample is a human sample.

In another embodiment, the sample is compared to a control, optionally a previous sample.

In another embodiment, the level of A-beta is detected by SPR.

An aspect includes a method of measuring a level of A-beta in a subject, the method comprising administering to a subject at risk or suspected of having or having AD, an immunoconjugate comprising an antibody described herein wherein the antibody is conjugated to a detectable label; and detecting the label, optionally quantitatively detecting the label.

In an embodiment, the label is a positron emitting radionuclide.

An aspect includes a method of inducing an immune response in a subject, comprising administering to the subject a compound or combination of compounds described herein, optionally a cyclic compound comprising QKLV (SEQ ID NO:1) or a related epitope peptide sequence, an immunogen and/or composition comprising said compound or said immunogen; and optionally isolating cells and/or antibodies that specifically or selectively bind the A-beta peptide in the compound or immunogen administered.

An aspect includes a method of inhibiting A-beta oligomer propagation, the method comprising contacting a cell or tissue expressing A-beta with or administering to a subject in need thereof an effective amount of an A-beta oligomer specific or selective antibody or immunoconjugate described herein, to inhibit A-beta aggregation and/or oligomer propagation.

An aspect includes a method of treating AD and/or other A-beta amyloid related diseases, the method comprising administering to a subject in need thereof i) an effective amount of an antibody or immunoconjugate described herein, optionally an A-beta oligomer specific or selective antibody, or a pharmaceutical composition comprising said antibody; 2) administering an isolated cyclic compound comprising QKLV (SEQ ID NO:1) or a related epitope sequence or immunogen or pharmaceutical composition comprising said cyclic compound, or 3) a nucleic acid or vector comprising a nucleic acid encoding the antibody of 1 or the immunogen of 2, to a subject in need thereof.

In an embodiment, a biological sample from the subject to be treated is assessed for the presence or levels of A-beta using an antibody described herein.

In another embodiment, more than one antibody or immunogen is administered.

In another embodiment, the antibody, immunoconjugate, immunogen, composition or nucleic acid or vector is administered directly to the brain or other portion of the CNS.

In another embodiment, the composition is a pharmaceutical composition comprising the compound or immunogen in admixture with a pharmaceutically acceptable, diluent or carrier.

An aspect includes an isolated peptide comprising an A beta peptide consisting of the sequence of any one of the sequences set forth in SEQ ID NOS: 1-10.

In an embodiment, the peptide is a cyclic peptide comprising a linker wherein the linker is covalently coupled to the A-beta peptide N-terminus residue and/or the A-beta C-terminus residue.

In another embodiment, the isolated peptide described herein comprises a detectable label.

An aspect includes a nucleic acid sequence encoding the isolated peptide described herein.

An aspect includes a hybridoma expressing the antibody described herein.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

An embodiment of the present disclosure will now be described in relation to the drawings in which.

Figure 1:
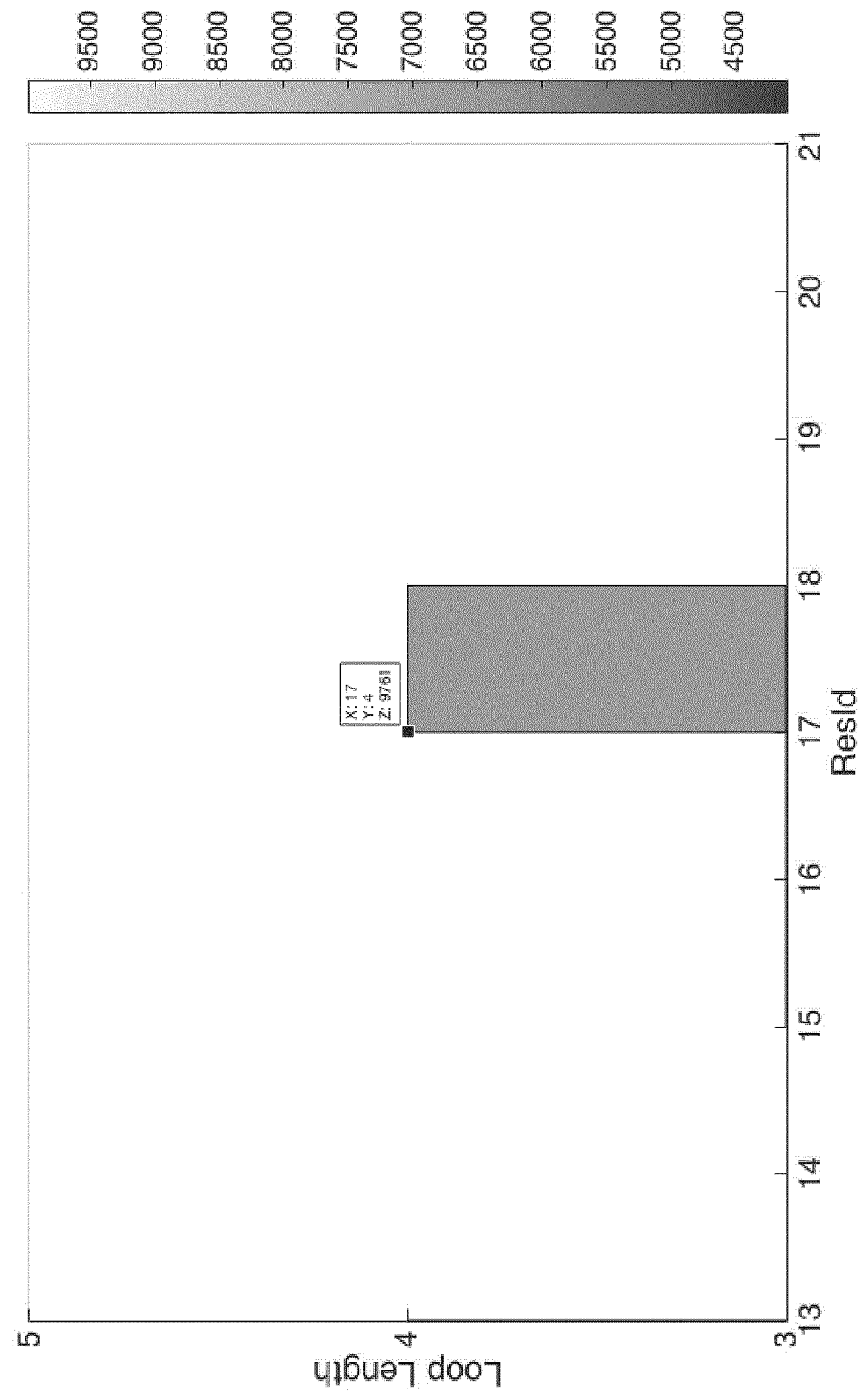
FIG. 1 is a free energy landscape graph depicting the partial unfolding of 2M4J.

Table 2 shows the binding properties summary for selected purified antibodies.

Table 3 lists the oligomer binding—monomer binding for an antibody raised against cyclo(CGQKLVG) (SEQ ID NO: 3).

Table 4 lists properties of antibodies tested on formalin fixed tissues.

Table 5 is an exemplary toxicity assay.

Table 6 lists CDR sequences of clone 305-61 (7E9)

Table 7 lists heavy chain and light chain variable sequences of clone 305-61 (7E9)

Table 8 lists CDR sequences of clone 305-62 (8H10)

Table 9 lists heavy chain and light chain variable sequences of clone 305-62 (8H10)

Table 10 is a table of A-beta epitope sequences and select A-beta sequences with linker.

Table 11 provides the full A-beta 1-42 human polypeptide sequence

DETAILED DESCRIPTION OF THE DISCLOSURE

A prerequisite for the generation of oligomer-specific antibodies is the identification of targets on A-beta peptide that are not present, or present to a much lesser degree, on either the monomer or fibril. These oligomer-specific epitopes may not differ in primary sequence from the corresponding segment in monomer or fibril, however they would be conformationally distinct in the context of the oligomer. That is, they would present a distinct conformation in terms of backbone and/or sidechain conformation in the oligomer that would not be present in the monomer and/or fibril.

Antibodies raised to linear peptide regions tend not to be selective for oligomer, and thus bind to monomer as well.

To develop antibodies selective for oligomeric forms of A-beta, the inventors sought to identify regions of sequence in the fibril that are prone to disruption in the context of the fibril, and would be exposed as well on the surface of the oligomer.

As described in the Examples, the inventors identified a region predicted to be prone to disruption in the context of the fibril. The inventors designed cyclic compounds comprising the identified epitope to satisfy the above criteria of higher curvature, higher exposed surface area, and/or alternative dihedral angle distributions.

Antibodies were raised using a cyclic peptide comprising the target region that selectively bound the cyclic peptide compared to a linear peptide of the same sequence (e.g. corresponding linear sequence). Experimental results are described and identify epitope-specific and conformationally selective antibodies that bind synthetic oligomer selectively compared to synthetic monomers, bind CSF from AD patients preferentially over control CSF and/or bind soluble brain extract from AD patients preferentially over control soluble brain extract. Further staining of AD brain tissue identified antibodies that show no or negligible plaque binding and in vitro studies found that the antibodies inhibited Aβ oligomer propagation and aggregation.

I. Definitions

As used herein, the term 'A-beta' may alternately be referred to as 'amyloid beta', 'amyloid β', 'A-beta' or 'Aβ'. Amyloid beta is a peptide of 36-43 amino acids and as used herein includes all wild-type and mutant forms of all species, particularly human A-beta. A-beta40 refers to the 40 amino acid form; A-beta42 refers to the 42 amino acid form, etc. The amino acid sequence of human wildtype A-beta42 is shown in SEQ ID NO: 31.

As used herein, the term "A-beta monomer" herein refers to an individual subunit form of A-beta (e.g. 1-40, 1-41, 1-42, 1-43) peptide.

As used herein, the term "A-beta oligomer" refers to a plurality of any of the A-beta subunits wherein several (e.g. at least two) A-beta monomers are non-covalently aggregated in a conformationally-flexible, partially-ordered, three-dimensional globule of less than about 100, or more typically less than about 50 monomers. For example, an oligomer may contain 3 or 4 or 5 or more monomers. The term "A-beta oligomer" as used herein includes both synthetic A-beta oligomer and/or native A-beta oligomer. "Native A-beta oligomer" refers to A-beta oligomer formed in vivo, for example in the brain and CSF of a subject with AD.

As used herein, the term "A-beta fibril" refers to a molecular structure that comprises assemblies of non-covalently associated, individual A-beta peptides that show fibrillary structure under an electron microscope. The fibrillary structure is typically a "cross beta" structure; there is no theoretical upper limit on the size of multimers, and fibrils may comprise thousands or many thousands of monomers. Fibrils can aggregate by the thousands to form senile plaques, one of the primary pathological morphologies diagnostic of AD.

Figure 4:
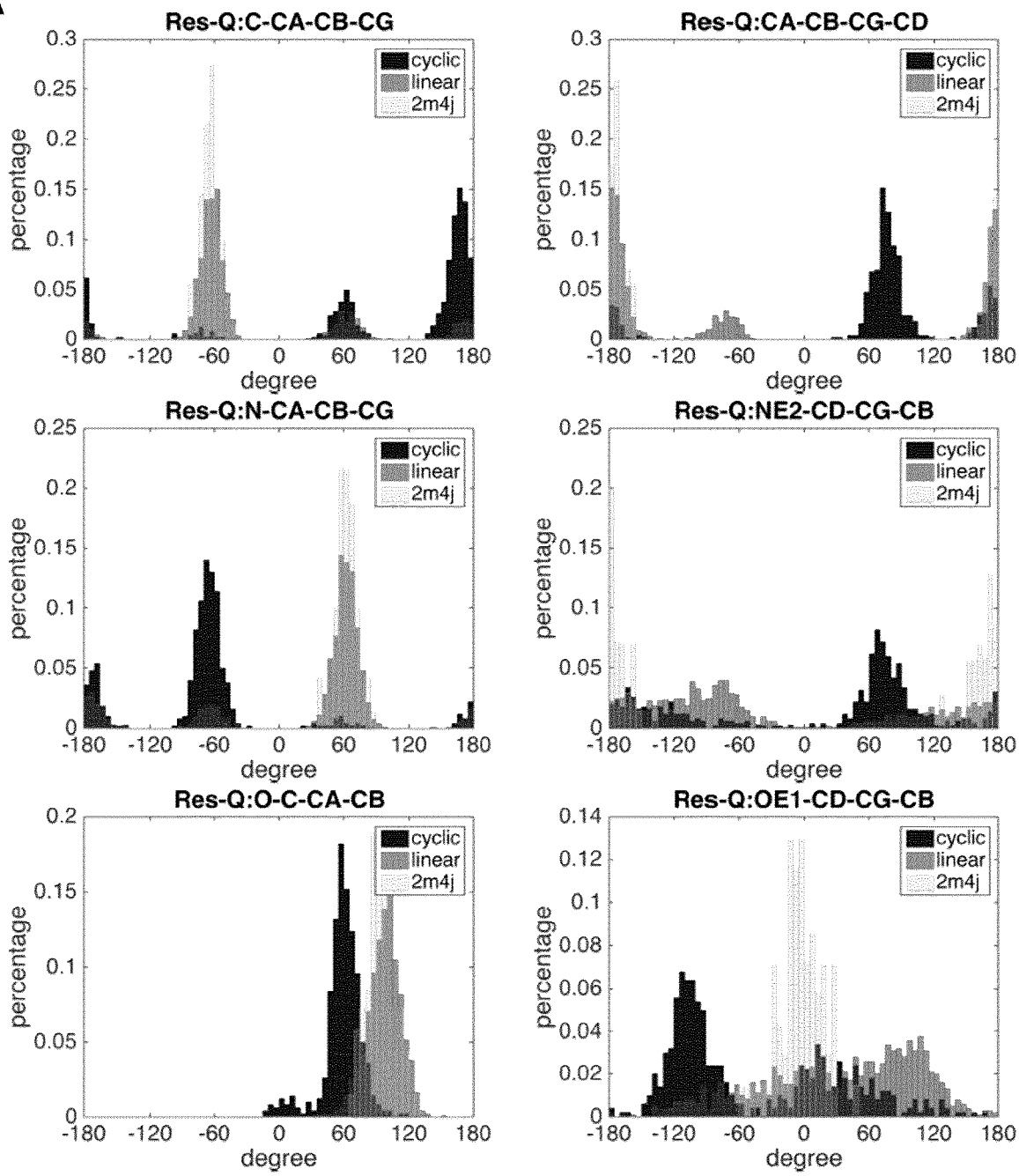
FIG. 4(a) is a series of graphs showing the dihedral angle distributions, for all the dihedral angles involving the side chain heavy atoms of residue Q15.
FIG. 4(b) is a schematic of a cyclic peptide comprising QKLV (SEQ ID NO: 1).
Figure 4:
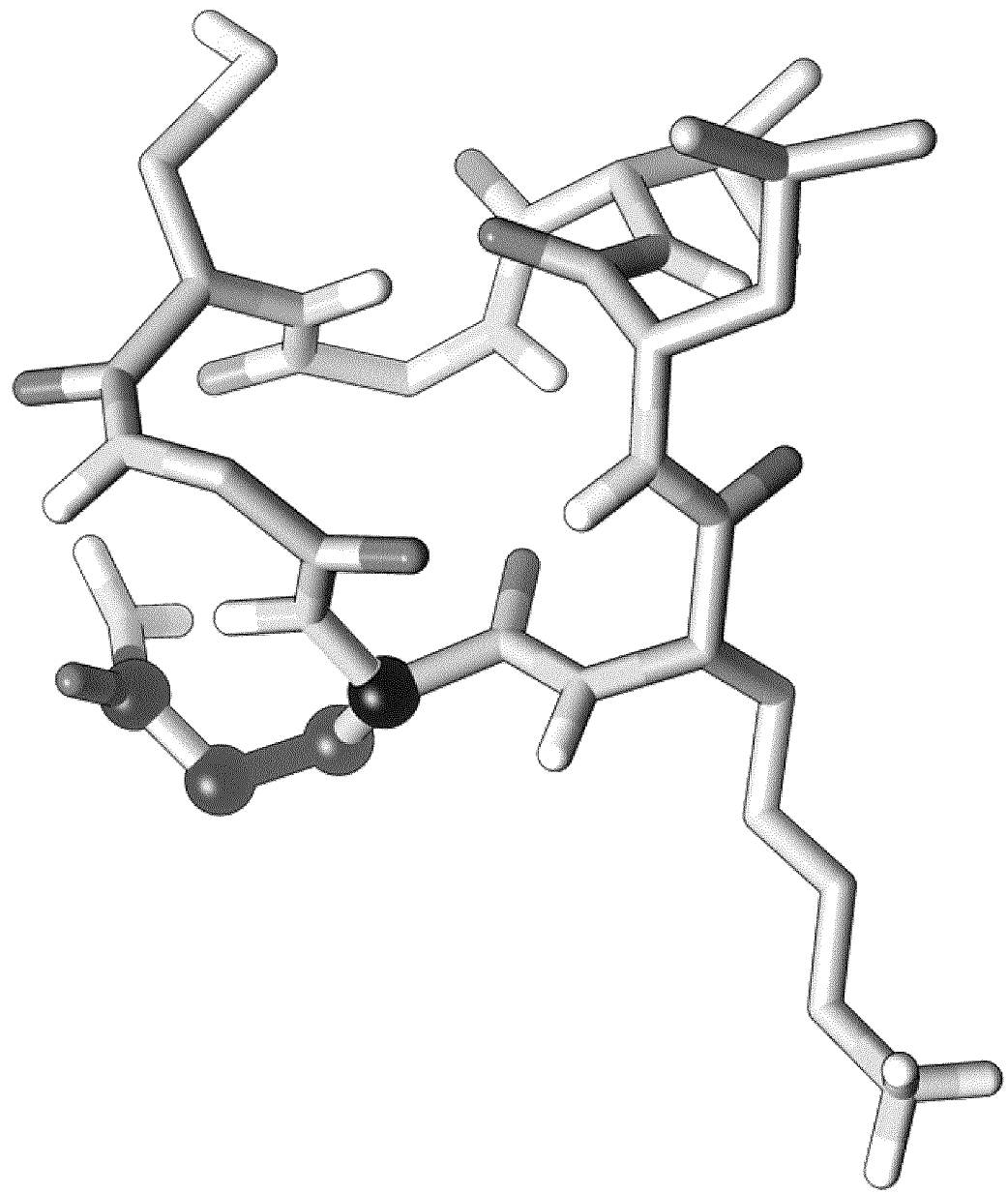
Figure 5:
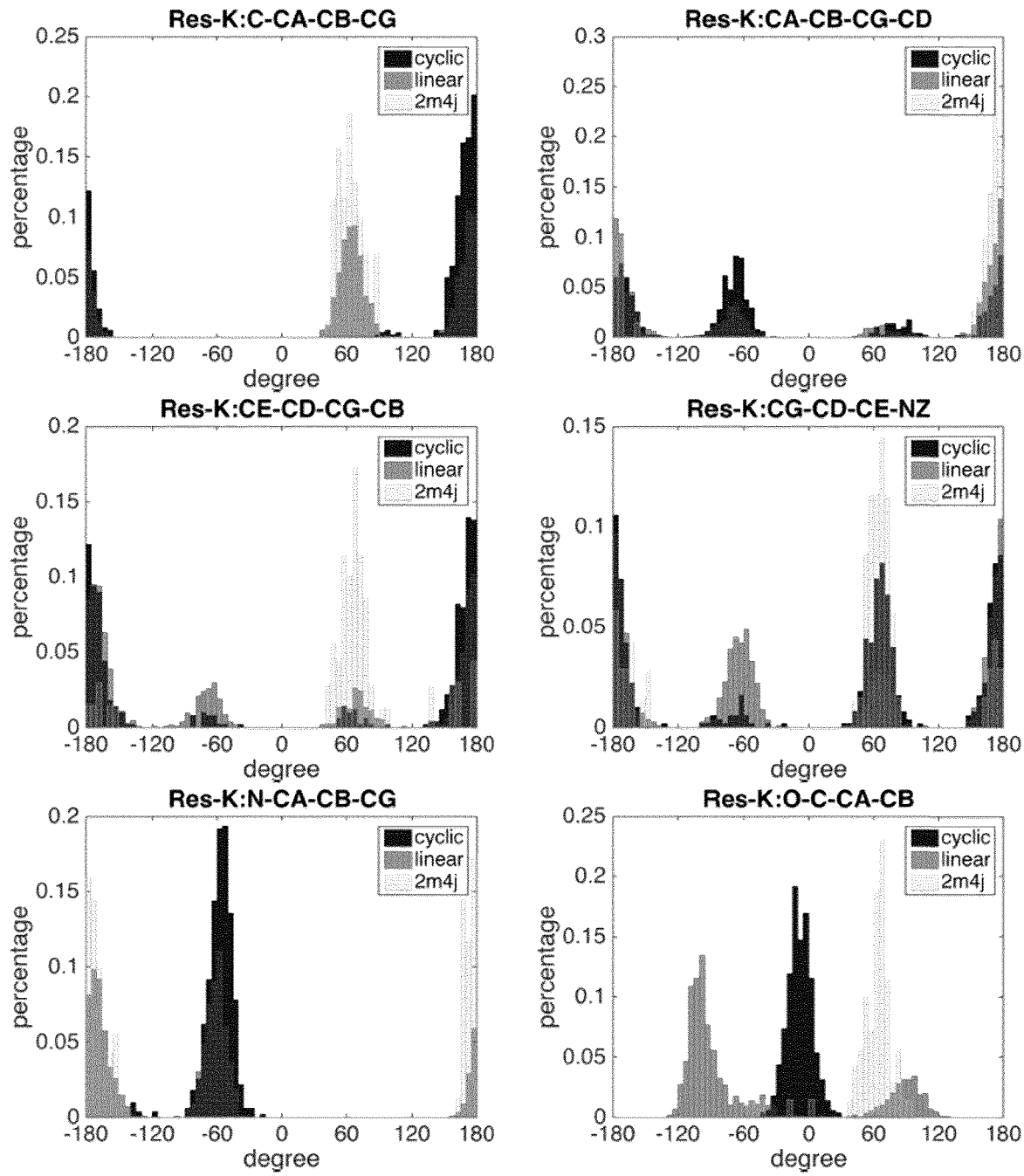
FIG. 5 is a graph showing dihedral angle distributions for angles involving the side chain heavy atoms of K16.
Figure 6:
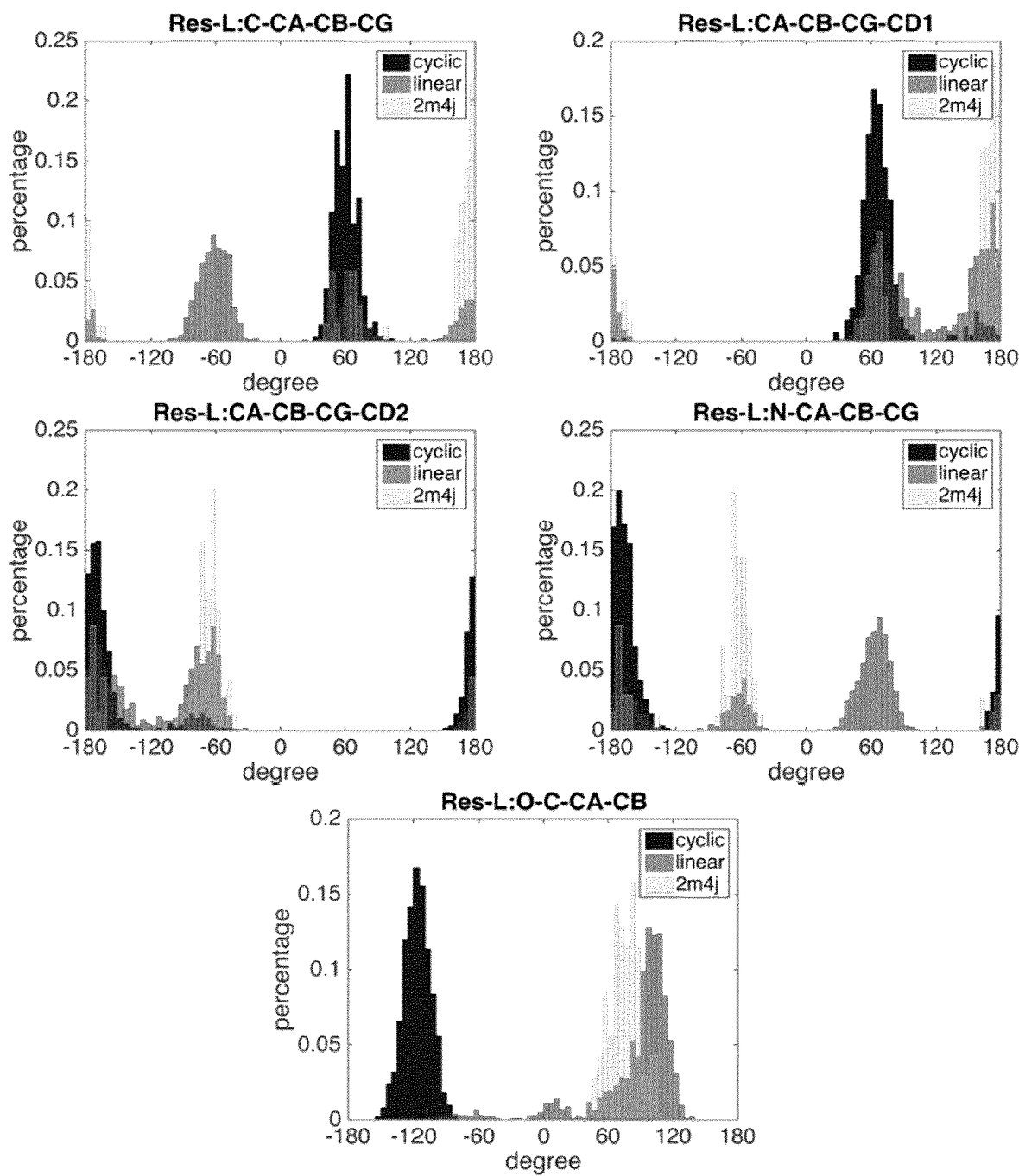
FIG. 6 is a graph showing dihedral angle distributions for angles involving the side chain heavy atoms of L17.
Figure 7:
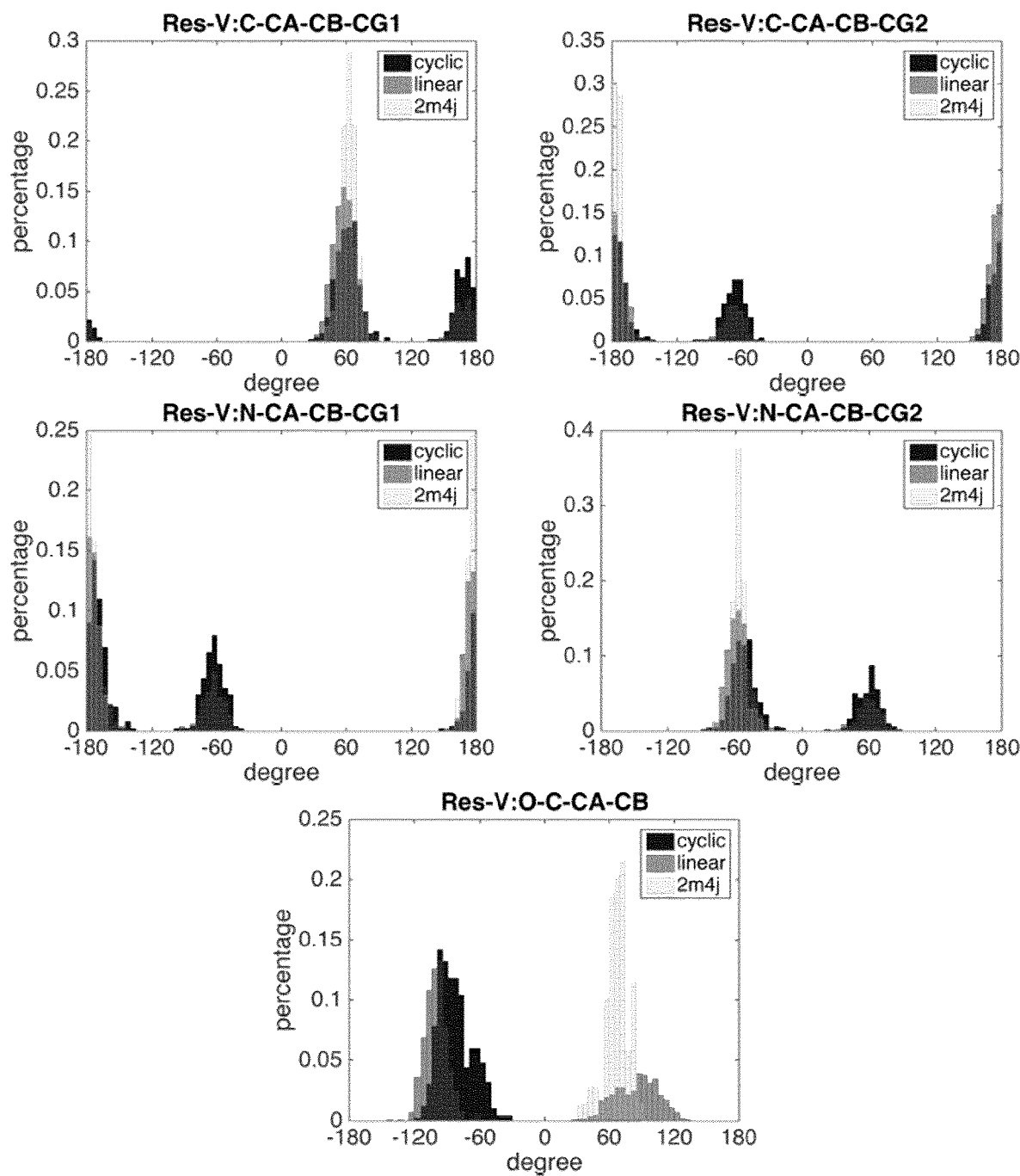
FIG. 7 is a graph showing dihedral angle distributions for angles involving the side chain heavy atoms of V18.
Figure 13:
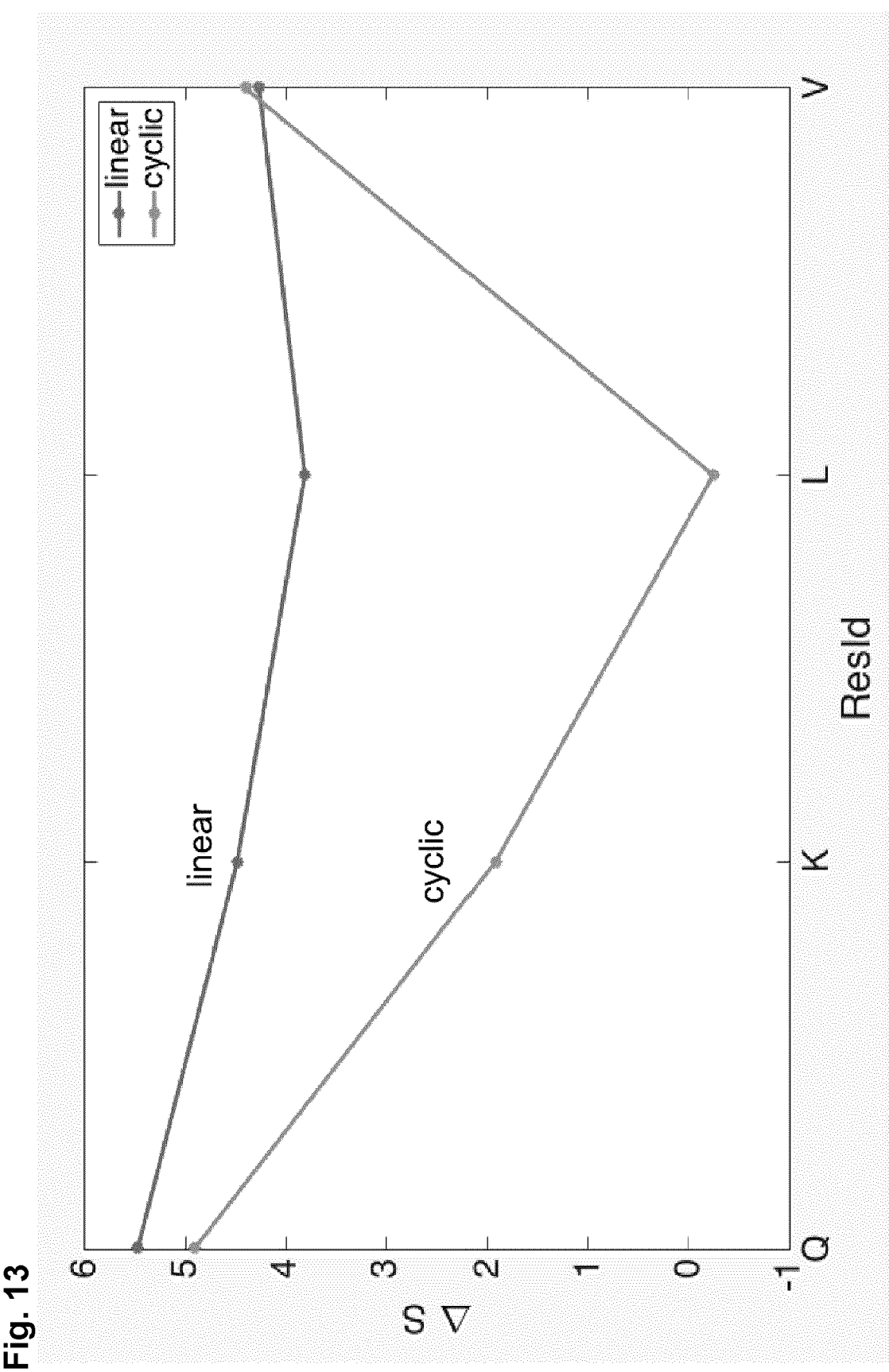
FIG. 13 is a graph showing the change in entropy for each of residues of QKLV (SEQ ID NO: 1), in the cyclic peptide Cyclo(CGQKLVG) (SEQ ID NO: 3) and linear peptide CGQKLVG (SEQ ID NO: 3), both as compared to the corresponding entropy of those residues in the fibril.
Figure 14:
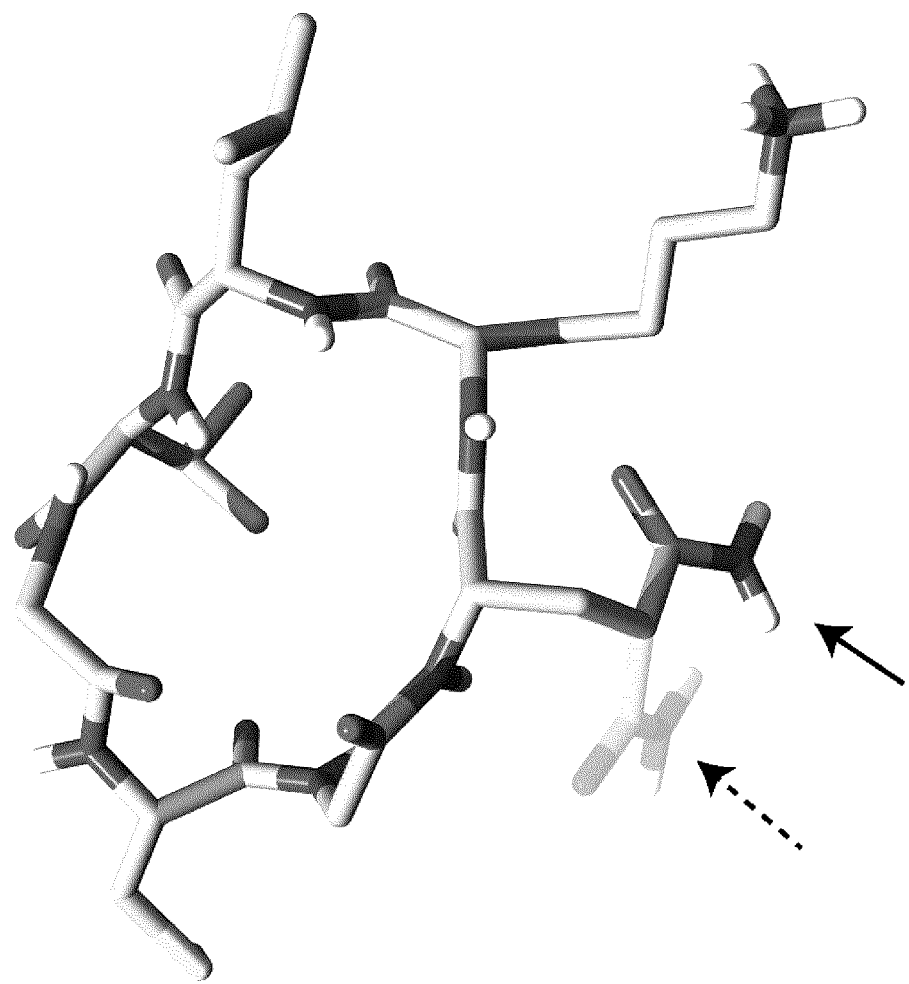
FIG. 14 is a schematic showing that the dihedral angle between the Cα-Cβ-Cγ-Cδ atoms in the side chain of Q is different between the cyclic peptide and the linear peptide.

The term "alternate conformation than occupied by Q, K, L and/or V in the linear A-beta peptide, A-beta monomer and/or fibril" or as used herein means having one or more differing conformational properties selected from solvent accessibility, entropy, curvature (e.g. in the context of peptide QKLV (SEQ ID NO: 1)), and one or more dihedral angles compared to said property for Q in linear unstructured A-beta peptide, A-beta monomer and/or A-beta fibril as shown for example in PDB 2MJ4 and shown in FIG. 14. FIG. 4A shows alternate conformational distributions compared to either the monomer or fibril for residue Q. FIGS. 5 and 6 show alternate similar conformational distributions for residues K and L respectively and that K and L can be differentiated from both the fibril and monomer. The alternate conformation can be similarly, less or more "constrained" than the comparator conformation. For example FIG. 13 demonstrates that Q, K and L in the cyclic compound described are more constrained than in the A-beta monomer.

The term "amino acid" includes all of the naturally occurring amino acids as well as modified L-amino acids. The atoms of the amino acid can for example include different isotopes. For example, the amino acids can comprise deuterium substituted for hydrogen nitrogen-15 substituted for nitrogen-14, and carbon-13 substituted for carbon-12 and other similar changes.

The term "antibody" as used herein is intended to include, monoclonal antibodies, polyclonal antibodies, single chain, veneered, humanized and other chimeric antibodies and binding fragments thereof, including for example a single chain Fab fragment, Fab'2 fragment or single chain Fv fragment. "Tissue culture supernatant clone" referred to herein refers to monoclonal antibody secreted by a hybridoma into the supernatant for collection and study. The antibody may be from recombinant sources and/or produced in animals such as rabbits, llamas, sharks etc. Also included are human antibodies that can be produced in transgenic animals or using biochemical techniques or can be isolated from a library such as a phage library. Humanized or other chimeric antibodies may include sequences from one or more than one isotype or class or species.

The phrase "isolated antibody" refers to antibody produced in vivo or in vitro that has been removed from the source that produced the antibody, for example, an animal, hybridoma or other cell line (such as recombinant insect, yeast or bacterial cells that produce antibody). The isolated antibody is optionally "purified", which means at least: 80%, 85%, 90%, 95%, 98% or 99% purity The term "binding fragment" as used herein to a part or portion of an antibody or antibody chain comprising fewer amino acid residues than an intact or complete antibody or antibody chain and which binds the antigen or competes with intact antibody. Exemplary binding fragments include without limitations Fab, Fab', F(ab')2, scFv, dsFv, ds-scFv, dimers, nanobodies, minibodies, diabodies, and multimers thereof. Fragments can be obtained via chemical or enzymatic treatment of an intact or complete antibody or antibody chain. Fragments can also be obtained by recombinant means. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, dsFv, ds-scFv, dimers, minibodies, diabodies, bispecific antibody fragments and other fragments can also be constructed by recombinant expression techniques.

The terms "IMGT numbering" or "ImMunoGeneTics database numbering", which are recognized in the art, refer to a system of numbering amino acid residues which are more variable (i.e. hypervariable) than other amino acid residues in the heavy and light chain variable regions of an antibody, or antigen binding portion thereof.

When an antibody is said to specifically bind to an epitope such as QKLV (SEQ ID NO: 1), what is meant is that the antibody specifically binds to a peptide containing the specified residues or a part thereof for example at least 2 residues of QKLV with a minimum affinity, and does not bind an unrelated sequence or unrelated sequence spatial orientation greater than for example an isotype control antibody. Such an antibody does not necessarily contact each residue of QKLV (SEQ ID NO: 1) and every single amino acid substitution or deletion within said epitope does not necessarily significantly affect and/or equally affect binding affinity.

When an antibody is said to selectively bind an epitope such as a conformational epitope, such as QKLV (SEQ ID NO: 1), what is meant is that the antibody preferentially binds one or more particular conformations containing the specified residues or a part thereof with greater affinity than it binds said residues in another conformation. For example, when an antibody is said to selectively bind a cyclopeptide comprising QKLV or related epitope relative to a corresponding linear peptide, the antibody binds the cyclopeptide with at least a 2 fold greater affinity than it binds the linear peptide.

As used herein, the term "conformational epitope" refers to an epitope where the amino acid sequence has a particular three-dimensional structure wherein an aspect of the three-dimensional structure not present in a corresponding linear unstructured epitope sequence is recognized by the cognate antibody. Antibodies which specifically bind a conformation-specific epitope recognize the spatial arrangement of one or more of the amino acids of that conformation-specific epitope. For example a QKLV (SEQ ID NO: 1) conformational epitope, refers to an epitope that is recognized by antibodies selectively, as compared to antibodies raised using linear QKLV (SEQ ID NO: 1). Antibodies which specifically and/or selectively bind a conformational epitope recognize the spatial arrangement of one or more of the amino acids of the epitope sequence specifically and/or selectively. For example a QKLV (SEQ ID NO: 1) conformational epitope, refers to an epitope of QKLV (SEQ ID NO: 1) that is recognized by antibodies specifically and/or selectively, for example at least 2 fold, 3 fold, 5 fold, 10 fold, 50 fold, 100 fold, 250 fold, 500 fold or 1000 fold or greater, more selectively as compared to a corresponding linear QKLV (SEQ ID NO: 1) compound.

The term "constrained conformation" as used herein with respect to an amino acid or a side chain thereof, within a sequence of amino acids, or with respect to a sequence of amino acids in a larger polypeptide, means decreased rotational mobility of the amino acid dihedral angles, relative to a corresponding linear peptide sequence, or the sequence or larger polypeptide, resulting in a decrease in the number of permissible conformations. This can be quantified for example by finding the entropy reduction for the ensemble of dihedral angle degrees of freedom, and is plotted in FIG. 13 for QKLV (SEQ ID NO: 1). For example, if the side chains in the sequence have less conformational freedom than the linear peptide, the entropy will be reduced. Such conformational restriction would enhance the conformational selectivity of antibodies specifically raised to this antigen. The term "more constrained conformation" as used herein means that the dihedral angle distribution (ensemble of allowable dihedral angles) of one or more dihedral angles is at least 10% more constrained than in the comparator conformation, as determined for example by the entropy of the amino acids Q, K, L, and/or V. Specifically, the average entropy change relative to the entropy in the fibril, S(constrained)—S(fibril), of QKLV (SEQ ID NO: 1) in the more constrained conformational ensemble is on average reduced by more than 10% or reduced by more than 20% or reduced by more than 30% or reduced by more than 40%, from the unconstrained conformational ensemble, e.g. of the quantity S(linear)—S(fibril) for the linear peptide (FIG. 13 plots this entropy reduction).

The term "related epitope" as used herein means at least two residues of QKLV (SEQ ID NO: 1), optionally KL, that are antigenic, and/or sequences comprising up to 1 or up to 2 amino acid residues in a A-beta either N-terminal and/or C-terminal to at least two residues of QKLV (SEQ ID NO: 1) (e.g. QKLVF (SEQ ID NO: 10). Exemplary related epitopes can include A-beta sequences shown in SEQ ID NO: 1, 2, 9 and 10.

The term "no or negligible plaque binding" or "lacks or has negligible plaque binding" as used herein with respect to an antibody means that the antibody does not show typical plaque morphology staining on immunohistochemistry (e.g. in situ) and the level of staining is comparable to or no more than 2 fold the level seen with an IgG negative (e.g. irrelevant) isotype control.

The term "Isolated peptide" refers to peptide that has been produced, for example, by recombinant or synthetic techniques, and removed from the source that produced the peptide, such as recombinant cells or residual peptide synthesis reactants. The isolated peptide is optionally "purified", which means at least: 80%, 85%, 90%, 95%, 98% or 99% purity and optionally pharmaceutical grade purity.

The term "detectable label" as used herein refers to moieties such as peptide sequences (such a myc tag, HA-tag, V5-tag or NE-tag), fluorescent proteins that can be appended or introduced into a peptide or compound described herein and which is capable of producing, either directly or indirectly, a detectable signal. For example, the label may be radio-opaque, positron-emitting radionuclide (for example for use in PET imaging), or a radioisotope, such as $^3$H, $^{13}$N, $^{14}$C, $^{18}$F, $^{32}$P, $^{35}$S, $^{123}$I, $^{125}$I, $^{131}$I; a fluorescent (fluorophore) or chemiluminescent (chromophore) compound, such as fluorescein isothiocyanate, rhodamine or luciferin; an enzyme, such as alkaline phosphatase, beta-galactosidase or horseradish peroxidase; an imaging agent; or a metal ion.

The detectable label may be also detectable indirectly for example using secondary antibody.

The term "epitope" as commonly used means an antibody binding site, typically a polypeptide segment, in an antigen that is specifically recognized by the antibody. As used herein "epitope" can also refer to the amino acid sequence or a part thereof identified on A-beta using the collective coordinates method described to which antibodies can be raised using a peptide comprising the epitope sequence. For example an antibody generated against an isolated peptide corresponding to a cyclic compound comprising the identified target region QKLV (SEQ ID NO: 1), recognizes part or all of said "epitope" sequence. An epitope is "accessible" in the context of the present specification when it is accessible to binding by an antibody.

The term "greater affinity" as used herein refers to a relative degree of antibody binding where an antibody X binds to target Y more strongly ($K_{on}$) and/or with a smaller dissociation constant ($K_{off}$) than to target Z, and in this context antibody X has a greater affinity for target Y than for Z. Likewise, the term "lesser affinity" herein refers to a degree of antibody binding where an antibody X binds to target Y less strongly and/or with a larger dissociation constant than to target Z, and in this context antibody X has a lesser affinity for target Y than for Z. The affinity of binding between an antibody and its target antigen, can be expressed as $K_A$ equal to $1/K_D$ where $K_D$ is equal to $k_{on}/k_{off}$. The $k_{on}$ and $k_{off}$ values can be measured using surface plasmon resonance technology, for example using a Molecular Affinity Screening System (MASS-1) (Sierra Sensors GmbH, Hamburg, Germany). An antibody that is selective for a conformation presented in a cyclic compound optional a cyclic peptide for example has a greater affinity for the cyclic compound (e.g. cyclic peptide) compared to a corresponding sequence in linear form (e.g. the sequence non-cyclized).

Also as used herein, the term "immunogenic" refers to substances which elicit the production of antibodies, activate T-cells and other reactive immune cells directed against an antigenic portion of the immunogen.

The term "corresponding linear compound" with regard to a cyclic compound refers to a compound, optionally a peptide, comprising or consisting of the same sequence or chemical moieties as the cyclic compound but in linear (i.e. non-cyclized) form, for example having properties as would be present in solution of a linear peptide. For example, the corresponding linear compound can be the synthesized peptide that is not cyclized.

As used herein "specifically binds" in reference to an antibody means that the antibody recognizes an epitope sequence and binds to its target antigen with a minimum affinity. For example a multivalent antibody binds its target with a $K_D$ of at least 1e-6, at least 1e-7, at least 1e-8, at least 1e-9, or at least 1e-10. Affinities greater than at least 1e-8 may be preferred. An antigen binding fragment such as Fab fragment comprising one variable domain, may bind its target with a 10 fold or 100 fold less affinity than a multivalent interaction with a non-fragmented antibody.

The term "selectively binds" as used herein with respect to an antibody that selectively binds a form of A-beta (e.g. fibril, monomer or oligomer) or a cyclic compound means that the antibody binds the form with at least 2 fold, at least 3 fold, or at least 5 fold, at least 10 fold, at least 100 fold, at least 250 fold, at least 500 fold or at least 1000 fold or more greater affinity. Accordingly an antibody that is more selective for a particular conformation (e.g. oligomer) preferentially binds the particular form of A-beta with at least 2 fold etc., greater affinity compared to another form and/or a linear peptide.

The term "linker" as used herein means a chemical moiety that can be covalently linked to the peptide comprising QKLV (SEQ ID NO: 1) epitope peptide, optionally linked to QKLV (SEQ ID NO: 1) peptide N- and C-termini to produce a cyclic compound. The linker can comprise a spacer and/or one or more functionalizable moieties. The linker via the functionalizable moieties can linked to a carrier protein or an immunogen enhancing agent such as Keyhole Limpet Hemocyanin (KLH).

The term "spacer" as used herein means any non-immunogenic or poorly immunogenic chemical moiety that can be covalently-linked directly or indirectly to a peptide N- and C-termini to produce a cyclic compound of longer length than the peptide itself, for example the spacer can be linked to the N- and C-termini of a peptide consisting of QKLV (SEQ ID NO: 1) to produce a cyclic compound of longer backbone length than the QKLV (SEQ ID NO: 1) sequence itself. That is, the cyclic peptide with a spacer (for example of 3 amino acid residues) makes a larger closed circle than the cyclic peptide without a spacer. The spacer may include, but are not limited to, non-immunogenic moieties such as G, A, or PEG repeats, e.g. GQKLV (SEQ ID NO: 4), GQKLVG (SEQ ID NO: 5), GGQKLVG (SEQ ID NO: 6), GQKLVGG (SEQ ID NO: 7), etc. (see FIG. 12 for specific embodiments). The spacer may comprise or be coupled to one or more functionalizing moieties, such as one or more cysteine (C) residues, which can be interspersed within the spacer or covalently linked to one or both ends of the spacer. Where a functionalizable moiety such as a C residue is covalently linked to one or more termini of the spacer, the spacer is indirectly covalently linked to the peptide. The spacer can also comprise the functionalizable moiety in a spacer residue as in the case where a biotin molecule is introduced into an amino acid residue.

The term "functionalizable moiety" as used herein refers to a chemical entity with a "functional group" which as used herein refers to a group of atoms or a single atom that will react with another group of atoms or a single atom (so called "complementary functional group") to form a chemical interaction between the two groups or atoms. In the case of cysteine, the functional group can be —SH which can be reacted to form a disulfide bond. Accordingly the linker can for example be CCC. The reaction with another group of atoms can be covalent or a strong non-covalent bond, for example as in the case as biotin-streptavidin bonds, which can have Kd~1e-14. A strong non-covalent bond as used herein means an interaction with a Kd of at least 1e-9, at least 1e-10, at least 1e-11, at least 1e-12, at least 1e-13 or at least 1e-14.

Proteins and/or other agents may be functionalized (e.g. coupled) to the cyclic peptide, either to aid in immunogenicity, or to act as a probe in in vitro studies. For this purpose, any functionalizable moiety capable of reacting (e.g. making a covalent or non-covalent but strong bond) may be used. In one specific embodiment, the functionalizable moiety is a cysteine residue which is reacted to form a disulfide bond with an unpaired cysteine on a protein of interest, which can be, for example, an immunogenicity enhancing agent such as Keyhole limpet hemocyanin (KLH), or a carrier protein such as Bovine serum albumin (BSA) used for in vitro immunoblots or immunohistochemical assays.

The term "reacts with" as used herein generally means that there is a flow of electrons or a transfer of electrostatic charge resulting in the formation of a chemical interaction.

The term "animal" or "subject" as used herein includes all members of the animal kingdom including mammals, optionally including or excluding humans.

A "conservative amino acid substitution" as used herein, is one in which one amino acid residue is replaced with another amino acid residue without abolishing the protein's desired properties. Suitable conservative amino acid substitutions can be made by substituting amino acids with similar hydrophobicity, polarity, and R-chain length for one another. Examples of conservative amino acid substitution include:

| Conservative Substitutions | |
| --- | --- |
| Type of Amino Acid | Substitutable Amino Acids |
| Hydrophilic | Ala, Pro, Gly, Glu, Asp, Gln, Asn, Ser, Thr |
| Sulphydryl | Cys |
| Aliphatic | Val, Ile, Leu, Met |
| Basic | Lys, Arg, His |
| Aromatic | Phe, Tyr, Trp |

The term "sequence identity" as used herein refers to the percentage of sequence identity between two polypeptide sequences or two nucleic acid sequences. To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions.times.100%). In one embodiment, the two sequences are the same length. The determination of percent identity between two sequences can also be accomplished using a mathematical algorithm. A preferred, non-limiting example of a mathematical algorithm utilized for the comparison of two sequences is the algorithm of Karlin and Altschul, 1990, Proc. Natl. Acad. Sci. U.S.A. 87:2264-2268, modified as in Karlin and Altschul, 1993, Proc. Natl. Acad. Sci. U.S.A. 90:5873-5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences homologous to a nucleic acid molecules of the present application. BLAST protein searches can be performed with the XBLAST program parameters set, e.g., to score-50, wordlength=3 to obtain amino acid sequences homologous to a protein molecule described herein. To obtain gapped alignments for comparison purposes, Gapped BLAST can be utilized as described in Altschul et al., 1997, Nucleic Acids Res. 25:3389-3402. Alternatively, PSI-BLAST can be used to perform an iterated search which detects distant relationships between molecules (Id.). When utilizing BLAST, Gapped BLAST, and PSI-Blast programs, the default parameters of the respective programs (e.g., of XBLAST and NBLAST) can be used (see, e.g., the NCBI website). Another preferred, non-limiting example of a mathematical algorithm utilized for the comparison of sequences is the algorithm of Myers and Miller, 1988, CABIOS 4:11-17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. The percent identity between two sequences can be determined using techniques similar to those described above, with or without allowing gaps. In calculating percent identity, typically only exact matches are counted.

For antibodies, percentage sequence identities can be determined when antibody sequences maximally aligned by IMGT or other (e.g. Kabat numbering convention). After alignment, if a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage.

The term "nucleic acid sequence" as used herein refers to a sequence of nucleoside or nucleotide monomers consisting of naturally occurring bases, sugars and intersugar (backbone) linkages. The term also includes modified or substituted sequences comprising non-naturally occurring monomers or portions thereof. The nucleic acid sequences of the present application may be deoxyribonucleic acid sequences (DNA) or ribonucleic acid sequences (RNA) and may include naturally occurring bases including adenine, guanine, cytosine, thymidine and uracil. The sequences may also contain modified bases. Examples of such modified bases include aza and deaza adenine, guanine, cytosine, thymidine and uracil; and xanthine and hypoxanthine. The nucleic acid can be either double stranded or single stranded, and represents the sense or antisense strand. Further, the term "nucleic acid" includes the complementary nucleic acid sequences as well as codon optimized or synonymous codon equivalents. The term "isolated nucleic acid sequences" as used herein refers to a nucleic acid substantially free of cellular material or culture medium when produced by recombinant DNA techniques, or chemical precursors, or other chemicals when chemically synthesized. An isolated nucleic acid is also substantially free of sequences that naturally flank the nucleic acid (i.e. sequences located at the 5' and 3' ends of the nucleic acid) from which the nucleic acid is derived.

"Operatively linked" is intended to mean that the nucleic acid is linked to regulatory sequences in a manner which allows expression of the nucleic acid. Suitable regulatory sequences may be derived from a variety of sources, including bacterial, fungal, viral, mammalian, or insect genes. Selection of appropriate regulatory sequences is dependent on the host cell chosen and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector.

The term "vector" as used herein comprises any intermediary vehicle for a nucleic acid molecule which enables said nucleic acid molecule, for example, to be introduced into prokaryotic and/or eukaryotic cells and/or integrated into a genome, and include plasmids, phagemids, bacteriophages or viral vectors such as retroviral based vectors, Adeno Associated viral vectors and the like. The term "plasmid" as used herein generally refers to a construct of extrachromosomal genetic material, usually a circular DNA duplex, which can replicate independently of chromosomal DNA.

By "at least moderately stringent hybridization conditions" it is meant that conditions are selected which promote selective hybridization between two complementary nucleic acid molecules in solution. Hybridization may occur to all or a portion of a nucleic acid sequence molecule. The hybridizing portion is typically at least 15 (e.g. 20, 25, 30, 40 or 50) nucleotides in length. Those skilled in the art will recognize that the stability of a nucleic acid duplex, or hybrids, is determined by the Tm, which in sodium containing buffers is a function of the sodium ion concentration and temperature (Tm=81.5° C.−16.6 (Log 10 [Na+])+0.41(%(G+C)−600/I), or similar equation). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example if nucleic acid molecules are sought that have a >95% identity, the final wash temperature will be reduced by about 5° C. Based on these considerations those skilled in the art will be able to readily select appropriate hybridization conditions. In preferred embodiments, stringent hybridization conditions are selected. By way of example the following conditions may be employed to achieve stringent hybridization: hybridization at 5× sodium chloride/sodium citrate (SSC)/5×Denhardt's solution/1.0% SDS at Tm−5° C. based on the above equation, followed by a wash of 0.2× SSC/0.1% SDS at 60° C. Moderately stringent hybridization conditions include a washing step in 3× SSC at 42° C. It is understood, however, that equivalent stringencies may be achieved using alternative buffers, salts and temperatures. Additional guidance regarding hybridization conditions may be found in: Current Protocols in Molecular Biology, John Wiley & Sons, N.Y., 2002, and in: Sambrook et al., Molecular Cloning: a Laboratory Manual, Cold Spring Harbor Laboratory Press, 2001.

The term "treating" or "treatment" as used herein and as is well understood in the art, means an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, diminishment of the reoccurrence of disease, and remission (whether partial or total), whether detectable or undetectable. "Treating" and "Treatment" can also mean prolonging survival as compared to expected survival if not receiving treatment. "Treating" and "treatment" as used herein also include prophylactic treatment. For example, a subject with early stage AD can be treated to prevent progression can be treated with a compound, antibody, immunogen, nucleic acid or composition described herein to prevent progression.

The term "administered" as used herein means administration of a therapeutically effective dose of a compound or composition of the disclosure to a cell or subject.

As used herein, the phrase "effective amount" means an amount effective, at dosages and for periods of time necessary to achieve a desired result. Effective amounts when administered to a subject may vary according to factors such as the disease state, age, sex, weight of the subject. Dosage regime may be adjusted to provide the optimum therapeutic response.

The term "pharmaceutically acceptable" means that the carrier, diluent, or excipient is compatible with the other components of the formulation and not substantially deleterious to the recipient thereof.

Compositions or methods "comprising" or "including" one or more recited elements may include other elements not specifically recited. For example, a composition that "comprises" or "includes" an antibody may contain the antibody alone or in combination with other ingredients.

In understanding the scope of the present disclosure, the term "consisting" and its derivatives, as used herein, are intended to be close ended terms that specify the presence of stated features, elements, components, groups, integers, and/or steps, and also exclude the presence of other unstated features, elements, components, groups, integers and/or steps.

The recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about." Further, it is to be understood that "a," "an," and the include plural referents unless the content clearly dictates otherwise. The term "about" means plus or minus 0.1 to 50%, 5-50%, or 10-40%, preferably 10-20%, more preferably 10% or 15%, of the number to which reference is being made.

Further, the definitions and embodiments described in particular sections are intended to be applicable to other embodiments herein described for which they are suitable as would be understood by a person skilled in the art. For example, in the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

The singular forms of the articles "a," "an," and "the" include plural references unless the context clearly dictates otherwise. For example, the term "a compound" or "at least one compound" can include a plurality of compounds, including mixtures thereof.

II. Epitopes and Binding Proteins

The inventors have identified an epitope in A-beta, QKLV (SEQ ID NO: 1) at amino acids 15 to 18 on A-beta. They have further identified that the epitope or a part thereof may be a conformational epitope, and that QKLV (SEQ ID NO: 1) may be selectively accessible to antibody binding in oligomeric species of A-beta.

Without wishing to be bound by theory, fibrils may present interaction sites that have a propensity to catalyze oligomerization. This may be strain-specific, and may only occur when selective fibril surface not present in normal patients is exposed and thus able to have aberrant interactions with the monomer (i.e. is presented to the monomer). Environmental challenges such as low pH, osmolytes present during inflammation, or oxidative damage may induce disruption in fibrils that can lead to exposure of more weakly stable regions. There is of interest, then, to predict these weakly-stable regions, and use such predictions to rationally design antibodies that could target them. Regions likely to be disrupted in the fibril may also be good candidates for exposed regions in oligomeric species.

Computer based systems and methods to predict contiguous protein regions that are prone to disorder are described in U.S. Patent Application Ser. No. 62/253,044, SYSTEMS AND METHODS FOR PREDICTING MISFOLDED PROTEIN EPITOPES BY COLLECTIVE COORDINATE BIASING filed Nov. 9, 2015 and U.S. patent application Ser. No. 12/574,637, "Methods and Systems for Predicting Misfolded Protein Epitopes" filed Oct. 6, 2009, each of which are hereby incorporated by reference in their entirety. As described in the Examples, the methods were applied to A-beta and identified an epitope that may be more accessible in A-beta oligomers.

As described in the Examples, a cyclic peptide cyclo (CGQKLVG) (SEQ ID NO: 3) may capture the conformational differences of the epitope in oligomers relative to the monomer and/or fibril species. For example, differences in solvent accessible surface, curvature and the dihedral angle distributions for several of the dihedral angles in the cyclic 7-mer cyclo (CGQKLVG) (SEQ ID NO: 3) were found to be substantially different than in the A-beta monomer and fibril, suggesting that the cyclopeptide provides for a conformational epitope that is distinct from the linear unstructured epitope.

Antibodies raised using an immunogen comprising cyclo (CGQKLVG) (SEQ ID NO: 2) selectively bound cyclo (CGQKLVG) (SEQ ID NO: 2) over linear CGQKLVG (SEQ ID NO: 2) and selectively bound synthetic and/or native oligomeric A-beta species compared to monomeric A-beta and A-beta fibril plaques. Further, antibodies raised to cyclo (CGQKLVG) (SEQ ID NO: 2) were able to inhibit in vitro propagation of A-beta aggregation and inhibit A-beta oligomer induced toxicity in a neural cell model.

i) QKLV (SEQ ID NO: 1) "Epitope" Compounds

Accordingly, the present disclosure identifies a conformational epitope in A-beta consisting of amino acids QKLV (SEQ ID NO: 1), or a part thereof, which correspond to amino acids residues 15-18 on A-beta.

An aspect includes a compound comprising an A-beta peptide comprising or consisting of QKLV (SEQ ID NO: 1) or sequence of a related epitope and/or part of any of the foregoing.

In some embodiments, the A-beta peptide comprising QKLV (SEQ ID NO: 1) can include 1, 2 or 3 additional residues in A-beta N- and/or C-terminus of QKLV (SEQ ID NO: 1) for example HQKLV (SEQ ID NO: 2). The 3 amino acids N-terminal to QKLV (SEQ ID NO: 1) in A-beta are VHH and the 3 amino acids C-terminal to QKLV (SEQ ID NO: 1) are FFA. In an embodiment the A-beta peptide is a maximum of 7 amino acids, 6 amino acids or 5 amino acids.

In an embodiment, the A-beta peptide comprises one or two additional residues in A-beta that are C-terminal to QKLV (SEQ ID NO: 1).

In an embodiment, the compound comprises a sequence listed in Table 10.

In an embodiment, the compound further includes a linker. The linker comprises a spacer and/or one or more functionalizable moieties. The linker can for example comprise 3, 4, 5, 6, 7 or 8 amino acids and/or equivalently functioning molecules such as polyethylene glycol (PEG) moieties, and/or a combination thereof. In an embodiment, the spacer amino acids are selected from non-immunogenic or poorly immunogenic amino acid residues such as G and A, for example the spacer can be GGG, GAG, G(PEG)G, PEG-PEG-GG and the like. One or more functionalizable moieties e.g. amino acids with a functional group may be included for example for coupling the compound to an agent or detectable tag or a carrier such as BSA or an immunogenicity enhancing agent such as KLH.

In an embodiment the linker comprises GC-PEG, PEG-GC, GCG or PEG-C-PEG.

In an embodiment, the linker comprises 1, 2, 3, 4, 5, 6, 7 or 8 amino acids.

In embodiments wherein the A-beta peptide comprising QKLV (SEQ ID NO: 1) includes 1, 2 or 3 additional residues found in A-beta that are N- and/or C-terminal to QKLV (SEQ ID NO: 1) (e.g. HQKLV (SEQ ID NO: 2), the linker in the cyclized compound is covalently linked to the N- and/or C-termini of the A-beta residues (e.g. to residues H and V). The cyclic compound can be synthesized as a linear molecule with the linker covalently attached to the N-terminus or C-terminus of the peptide comprising QKLV (SEQ ID NO: 1) prior to cyclization. Alternatively part of the linker is covalently attached to the N-terminus and part is covalently attached to the C-terminus prior to cyclization. In either case, the linear compound is cyclized for example in a head to tail cyclization (e.g. amide bond cyclization).

Proteinaceous portions of compounds may be prepared by chemical synthesis using techniques well known in the chemistry of proteins such as solid phase synthesis or synthesis in homogenous solution.

In an embodiment, the compound is a cyclic compound. In an embodiment, the cyclic compound is a cyclic peptide (cyclopeptide).

Reference to the "cyclic peptide" herein can refer to a fully proteinaceous compound (e.g. wherein the linker is for example 1, 2, 3, 4, 5, 6, 7 or 8 amino acids). It is understood that properties described for the cyclic peptide determined in the examples can be incorporated in other compounds (e.g. cyclic compounds) comprising non-amino acid linker molecules.

An aspect therefore provides a cyclic compound comprising peptide QKLV (SEQ ID NO: 1) (e.g. A beta peptide) and a linker, wherein the linker is covalently coupled to the peptide comprising QKLV (SEQ ID NO: 1) (optionally the Q and the V residues when the peptide consists of QKLV (SEQ ID NO: 1)), optionally wherein at least Q is in an alternate conformation from Q in a linear peptide comprising QKLV (SEQ ID NO: 1), and/or the conformation of Q in the monomer and/or fibril, and optionally wherein at least Q, or at least K, or at least L is in a more constrained conformation in the cyclic compound than the conformation occupied in a linear peptide comprising QKLV (SEQ ID NO: 1) or a related epitope sequence.

The linear peptide comprising the A-beta sequence can be comprised in a linear compound. The linear compound or the linear peptide comprising QKLV (SEQ ID NO: 1) is in an embodiment, a corresponding linear peptide. In another embodiment, the linear peptide is any length of A-beta peptide comprising QKLV (SEQ ID NO: 1), including for example a linear peptide comprising A-beta residues 1-35, or smaller portions thereof such as A-beta residues 10-20, 11-20, 12-20, 13-20, 10-19, 10-18 and the like etc. The linear peptide can in some embodiments also be a full length A-beta peptide.

In an embodiment the cyclic compound comprises peptide comprising or consisting of QKLV (SEQ ID NO: 1) and a linker, wherein the linker is coupled to the N- and C-termini of the peptide (e.g. the Q and the V residues when the peptide consists of QKLV (SEQ ID NO: 1)). In an embodiment, at least Q is in an alternate conformation in the cyclic compound than occupied by Q in a linear peptide comprising QKLV (SEQ ID NO: 1). In an embodiment, at least Q is in an alternate conformation in the cyclic compound than occupied by Q in the monomer and/or fibril.

In an embodiment, the alternate conformation is a constrained conformation.

In an embodiment, at least Q, optionally alone or in combination with at least K, or at least L is in a more constrained conformation than the conformation occupied in a linear peptide comprising QKLV (SEQ ID NO: 1).

In an embodiment, the conformation of Q and/or Q in combination with one or more of K, L and/or V is comprised in the compound in an alternate conformation than that occupied in the linear peptide comprising QKLV, optionally in a more constrained conformation.

For example, the alternate conformation can include one or more differing dihedral angles in residues Q, and optionally in Q and/or K, and/or L and/or V differing from the dihedral angles in the linear peptide or peptide in the context of the fibril.

The alternate conformation can include for one or more amino acid side chains of the epitope, particularly for Q and also for K or L, an increase or decrease in the solvent accessible surface area (SASA) of one or more parts of the side chains relative to a linear peptide and/or A-beta fibril.

Figure 10:
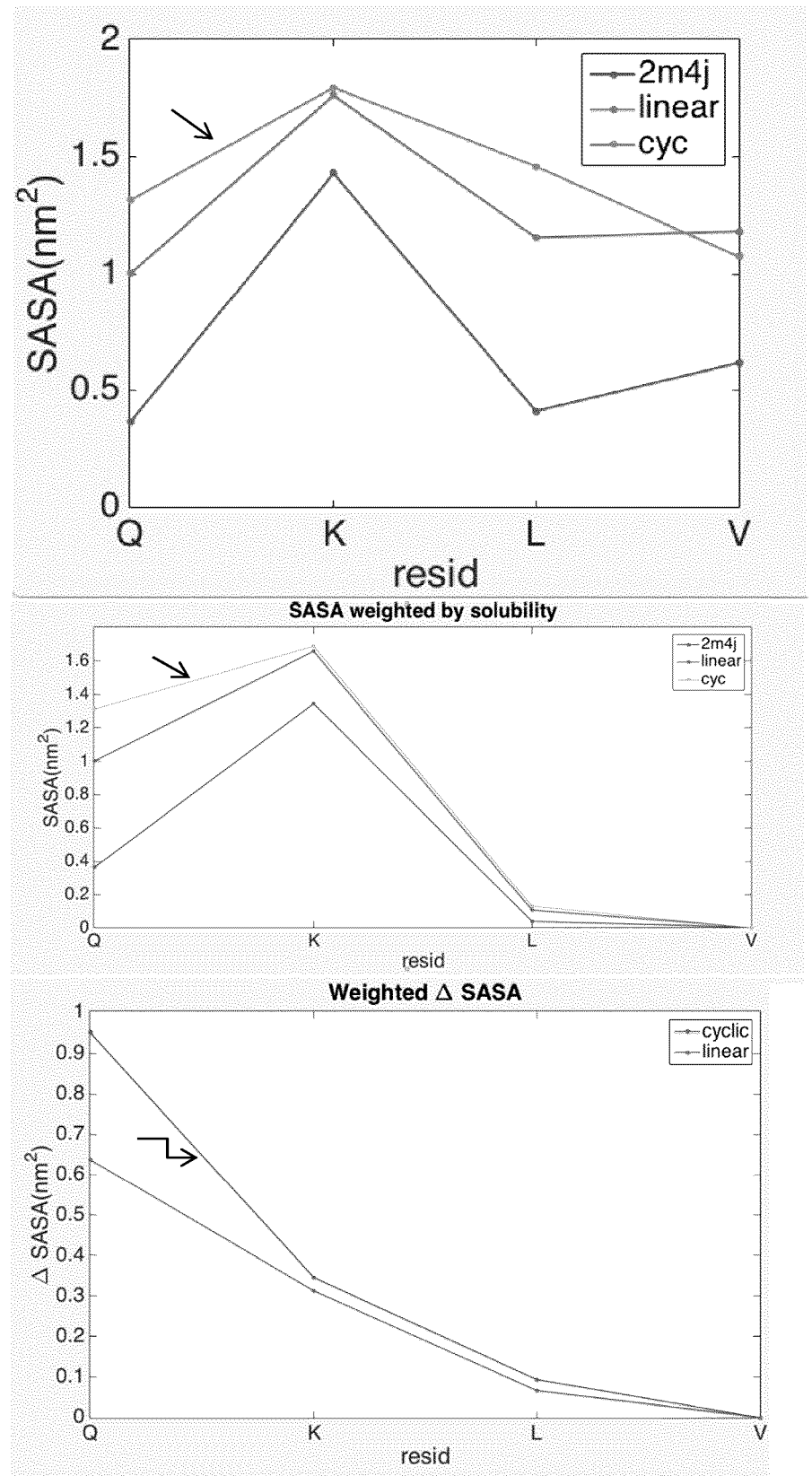
FIG. 10 is a series of plots of the solvent accessible surface area (SASA), the weighted SASA, $\sigma_i \cdot SASA_i$, and $\sigma_i \cdot SASA_i - (\sigma_i 19\ SASA_i)_{fibral}$. An arrow identifies the cyclic structure in each panel.
Figure 11:
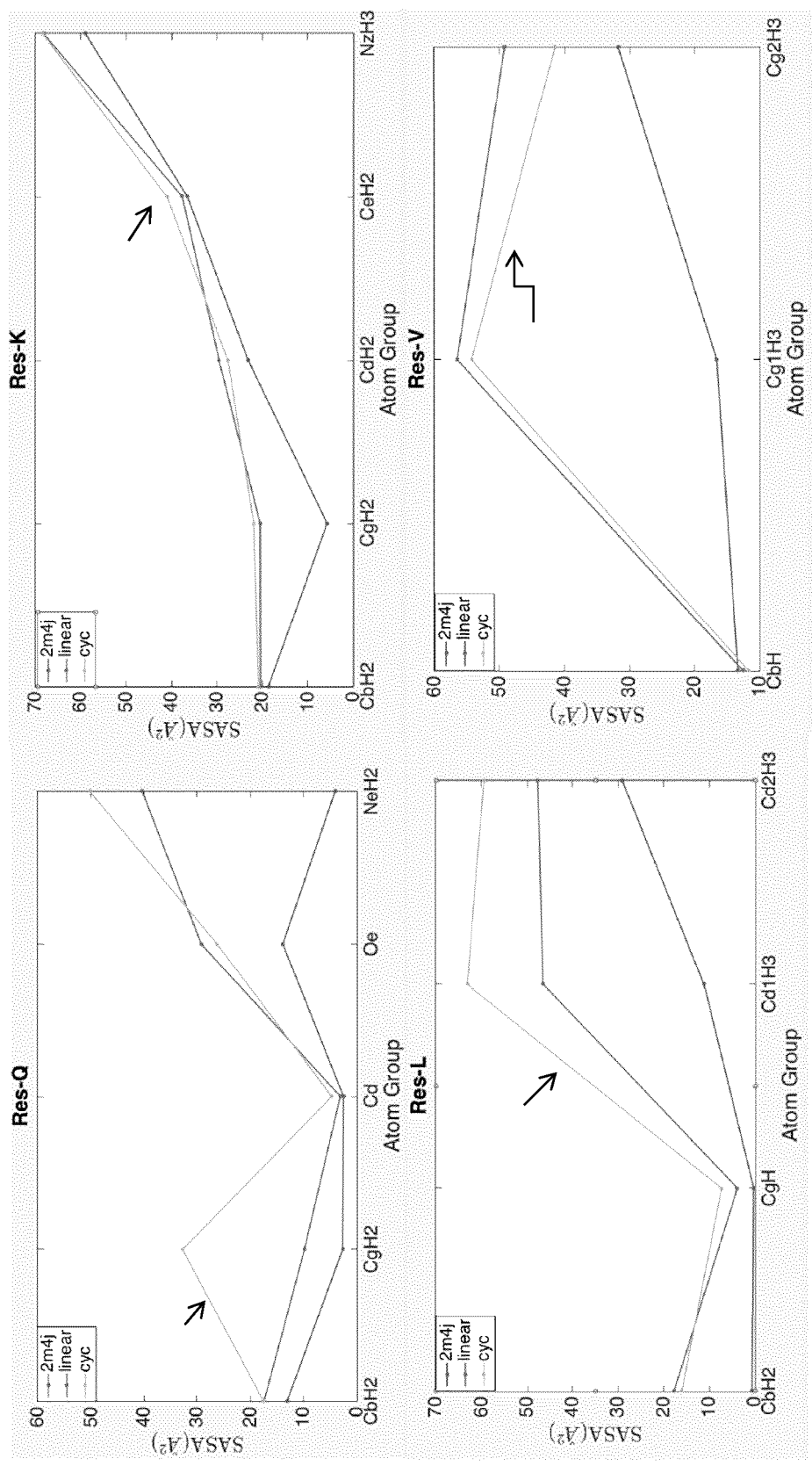
FIG. 11 shows plots of the SASA of heavy atom-hydrogen moieties along the side chains of residues QKLV (SEQ ID NO: 1). An arrow identifies the cyclic structure in each panel.

For example, FIG. 10 (top panel) and FIG. 11 show that the side chains of Q and L are more solvent-exposed in the cyclic compound than in the linear peptide due to the bowing of the backbone, which "splays out" the side chains. FIG. 11, which looks at the specific moieties on the side chains, demonstrates that the increase in SASA of Q comes from the $C_\gamma H_2$ group and/or the $N_\varepsilon H_2$ groups. Similarly it can be seen that the increase in SASA of L comes from $C_{\delta 1}H_3$ and/or $C_{\delta 2}H_3$.

In an embodiment, the SASA of Q, and optionally one or more of K or L in the compound is increased relative to the linear peptide QKLV (SEQ ID NO: 1).

The alternate conformation can also include an increase in curvature centered around an amino acid or of the cyclic peptide QKLV (SEQ ID NO: 1) relative to a linear peptide and/or A-beta fibril.

In an embodiment, the alternate conformation QKLV (SEQ ID NO: 1) has an increased curvature relative to linear QKLV (SEQ ID NO: 1). As shown in the Examples, the curvature of the cyclic epitope backbone is also increased relative to that in the linear peptide or peptide in the context of the fibril (FIG. 3) as described in Example 4.

The values of the curvature were determined for Q, K, L, V in cyclo(CGQKLVG) (SEQ ID NO: 3), linear CGQKLVG (SEQ ID NO: 3), and QKLV (SEQ ID NO: 1) in the context of the fibril. As described in Example 4, these were:
Cyclic peptide: 1.248 1.566 1.422 1.46
Linear Peptide: 0.870 1.355 0.931 1.303
Fibril: 0.740 1.159 0.796 1.188
The averages of these are:
Cyclic peptide: 1.42
Linear peptide: 1.11
Fibril: 0.97

Accordingly, the curvature of the Q, and/or one or more of K, L and/or V in the alternate conformation is increased by at least 0.1, 0.2, 0.3 or more radians compared to the linear peptide.

In an embodiment, the QK, QKL and/or QKLV (SEQ ID NO: 1) are in an alternate conformation, for example as compared to what is occupied by these residues in a non-oligomeric conformation.

For example for Q and K, the SASA weighted by the solubility is increased in the cyclic peptide relative to the linear peptide or peptide in fibril.

Further the entropy of the side chains is reduced in the cyclic peptide relative to the linear peptide, rendering the side chains in a more structured conformation than the linear peptide.

Conformations preferred in the cyclic compound are different from the conformations preferred in either the linear peptide or fibril. Specifically, the dihedral angle between the Cα-Cβ-Cγ-Cδ atoms in the side chain of Q is different between the cyclic peptide and the linear peptide. This is depicted in FIG. 14, as well as in FIGS. 4, 5, and 6.

In FIG. 14, the solid arrow indicates the dihedral angle typically occupied in the cyclic peptide, and the dashed arrow indicates the dihedral angle typically occupied in the linear peptide, with that portion of the side chain shown as semi-transparent.

Figure 3:
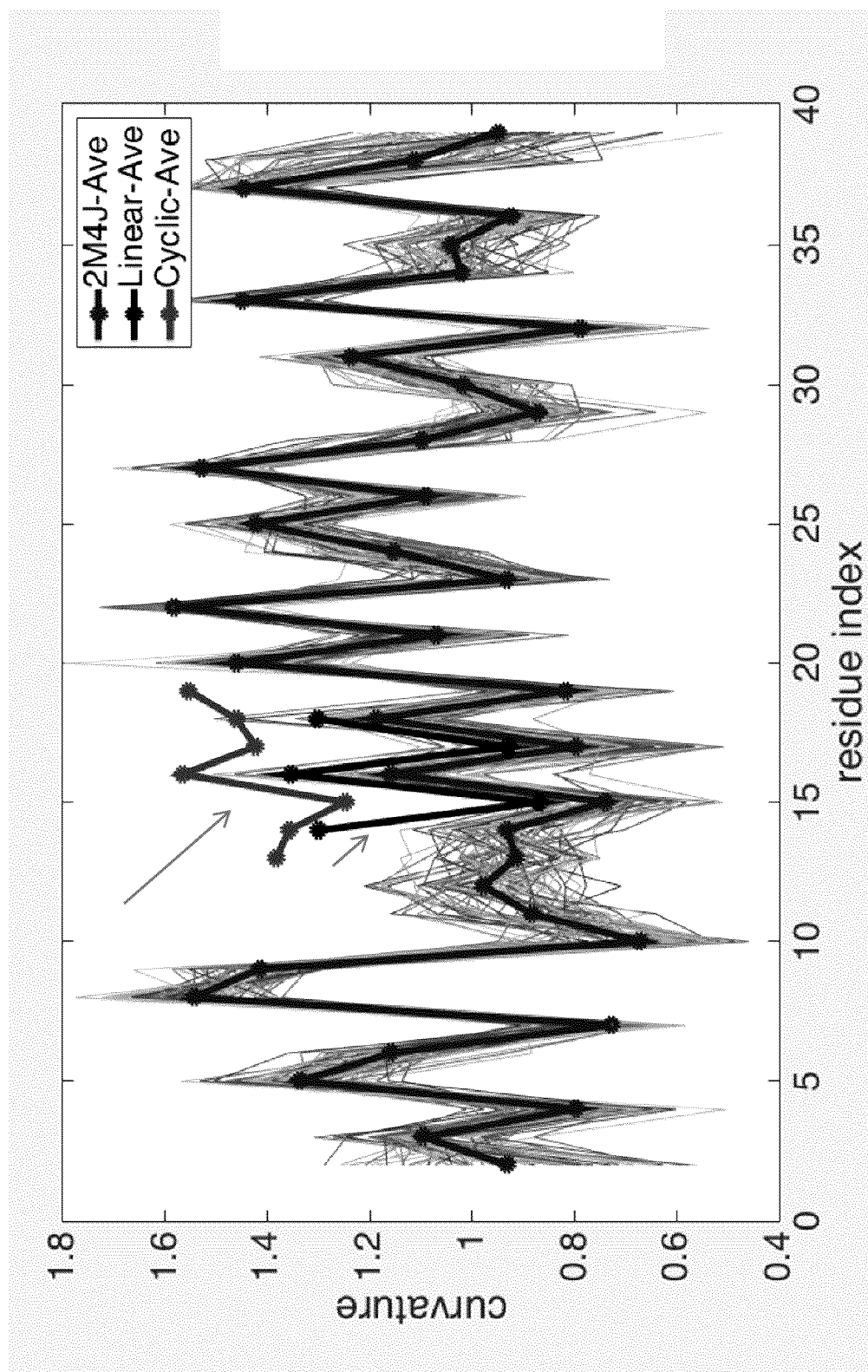
FIG. 3 is a schematic showing curvature as a function of residue index. The long arrow identifies the cyclic peptide and the short arrow identifies the linear peptide.

As demonstrated herein, the curvature of the cyclic epitope is increased relative that in the linear peptide or to the peptide in the context of the fibril (FIG. 3). It is also demonstrated, that one or more of the dihedral angles in residues Q, and/or K, and/or L and/or V are significantly different from the dihedral angles in the linear peptide or peptide in the context of the fibril. Further, for one or more amino acids of the epitope, particularly Q and K, the solvent accessible surface area (SASA) of side chains are increased in the cyclic peptide as compared to the peptide in the context of the fibril. For these amino acids, the SASA weighted by the solubility is increased in the cyclic peptide relative to the peptide in fibril. In addition, the entropy of the side chains is reduced in the cyclic peptide relative to the linear peptide, rendering the side chains in a more structured conformation than the linear peptide (FIG. 13).

Cyclic compounds which show similar changes are also encompassed.

The cyclic compound in some embodiments that comprises a peptide comprising QKLV (SEQ ID NO: 1) can include 1, 2, 3 or more residues in A-beta upstream and/or downstream of QKLV (SEQ ID NO: 1). In such cases the spacer is covalently linked to the N- and C-termini of the A-beta residues.

Figure 12:
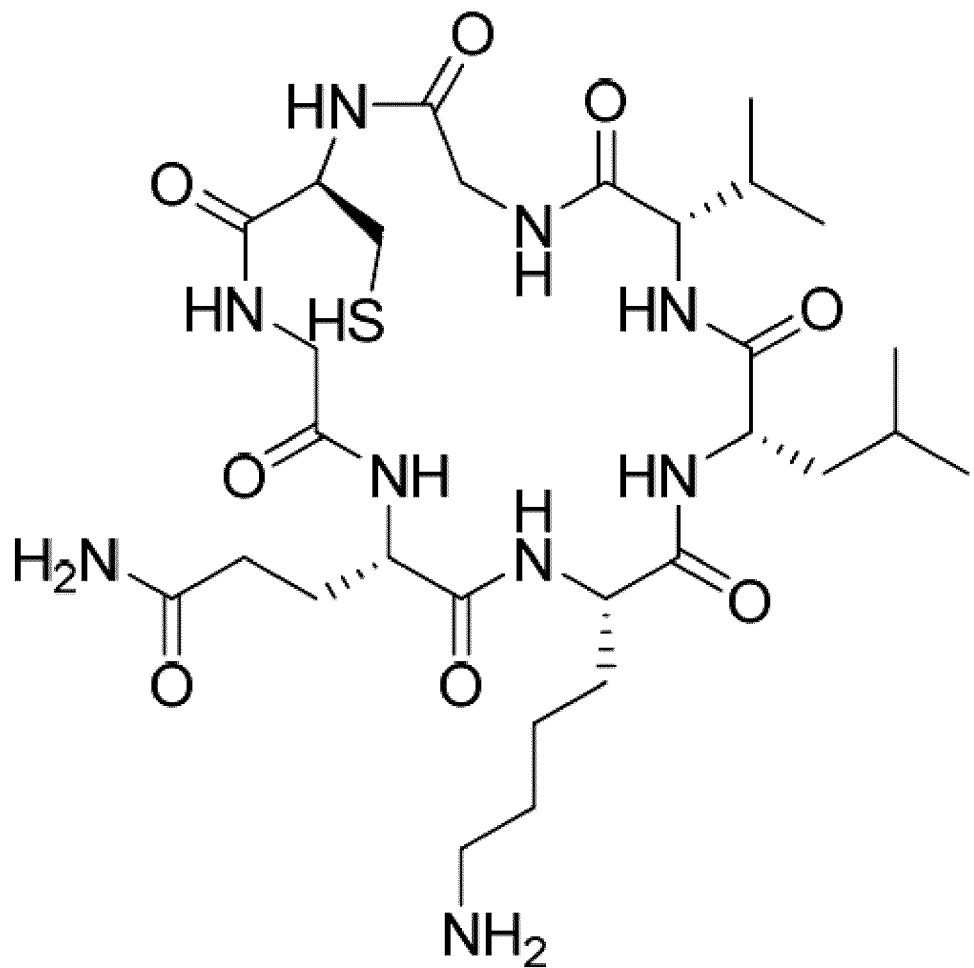
FIG. 12 is a schematic showing a series of cyclic compounds comprising QKLV (SEQ ID NO: 1).
Figure 12:
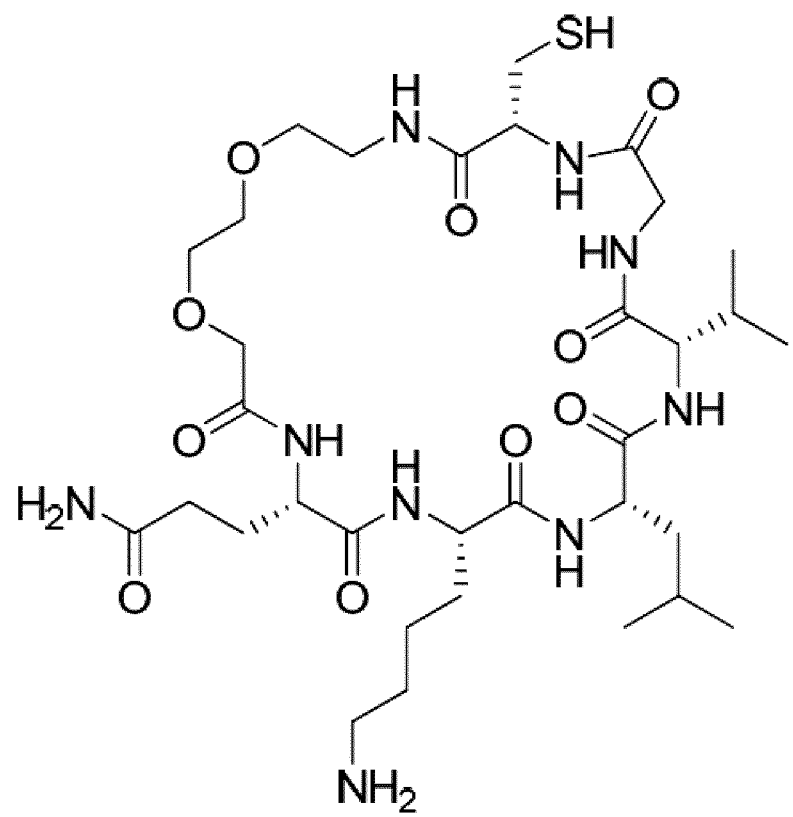
Figure 12:
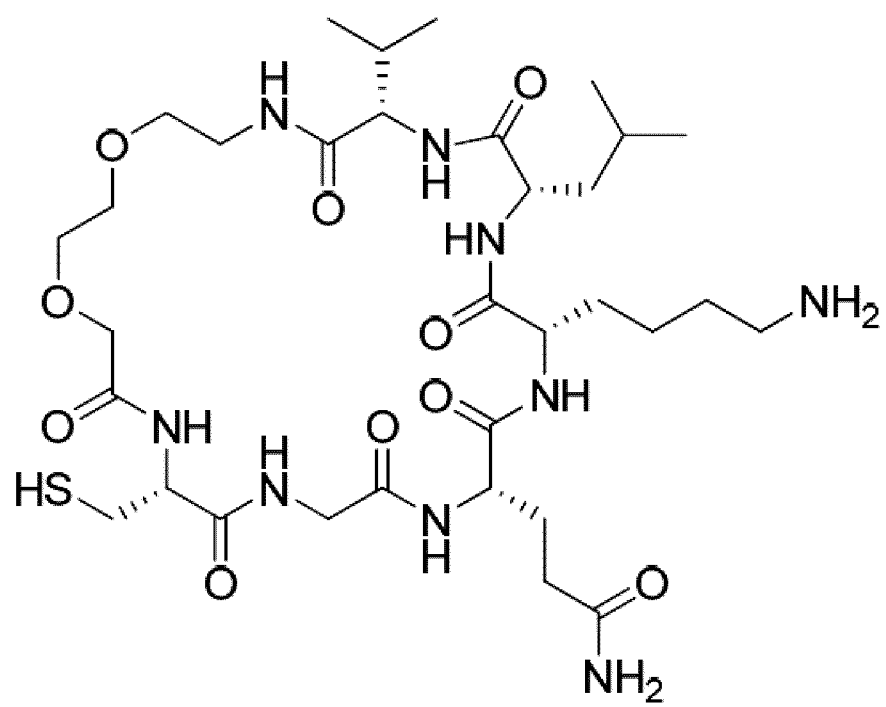

In an embodiment, the cyclic compound is a compound in FIG. 12.

Methods for making cyclized peptides are known in the art and include SS-cyclization or amide cyclization (head-to-tail, or backbone cyclization). Methods are further described in Example 5. For example, a peptide with "C" residues at its N- and C-termini, e.g. CGQKLVGC (SEQ ID NO: 8), can be reacted by SS-cyclization to produce a cyclic peptide.

The cyclic compound can be synthesized as a linear molecule with the linker covalently attached to the N-terminus or C-terminus of the peptide comprising the A-beta peptide, prior to cyclization. Alternatively part of the linker is covalently attached to the N-terminus and part is covalently attached to the C-terminus prior to cyclization. In either case, the linear compound is cyclized for example in a head to tail cyclization (e.g. amide bond cyclization).

In some embodiments, the linker or spacer is indirectly coupled to the N- and C-terminus residues of the A-beta peptide.

As described in Example 4, the cyclic compound of FIG. 12A was assessed for its relatedness to the conformational epitope identified. The cyclic compound comprising QKLV (SEQ ID NO: 1) peptide for example can be used to raise antibodies selective for one or more conformations.

The epitope QKLV (SEQ ID NO: 1) and/or a part thereof, as described herein may be a potential target in misfolded propagating strains of A-beta involved in A-beta, and antibodies that recognize the conformational epitope may for example be useful in detecting such propagating strains.

Also provided in another aspect is an isolated peptide comprising an A-beta peptide sequence described herein, including linear peptides and cyclic peptides. Linear peptides can for example be used for selecting antibodies for lack of binding thereto. The isolated peptide can comprise a linker sequence described herein. The linker can be covalently coupled to the N or C terminus or may be partially coupled to the N terminus and partially coupled to the C terminus as in CGQKLVG (SEQ ID NO: 3) linear peptide. In the cyclic peptide, the linker is coupled to the C-terminus and N-terminus directly or indirectly.

Another aspect includes an immunogen comprising a compound, optionally a cyclic compound described herein (e.g. comprising for example QKL, KLV or QKLV (SEQ ID NO: 1).

An immunogen is suitably prepared or formulated for administration to a subject, for example, the immunogen may be sterile, or purified. In an embodiment, the immunogen is a cyclic peptide comprising QKLV (SEQ ID NO: 1) or a related epitope sequence.

In an embodiment, the immunogen comprises immunogenicity enhancing agent such as Keyhole Limpet Hemocyanin (KLH). The immunogenicity enhancing agent can be coupled to the compound either directly, such as through an amide bound, or indirectly through a functionalizable moiety in the linker. When the linker is a single amino acid residue (for example with the A-beta peptide in the cyclic compound is 6 amino acid residues) the linker can be the functionalizable moiety (e.g. a cysteine residue).

The immunogen can be produced by conjugating the cyclic compound containing the constrained epitope peptide to an immunogenicity enhancing agent such as Keyhole Limpet Hemocyanin (KLH) or a carrier such bovine serum albumin (BSA) using for example the method described in Lateef et al 2007, herein incorporated by reference. In an embodiment, the method described in Example 3 or 4 is used.

A further aspect is an isolated nucleic acid encoding the proteinaceous portion of a compound or immunogen described herein. In embodiment, the nucleic acid molecule encodes any one of the amino acid sequences sent forth in SEQ ID NOs: 1-10.

In an embodiment, nucleic acid molecule encodes QKLV (SEQ ID NO: 1) or a related epitope and optionally a linker described herein.

A further aspect is a vector comprising said nucleic acid. Suitable vectors are described elsewhere herein.

ii) Antibodies, Cells and Nucleic Acids

The compounds and particularly the cyclic compounds described above can be used to raise antibodies that specifically bind QKLV (SEQ ID NO: 1) in A-beta and/or which recognize specific conformations of QKLV (SEQ ID NO: 1) in A-beta. As demonstrated in the Examples, the cyclic compound CGQKLVG (SEQ ID NO: 3) was immunogenic, and produced a number of antibodies that specifically and/or selectively bind the cyclic compound relative to the corresponding linear peptide. In addition, antibodies raised to CGQKLVG (SEQ ID NO: 3) specifically and/or selectively bound A-beta oligomers, lacked or had negligible plaque binding, inhibited propagation of A-beta aggregation and inhibited A-beta oligomer induced neural toxicity in vitro.

Accordingly, the compounds and particularly the cyclic compounds described above can be used to raise antibodies that specifically bind QKLV (SEQ ID NO: 1) in A-beta and/or which recognize specific conformations of these residues in A-beta, including one or more differential features described herein. Similarly cyclic compounds comprising for example related epitope sequences described herein such as SEQ ID NO: 1, 2, 9 or 10, can be used to raise antibodies that specifically selectively bind conformational epitopes of QKLV (SEQ ID NO: 1).

Accordingly, an aspect includes an antibody (including a binding fragment thereof) that specifically binds to an A-beta peptide having a sequence QKLV (SEQ ID NO: 1) or a related epitope sequence, for example as set forth in any one of SEQ ID NO: 1, 2, 9 or 10.

In an embodiment, the A-beta peptide is comprised in a cyclic compound, optionally a cyclic peptide, and the antibody is specific or selective for the portion of A-beta presented in the cyclic compound.

In an embodiment, the antibody selectively binds A-beta peptide in a cyclic compound, in the context of cyclo (CGQKLVG) (SEQ ID NO: 3) relative to a linear peptide comprising QKLV (SEQ ID NO: 1), optionally in the context of linear CGQKLVG (SEQ ID NO: 3), e.g. corresponding linear sequence. For example, in an embodiment the antibody selectively binds QKLV (SEQ ID NO: 1) in a cyclic conformation and has at least 2 fold, at least 3 fold, at least 5 fold, at least 10 fold at least 20 fold, at least 30 fold, at least 40 fold, at least 50 fold, at least 100 fold, at least 500 fold, at least 1000 fold more selective greater selectivity QKLV (SEQ ID NO: 1) in the cyclic conformation compared to QKLV (SEQ ID NO: 1) in a linear unstructured compound, for example as measured by ELISA or surface plasmon resonance, or optionally using a method described herein.

In an embodiment, the antibody specially and/or selectively binds the A-beta peptide of the cyclic compound, wherein the A-beta has a sequence as set forth in any one of SEQ ID NOs: 1, 2, 4 to 10.

In an embodiment, the antibody selectively binds to an A-beta portion of a sequence of any of SEQ ID NOs: 1-10 presented in a cyclic compound, compared to a linear compound.

In an embodiment, the cyclic compound is a cyclic peptide. In an embodiment, A-beta peptide in the cyclic peptide is any one of SEQ ID NO: 1, 2, 9 or 10. In an embodiment, the cyclic peptide comprises any one of the sequences in SEQ ID NO: 1-10.

As described in the examples, antibodies having one or more properties can be selected using assays described in the Examples.

In an embodiment, the antibody does not bind a linear peptide comprising the sequence QKLV (SEQ ID NO: 1), optionally wherein the sequence of the linear peptide is a linear version of a cyclic sequence used to raise the antibody as described herein, optionally as set forth in SEQ ID NO: 3.

In an embodiment, the antibody is a conformation specific and/or selective A-beta antibody. For example an antibody that binds a particular epitope conformation can be referred to as a conformation specific antibody. Such antibodies can be selected using the methods described herein. The conformation specific antibody can differentially recognize a particular A-beta species or a group of related species (e.g. dimers, trimers, and other oligomeric species) and can have a higher affinity for one species or group of species compared to another (e.g. to either the A-beta monomer or fibril species).

In an embodiment the antibody is isolated.

In an embodiment, the antibody is an exogenous antibody.

In an embodiment, the antibody specifically binds an epitope on A-beta, the epitope comprising or consisting of QKLV (SEQ ID NO: 1), a related epitope or a part thereof.

As described in the Examples, Q and/or QK and/or QL residues may be predominantly accessible or exposed in conformations of A-beta that are distinct from the monomer and/or fibril forms.

Accordingly a further aspect is an antibody which specifically binds an epitope on A-beta, wherein the epitope comprises or consists of at least one amino acid residue predominantly involved in binding to the antibody, wherein the at least one amino acid is Q, K or L embedded within the sequence QKLV (SEQ ID NO: 1).

In an embodiment, the epitope comprises or consists of at least two consecutive amino acid residues predominantly involved in binding to the antibody, wherein the at least two consecutive amino acids are QK or KL embedded within QKLV (SEQ ID NO: 1).

In another embodiment, the epitope consists of QKLV (SEQ ID NO: 1).

In an embodiment, the antibody does not specifically bind monomeric A-beta. In an embodiment, the antibody does not specifically bind A-beta senile plaques, for example in situ in AD brain tissue.

In another embodiment, the antibody does not selectively bind monomeric A-beta compared to native- or synthetic-oligomeric A-beta.

In an embodiment, the antibody specifically and/or selectively binds a species of A-beta selectively such as A-beta oligomer. In an embodiment, the selectivity is at least 3 fold, at least 5 fold, at least 10 fold, at least 20 fold, at least 30 fold, at least 40 fold, at least 50 fold, at least 100 fold, at least 500 fold, at least 1000 fold more selective for A-beta oligomer over a species of A-beta selected from A-beta monomer and/or A-beta fibril and/or a linear compound comprising QKLV (SEQ ID NO: 1).

In an embodiment, the A-beta oligomer comprises A-beta 1-42 subunits.

In an embodiment, the antibody lacks A-beta fibril plaque (also referred to as senile plaque) staining. Absence of plaque staining can be assessed by comparing to a positive control such as A-beta-specific antibodies 6E10 and 4G8 (Biolegend, San Diego, Calif.), or 2C8 (Enzo Life Sciences Inc., Farmingdale, N.Y.), or any other antibody reactive to fibrillar forms of A-beta, and an isotype control. An antibody described herein lacks or has negligible A-beta fibril plaque staining if the antibody does not show typical plaque morphology staining and the level of staining is comparable to or no more than 2 fold the level seen with an IgG negative isotype control. The scale can for example set the level of staining with isotype control at 1 and with 6E10 at 10. An antibody lacks A-beta fibril plaque staining if the level of staining on such a scale is 2 or less. In embodiment, the antibody shows minimal A-beta fibril plaque staining, for example on the foregoing scale, levels scored at less about or less than 3.

In an embodiment, the antibody is a monoclonal antibody.

To produce monoclonal antibodies, antibody producing cells (lymphocytes) can be harvested from a subject immunized with an described herein, and fused with myeloma cells by standard somatic cell fusion procedures thus immortalizing these cells and yielding hybridoma cells. Such techniques are well known in the art, (e.g. the hybridoma technique originally developed by Kohler and Milstein (Nature 256:495-497 (1975)) as well as other techniques such as the human B-cell hybridoma technique (Kozbor et al., Immunol. Today 4:72 (1983)), the EBV-hybridoma technique to produce human monoclonal antibodies (Cole et al., Methods Enzymol, 121: 140-67 (1986)), and screening of combinatorial antibody libraries (Huse et al., Science 246:1275 (1989)). Hybridoma cells can be screened immunochemically for production of antibodies specifically reactive with the amyotrophic lateral sclerosis-specific epitopes and the monoclonal antibodies can be isolated.

Specific antibodies, or antibody fragments, reactive against particular antigens or molecules, may also be generated by screening expression libraries encoding immunoglobulin genes, or portions thereof, expressed in bacteria with cell surface components. For example, complete Fab fragments, VH regions and FV regions can be expressed in bacteria using phage expression libraries (see for example Ward et al., Nature 41:544-546 (1989); Huse et al., Science 246:1275-1281 (1989); and McCafferty et al., Nature 348: 552-554 (1990).

In an embodiment, the antibody is a humanized antibody.

The humanization of antibodies from non-human species has been well described in the literature. See for example EP-B1 0 239400 and Carter & Merchant 1997 (Curr Opin Biotechnol 8, 449-454, 1997 incorporated by reference in their entirety herein). Humanized antibodies are also readily obtained commercially (eg. Scotgen Limited, 2 Holly Road, Twickenham, Middlesex, Great Britain.).

Humanized forms of rodent antibodies are readily generated by CDR grafting (Riechmann et al. Nature, 332:323-327, 1988). In this approach the six CDR loops comprising the antigen binding site of the rodent monoclonal antibody are linked to corresponding human framework regions. CDR grafting often yields antibodies with reduced affinity as the amino acids of the framework regions may influence antigen recognition (Foote & Winter. J Mol Biol, 224: 487-499, 1992). To maintain the affinity of the antibody, it is often necessary to replace certain framework residues by site directed mutagenesis or other recombinant techniques and may be aided by computer modeling of the antigen binding site (Co et al. J Immunol, 152: 2968-2976, 1994).

Humanized forms of antibodies are optionally obtained by resurfacing (Pedersen et al. J Mol Biol, 235: 959-973, 1994). In this approach only the surface residues of a rodent antibody are humanized.

Human antibodies specific to a particular antigen may be identified by a phage display strategy (Jespers et al. Bio/Technology, 12: 899-903, 1994). In one approach, the heavy chain of a rodent antibody directed against a specific antigen is cloned and paired with a repertoire of human light chains for display as Fab fragments on filamentous phage. The phage is selected by binding to antigen. The selected human light chain is subsequently paired with a repertoire of human heavy chains for display on phage, and the phage is again selected by binding to antigen. The result is a human antibody Fab fragment specific to a particular antigen. In another approach, libraries of phage are produced were members display different human antibody fragments (Fab or Fv) on their outer surfaces (Dower et al., WO 91/17271 and McCafferty et al., WO 92/01047). Phage displaying antibodies with a desired specificity are selected by affinity enrichment to a specific antigen. The human Fab or Fv fragment identified from either approach may be recloned for expression as a human antibody in mammalian cells.

Human antibodies are optionally obtained from transgenic animals (U.S. Pat. Nos. 6,150,584; 6,114,598; and 5,770,429). In this approach the heavy chain joining region (JH) gene in a chimeric or germ-line mutant mouse is deleted. Human germ-line immunoglobulin gene array is subsequently transferred to such mutant mice. The resulting transgenic mouse is then capable of generating a full repertoire of human antibodies upon antigen challenge.

Antibodies, including humanized or human antibodies, are selected from any class of immunoglobulins including: IgM, IgG, IgD, IgA or IgE; and any isotype, including: IgG1, IgG2, IgG3 and IgG4. Chimeric, humanized or human antibodies may include sequences from one or more than one isotype or class.

Further, these antibodies are typically produced as antigen binding fragments such as Fab, Fab' F(ab')2, Fd, Fv and single domain antibody fragments, or as single chain antibodies in which the heavy and light chains are linked by a spacer. Also, the human or humanized antibodies may exist in monomeric or polymeric form. The humanized antibody optionally comprises one non-human chain and one humanized chain (i.e. one humanized heavy or light chain).

Additionally, antibodies specific for the epitopes described herein are readily isolated by screening antibody phage display libraries. For example, an antibody phage library is optionally screened by using a disease specific epitope of the current invention to identify antibody fragments specific for the disease specific epitope. Antibody fragments identified are optionally used to produce a variety of recombinant antibodies that are useful with different embodiments of the present invention. Antibody phage display libraries are commercially available, for example, through Xoma (Berkeley, Calif.) Methods for screening antibody phage libraries are well known in the art.

A further aspect is antibody and/or binding fragment thereof comprising a light chain variable region and a heavy chain variable region, the heavy chain variable region comprising complementarity determining regions CDR-H1, CDR-H2 and CDR-H3, the light chain variable region comprising complementarity determining region CDR-L1, CDR-L2 and CDR-L3 and with the amino acid sequences of said CDRs comprising the sequences set forth below:

| Chain | CDR | Sequence | SEQ ID NO |
|---|---|---|---|
| Heavy | CDR-H1 | GYTFTDYE | 11 |
|  | CDR-H2 | IDPETGDT | 12 |
|  | CDR-H3 | TSPIYYDYDWFAY | 13 |
| Light | CDR-L1 | QSLLNNRTRKNY | 14 |
|  | CDR-L2 | WAS | 15 |
|  | CDR-L3 | KQSYNLRT | 16 |
| and/or | | | |
| Chain | CDR | Sequence | SEQ ID NO |
| Heavy | CDR-H1 | GFSLSTSGMG | 21 |
|  | CDR-H2 | IWWDDDK | 22 |
|  | CDR-H3 | ARSITTVVATPFDY | 23 |
| Light | CDR-L1 | QNVRSA | 24 |
|  | CDR-L2 | LAS | 25 |
|  | CDR-L3 | LQHWNSPFT | 26 |

In an embodiment, the antibody is a monoclonal antibody. In an embodiment, the antibody is a chimeric antibody such as a humanized antibody comprising the CDR sequences as recited in Tables 6 and/or 8.

Also provided in another embodiment, is an antibody comprising the CDRs in Table 6 and/or 8 and a light chain variable region and a heavy chain variable region, optionally in the context of a single chain antibody.

In yet another aspect, the antibody comprises a heavy chain variable region comprises: i) an amino acid sequence as set forth in SEQ ID NO: 18 or 28; ii) an amino acid sequence with at least 50%, at least 60%, at least 70%, at least 80% sequence identity to SEQ ID NO: 18 or 28, wherein the CDR sequences are as set forth in SEQ ID NO: 11, 12, 13, 21, 22, and/or 23, or iii) a conservatively substituted amino acid sequence i). In another aspect the antibody comprises a light chain variable region comprising i) an amino acid sequence as set forth in SEQ ID NO: 20 or 30, ii) an amino acid sequence with at least 50%, at least 60%, at least 70%, at least 80% 70% sequence identity to SEQ ID NO: 20 or 30, wherein the CDR sequences are as set forth in SEQ ID NO: 14, 15, 16, 24, 25 an/or 26, or iii) a conservatively substituted amino acid sequence of i). In another embodiment, the heavy chain variable region amino acid sequence is encoded by a nucleotide sequence as set out in SEQ ID NO: 17 or 27 or a codon degenerate optimized version thereof. In another embodiment, the antibody comprises a light chain variable region amino acid sequence encoded by a nucleotide sequence as set out in SEQ ID NO: 19 or 29 or a codon degenerate or optimized version thereof. In an embodiment, the heavy chain variable region comprises an amino acid sequence as set forth in SEQ ID NO: 18 or 28. In an embodiment, the light chain variable region comprises an amino acid sequence as set forth in SEQ ID NO: 20 or 30.

Another aspect is an antibody that specifically binds a same epitope as the antibody with CDR sequences as recited in Table 6 and/or 8.

Another aspect includes an antibody that competes for binding to human A-beta with an antibody comprising the CDR sequences as recited in Table 6 and/or 8.

Competition between antibodies can be determined for example using an assay in which an antibody under test is assessed for its ability to inhibit specific binding of a reference antibody to the common antigen. A test antibody competes with a reference antibody if an excess of a test antibody (e.g., at least a 2 fold, 5, fold, 10 fold or 20 fold) inhibits binding of the reference antibody by at least 50%, at least 75%, at least 80%, at least 90% or at least 95% as measured in a competitive binding assay.

A further aspect is an antibody conjugated to a therapeutic, detectable label or cytotoxic agent. In an embodiment, the detectable label is a positron-emitting radionuclide. A positron-emitting radionuclide can be used for example in PET imaging.

A further aspect relates to an antibody complex comprising an antibody described herein and/or a binding fragment thereof and oligomeric A-beta.

A further aspect is an isolated nucleic acid encoding an antibody or part thereof described herein.

Nucleic acids encoding a heavy chain or a light chain are also provided, for example encoding a heavy chain comprising CDR-H1, CDR-H2 and/or CDR-H3 regions described herein or encoding a light chain comprising CDR-L1, CDR-L2 and/or CDR-L3 regions described herein.

The present disclosure also provides variants of the nucleic acid sequences that encode for the antibody and/or binding fragment thereof disclosed herein. For example, the variants include nucleotide sequences that hybridize to the nucleic acid sequences encoding the antibody and/or binding fragment thereof disclosed herein under at least moderately stringent hybridization conditions or codon degenerate or optimized sequences In another embodiment, the variant nucleic acid sequences have at least 50%, at least 60%, at least 70%, most preferably at least 80%, even more preferably at least 90% and even most preferably at least 95% sequence identity to nucleic acid sequences encoding a proteinaceous sequence herein including any one of SEQ ID NOs: 18, 20, 28 and 30.

In an embodiment, the nucleic acid is an isolated nucleic acid.

Another aspect is an expression cassette or a vector comprising the nucleic acid herein disclosed. In an embodiment, the vector is an isolated vector.

The vector can be any vector, including vectors suitable for producing an antibody and/or binding fragment thereof or expressing an epitope peptide sequence described herein.

The nucleic acid molecules may be incorporated in a known manner into an appropriate expression vector which ensures expression of the protein. Possible expression vectors include but are not limited to cosmids, plasmids, or modified viruses (e.g. replication defective retroviruses, adenoviruses and adeno-associated viruses). The vector should be compatible with the host cell used. The expression vectors are "suitable for transformation of a host cell", which means that the expression vectors contain a nucleic acid molecule encoding the peptides corresponding to epitopes or antibodies described herein.

In an embodiment, the vector is suitable for expressing for example single chain antibodies by gene therapy. The vector can be adapted for specific expression in neural tissue, for example using neural specific promoters and the like. In an embodiment, the vector comprises an IRES and allows for expression of a light chain variable region and a heavy chain variable region. Such vectors can be used to deliver antibody in vivo.

Suitable regulatory sequences may be derived from a variety of sources, including bacterial, fungal, viral, mammalian, or insect genes.

Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector.

In an embodiment, the regulatory sequences direct or increase expression in neural tissue and/or cells.

In an embodiment, the vector is a viral vector.

The recombinant expression vectors may also contain a marker gene which facilitates the selection of host cells transformed, infected or transfected with a vector for expressing an antibody or epitope peptide described herein.

The recombinant expression vectors may also contain genes which encode a fusion moiety (i.e. a "fusion protein") which provides increased expression or stability of the recombinant peptide; increased solubility of the recombinant peptide; and aid in the purification of the target recombinant peptide by acting as a ligand in affinity purification, including for example tags and labels described herein. Further, a proteolytic cleavage site may be added to the target recombinant protein to allow separation of the recombinant protein from the fusion moiety subsequent to purification of the fusion protein. Typical fusion expression vectors include pGEX (Amrad Corp., Melbourne, Australia), pMAL (New England Biolabs, Beverly, Mass.) and pRIT5 (Pharmacia, Piscataway, N.J.) which fuse glutathione S-transferase (GST), maltose E binding protein, or protein A, respectively, to the recombinant protein.

Systems for the transfer of genes for example into neurons and neural tissues both in vitro and in vivo include vectors based on viruses, most notably Herpes Simplex Virus, Adenovirus, Adeno-associated virus (AAV) and retroviruses including lentiviruses. Alternative approaches for gene delivery include the use of naked, plasmid DNA as well as liposome—DNA complexes. Another approach is the use of AAV plasmids in which the DNA is polycation-condensed and lipid entrapped and introduced into the brain by intracerebral gene delivery (Leone et al. US Application No. 2002076394).

Accordingly in another aspect, the compounds, immunogens, nucleic acids, vectors and antibodies described herein may be formulated in vesicles such as liposomes, nanoparticles, and viral protein particles, for example for delivery of antibodies, compounds, immunogens and nucleic acids described herein. In particular synthetic polymer vesicles, including polymersomes, can be used to administer antibodies.

Also provided in another aspect is a cell, optionally an isolated and/or recombinant cell, expressing an antibody described herein or comprising an expression cassette or vector herein disclosed.

The recombinant cell can be generated using any cell suitable for producing a polypeptide, for example suitable for producing an antibody and/or binding fragment thereof. For example to introduce a nucleic acid (e.g. a vector) into a cell, the cell may be transfected, transformed or infected, depending upon the vector employed.

Suitable host cells include a wide variety of prokaryotic and eukaryotic host cells. For example, the peptides and antibodies described herein may be expressed in bacterial cells such as *E. coli*, insect cells (using baculovirus), yeast cells or mammalian cells.

In an embodiment, the cell is a eukaryotic cell selected from a yeast, plant, worm, insect, avian, fish, reptile and mammalian cell.

In an embodiment, the cell is a fused cell such as a hybridoma cell.

In another embodiment, the mammalian cell is a myeloma cell, a spleen cell, or a hybridoma cell.

In an embodiment, the cell is a neural cell.

Yeast and fungi host cells suitable for expressing an antibody or peptide include, but are not limited to *Saccharomyces cerevisiae, Schizosaccharomyces pombe*, the genera *Pichia* or *Kluyveromyces* and various species of the genus *Aspergillus*. Examples of vectors for expression in yeast *S. cerivisiae* include pYepSec1, pMFa, pJRY88, and pYES2 (Invitrogen Corporation, San Diego, Calif.). Protocols for the transformation of yeast and fungi are well known to those of ordinary skill in the art.

Mammalian cells that may be suitable include, among others: COS (e.g., ATCC No. CRL 1650 or 1651), BHK (e.g. ATCC No. CRL 6281), CHO (ATCC No. CCL 61), HeLa (e.g., ATCC No. CCL 2), 293 (ATCC No. 1573) and NS-1 cells. Suitable expression vectors for directing expression in mammalian cells generally include a promoter (e.g., derived from viral material such as polyoma, Adenovirus 2, cytomegalovirus and Simian Virus 40), as well as other transcriptional and translational control sequences. Examples of mammalian expression vectors include pCDM8 and pMT2PC.

A further aspect is a hybridoma cell line producing an antibody specific for an epitope described herein.

Compositions

A further aspect is a composition comprising a compound, immunogen, nucleic acid, vector or antibody described herein.

In an embodiment, the composition comprises a diluent.

Suitable diluents for nucleic acids include but are not limited to water, saline solutions and ethanol.

Suitable diluents for polypeptides, including antibodies or fragments thereof and/or cells include but are not limited to saline solutions, pH buffered solutions and glycerol solutions or other solutions suitable for freezing polypeptides and/or cells.

In an embodiment, the composition is a pharmaceutical composition comprising any of the peptides, immunogens, antibodies, nucleic acids or vectors disclosed herein, and optionally comprising a pharmaceutically acceptable carrier.

The compositions described herein can be prepared by per se known methods for the preparation of pharmaceutically acceptable compositions that can be administered to subjects, optionally as a vaccine, such that an effective quantity of the active substance is combined in a mixture with a pharmaceutically acceptable vehicle.

Pharmaceutical compositions include, without limitation, lyophilized powders or aqueous or non-aqueous sterile injectable solutions or suspensions, which may further contain antioxidants, buffers, bacteriostats and solutes that render the compositions substantially compatible with the tissues or the blood of an intended recipient. Other components that may be present in such compositions include water, surfactants (such as Tween), alcohols, polyols, glycerin and vegetable oils, for example. Extemporaneous injection solutions and suspensions may be prepared from sterile powders, granules, tablets, or concentrated solutions or suspensions. The composition may be supplied, for example but not by way of limitation, as a lyophilized powder which is reconstituted with sterile water or saline prior to administration to the patient.

Pharmaceutical compositions may comprise a pharmaceutically acceptable carrier. Suitable pharmaceutically acceptable carriers include essentially chemically inert and nontoxic compositions that do not interfere with the effectiveness of the biological activity of the pharmaceutical composition. Examples of suitable pharmaceutical carriers include, but are not limited to, water, saline solutions, glycerol solutions, ethanol, N-(1(2,3-dioleyloxy)propyl)N, N,N-trimethylammonium chloride (DOTMA), diolesyl-phosphotidyl-ethanolamine (DOPE), and liposomes. Such compositions should contain a therapeutically effective amount of the compound, together with a suitable amount of carrier so as to provide the form for direct administration to the patient.

The composition may be in the form of a pharmaceutically acceptable salt which includes, without limitation, those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

In an embodiment comprising a compound or immunogen described herein, the composition comprises an adjuvant.

Adjuvants that can be used for example, include Intrinsic adjuvants (such as lipopolysaccharides) normally are the components of killed or attenuated bacteria used as vaccines. Extrinsic adjuvants are immunomodulators that are typically non-covalently linked to antigens and are formulated to enhance the host immune responses. Aluminum hydroxide, aluminum sulfate and aluminum phosphate (collectively commonly referred to as alum) are routinely used as adjuvants. A wide range of extrinsic adjuvants can provoke potent immune responses to immunogens. These include saponins such as Stimulons (QS21, Aquila, Worcester, Mass.) or particles generated therefrom such as ISCOMs and (immunostimulating complexes) and ISCOMATRIX, complexed to membrane protein antigens (immune stimulating complexes), pluronic polymers with mineral oil, killed mycobacteria and mineral oil, Freund's complete adjuvant, bacterial products such as muramyl dipeptide (MDP) and lipopolysaccharide (LPS), as well as lipid A, and liposomes.

In an embodiment, the adjuvant is aluminum hydroxide. In another embodiment, the adjuvant is aluminum phosphate. Oil in water emulsions include squalene; peanut oil; MF59 (WO 90/14387); SAF (Syntex Laboratories, Palo Alto, Calif.); and Ribi™ (Ribi Immunochem, Hamilton, Mont.). Oil in water emulsions may be used with immunostimulating agents such as muramyl peptides (for example, N-acetylmuramyl-L-threonyl-D-isoglutamine (thr-MDP), -acetyl-normuramyl-L-alanyl-D-isoglutamine (nor-MDP), N-acetylmuramyl-L-alanyl-D-isoglutamyl-L-alanine-2-(1'-2'dipalmitoyl-sn-glycero-3-hydroxyphosphoryloxy)-ethylamine (MTP-PE), N-acetylglucsaminyl-N-acetylmuramyl-L-Al-D-isoglu-L-Ala-dipalmitoxy propylamide (DTP-DPP) theramide(TM)), or other bacterial cell wall components.

The adjuvant may be administered with an immunogen as a single composition. Alternatively, an adjuvant may be administered before, concurrent and/or after administration of the immunogen.

Commonly, adjuvants are used as a 0.05 to 1.0 percent solution in phosphate—buffered saline. Adjuvants enhance the immunogenicity of an immunogen but are not necessarily immunogenic themselves. Adjuvants may act by retaining the immunogen locally near the site of administration to produce a depot effect facilitating a slow, sustained release of immunogen to cells of the immune system. Adjuvants can also attract cells of the immune system to an immunogen depot and stimulate such cells to elicit immune responses. As such, embodiments encompass compositions further comprising adjuvants.

Adjuvants for parenteral immunization include aluminum compounds (such as aluminum hydroxide, aluminum phosphate, and aluminum hydroxy phosphate). The antigen can be precipitated with, or adsorbed onto, the aluminum compound according to standard protocols. Other adjuvants such as RIBI (ImmunoChem, Hamilton, Mont.) can also be used in parenteral administration.

Adjuvants for mucosal immunization include bacterial toxins (e.g., the cholera toxin (CT), the *E. coli* heat-labile toxin (LT), the Clostridium difficile toxin A and the pertussis toxin (PT), or combinations, subunits, toxoids, or mutants thereof). For example, a purified preparation of native cholera toxin subunit B (CTB) can be of use. Fragments, homologs, derivatives, and fusion to any of these toxins are also suitable, provided that they retain adjuvant activity. Preferably, a mutant having reduced toxicity is used. Suitable mutants have been described (e.g., in WO 95/17211 (Arg-7-Lys CT mutant), WO 96/6627 (Arg-192-Gly LT mutant), and WO 95/34323 (Arg-9-Lys and Glu-129-Gly PT mutant)). Additional LT mutants that can be used in the methods and compositions include, for example Ser-63-Lys, Ala-69-Gly, Glu-110-Asp, and Glu-112-Asp mutants. Other adjuvants (such as a bacterial monophosphoryl lipid A (MPLA) of various sources (e.g., *E. coli*, Salmonella minnesota, Salmonella typhimurium, or Shigella flexneri, saponins, or polylactide glycolide (PLGA) microspheres) can also be used in mucosal administration.

Other adjuvants include cytokines such as interleukins for example IL-1, IL-2 and IL-12, chemokines, for example CXCL10 and CCL5, macrophage stimulating factor, and/or tumor necrosis factor. Other adjuvants that may be used include CpG oligonucleotides (Davis. Curr Top Microbiol Immunol., 247:171-183, 2000).

Oil in water emulsions include squalene; peanut oil; MF59 (WO 90/14387); SAF (Syntex Laboratories, Palo Alto, Calif.); and Ribi™ (Ribi Immunochem, Hamilton, Mont.). Oil in water emulsions may be used with immunostimulating agents such as muramyl peptides (for example, N-acetylmuramyl-L-threonyl-D-isoglutamine (thr-MDP), -acetyl-normuramyl-L-alanyl-D-isoglutamine (nor-MDP), N-acetylmuramyl-L-alanyl-D-isoglutamyl-L-alanine-2-(1'-2'dipalmitoyl-sn-glycero-3-hydroxyphosphoryloxy)-ethylamine (MTP-PE), N-acetylglucsaminyl-N-acetylmuramyl-L-Al-D-isoglu-L-Ala-dipalmitoxy propylamide (DTP-DPP) theramide(TM)), or other bacterial cell wall components.

Adjuvants useful for both mucosal and parenteral immunization include polyphosphazene (for example, WO 95/2415), DC-chol (3 b-(N—(N',N'-dimethyl aminomethane)-carbamoyl) cholesterol (for example, U.S. Pat. No. 5,283,185 and WO 96/14831) and QS-21 (for example, WO 88/9336).

An adjuvant may be coupled to an immunogen for administration. For example, a lipid such as palmitic acid, may be coupled directly to one or more peptides such that the change in conformation of the peptides comprising the immunogen does not affect the nature of the immune response to the immunogen.

The adjuvant may be administered with an immuogen as a single composition. Further, an adjuvant may be administered before, concurrent or after administration of the immunogen.

In an embodiment, the composition comprises an antibody described herein. In another embodiment, the composition comprises an antibody described herein and a diluent. In an embodiment, the composition is a sterile composition.

III. Kits

A further aspect relates to a kit comprising i) an antibody and/or binding fragment thereof, ii) a nucleic acid, iii) composition or iv) recombinant cell described herein, comprised in a vial such as a sterile vial or other housing and optionally a reference agent and/or instructions for use thereof.

In an embodiment, the kit further comprises one or more of a collection vial, standard buffer and detection reagent.

IV. Methods

Included are methods for making the compounds, immunogens and antibodies described herein.

In particular, provided are methods of making an antibody selective for a conformational epitope of QKLV (SEQ ID NO: 1) or related epitope comprising administering to a subject, optionally a non-human subject, a conformationally restricted compound comprising an epitope sequence described herein, optionally cyclic compound comprising QKLV (SEQ ID NO: 1) or related epitope, and isolating antibody producing cells or antibodies that specifically or selectively bind the cyclic compound and optionally i) specifically or selectively bind synthetic and/or native oligomers and/or that have no or negligible senile plaque binding in situ tissue samples or no or negligible binding to a corresponding linear peptide. The cyclic compound can for example comprise any of the "epitopes" described herein containing cyclic compounds described herein.

In an embodiment, the method is for making a monoclonal antibody using for example a method as described herein.

In an embodiment, the method is for making a humanized antibody using for example a method described herein.

Antibodies produced using a cyclic compound are selected as described herein and in the Examples. In an embodiment, the method comprises isolating antibodies that specifically or selectively bind cyclic peptide over linear peptide, are specific for the epitope sequence, specifically bind oligomer and/or lack or negligibly bind plaque in situ and/or corresponding linear peptide, optionally using a method described herein.

A further aspect provides a method of detecting whether a biological sample comprises A-beta the method comprising contacting the biological sample with an antibody described herein and detecting the presence of any antibody complex. In an embodiment, the method is for detecting whether a biological sample comprises A-beta. In an embodiment the method is for detecting whether the sample comprises A-beta wherein QKLV (SEQ ID NO: 1) or a related epitope is in an alternate conformation for example wherein at least Q, L or V is in an alternate conformation than occupied by Q, L or V in a non-oligomeric conformation.

In an embodiment, the method comprises:

a. contacting the biologic sample with an antibody described herein that is specific and/or selective for A-beta oligomer herein under conditions permissive to produce an antibody:A-beta oligomer complex; and b. detecting the presence of any complex;

wherein the presence of detectable complex is indicative that the sample may contain A-beta oligomer.

In an embodiment, the level of complex formed is compared to a test antibody such as a suitable Ig control or irrelevant antibody.

In an embodiment, the detection is quantitated and the amount of complex produced is measured. The measurement can for example be relative to a standard.

In an embodiment, the measured amount is compared to a control.

In another embodiment, the method comprises:

(a) contacting a biological sample of said subject with an antibody described herein, under conditions permissive to produce an antibody-antigen complex;

(b) measuring the amount of the antibody-antigen complex in the test sample; and (c) comparing the amount of antibody-antigen complex in the test sample to a control;

wherein detecting antibody-antigen complex in the biological sample as compared to the control indicates that the sample comprises A-beta.

The control can be a sample control (e.g. from a subject without AD, or from a subject with a particular form of AD, mild, moderate or advanced), or be a previous sample from the same subject for monitoring changes in A-beta oligomer levels in the subject.

In an embodiment, an antibody described herein is used.

In an embodiment, the A-beta comprising a QKLV (SEQ ID NO: 1) conformational epitope is A-beta oligomer, wherein the detecting the presence of antigen:antibody complex is indicative that the sample may contain A-beta oligomer.

In an embodiment, the antibody specifically and/or selectively recognizes a conformation of A-beta comprising a QKLV (SEQ ID NO: 1) or related conformational epitope, and detecting the antibody antigen complex in the biological sample is indicative that sample comprises A-beta oligomer.

In an embodiment, the sample is a biological sample. In an embodiment, the sample comprises brain tissue or an extract thereof and/or CSF. In an embodiment, the sample comprises whole blood, plasma or serum. In an embodiment, the sample is obtained from a human subject. In an embodiment, the subject is suspected of, at a risk of or has AD.

A number of methods can be used to detect an A-beta: antibody complex and thereby determine if A-beta comprising a QKLV (SEQ ID NO: 1) or related conformational epitope and/or A-beta oligomers is present in the biological sample using the antibodies described herein, including immunoassays such as flow cytometry, Western blots, ELISA, and immunoprecipitation followed by SDS-PAGE immunocytochemistry.

As described in the Examples surface plasmon resonance technology can be used to assess conformation specific binding. If the antibody is labeled or a detectably labeled secondary antibody specific for the complex antibody is used, the label can be detected. Commonly used reagents include fluorescent emitting and HRP labeled antibodies. In quantitative methods, the amount of signal produced can be measured by comparison to a standard or control. The measurement can also be relative.

A further aspect includes a method of measuring a level of or imaging A-beta in a subject or tissue, optionally where the A-beta to be measured or imaged is oligomeric A-beta. In an embodiment, the method comprises administering to a subject at risk or suspected of having or having AD, an antibody conjugated to a detectable label; and detecting the label, optionally quantitatively detecting the label. The label in an embodiment is a positron emitting radionuclide which can for example be used in PET imaging.

A further aspect includes a method of inducing an immune response in a subject, comprising administering to the subject a compound described herein, optionally a cyclic compound comprising QKLV (SEQ ID NO: 1) or a related epitope peptide sequence, an immunogen and/or composition comprising said compound or said immunogen; and optionally isolating cells and/or antibodies that specifically and/or selectively bind the A-beta peptide in the compound or immunogen administered. In an embodiment, the composition is a pharmaceutical composition comprising the compound or immunogen in admixture with a pharmaceutically acceptable, diluent or carrier.

In an embodiment, the subject is a non-human subject such as a rodent. Antibody producing cells generated are used in an embodiment to produce a hybridoma cell line.

In an embodiment, the immunogen administered comprises a compound of FIG. 12.

Figure 21:
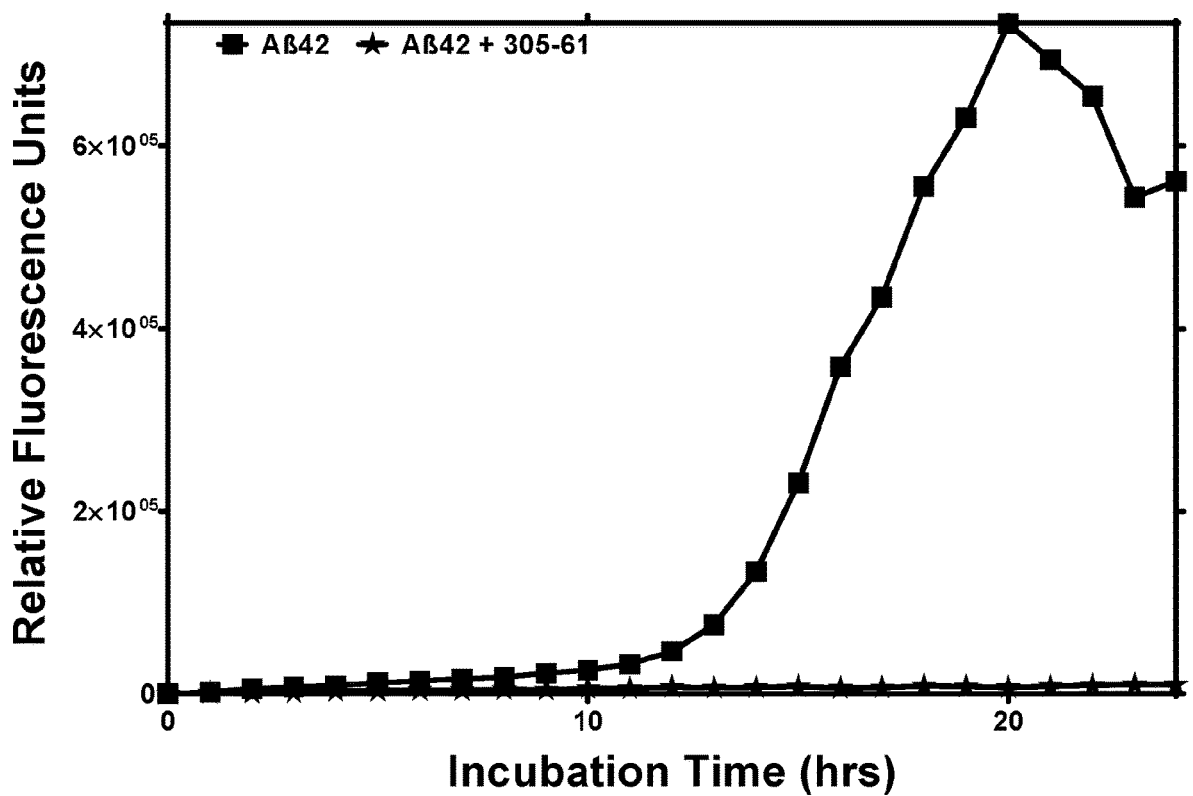
FIG. 21 A-C: Plots showing propagation of A-beta aggregation in vitro in the presence (stars) or absence (squares) of representative antibodies raised using a cyclic peptide comprising QKLV (SEQ ID NO: 1).
Figure 21:
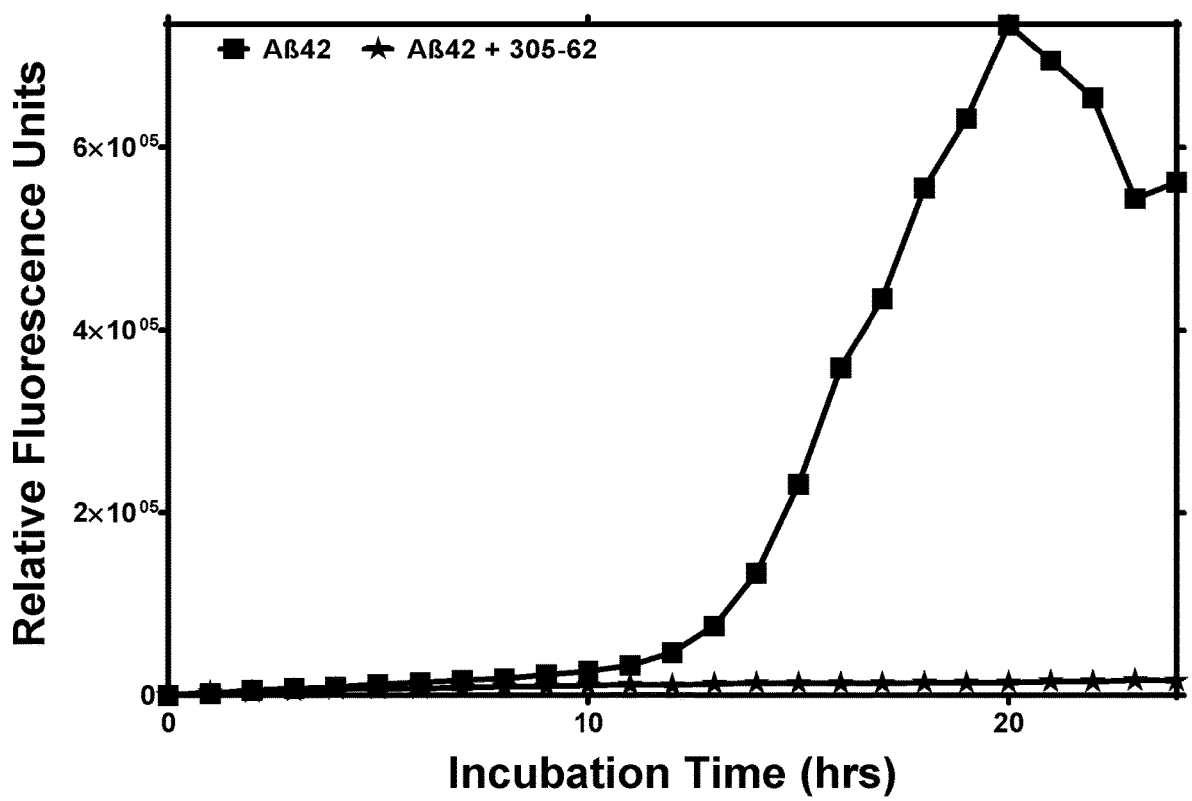
Figure 21:
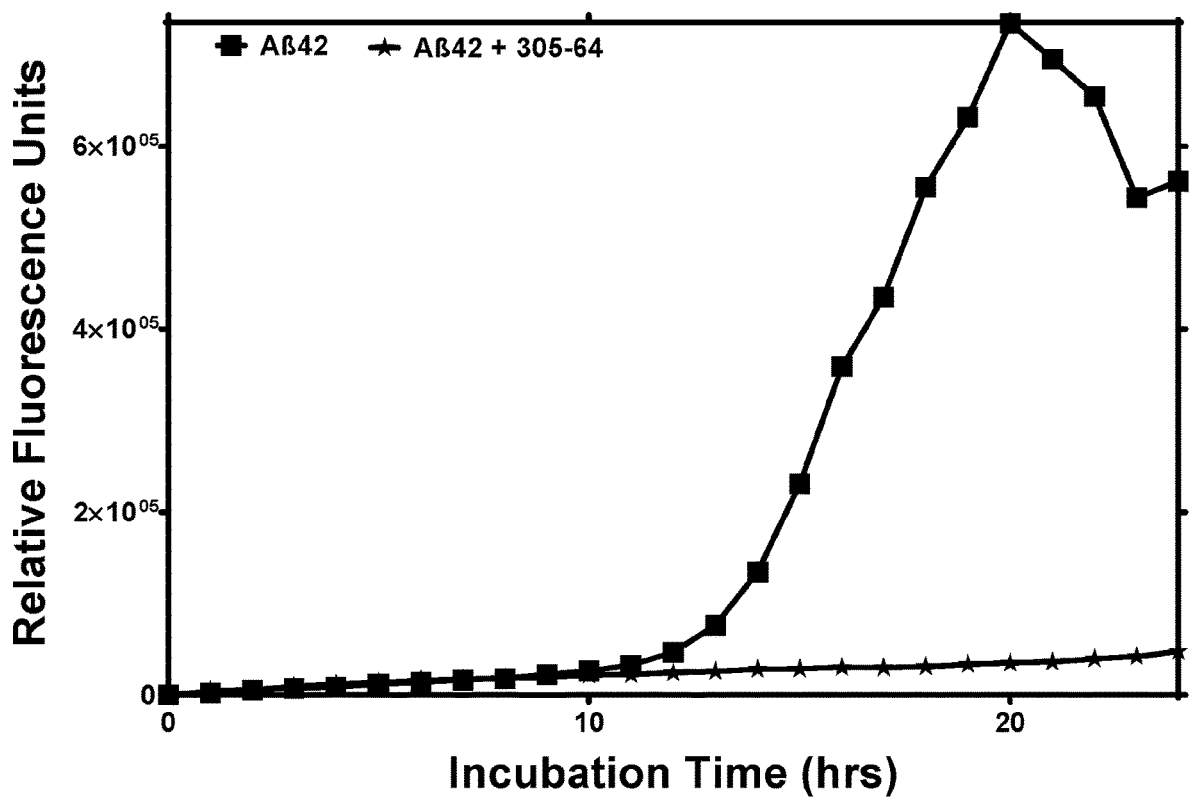
Figure 22:
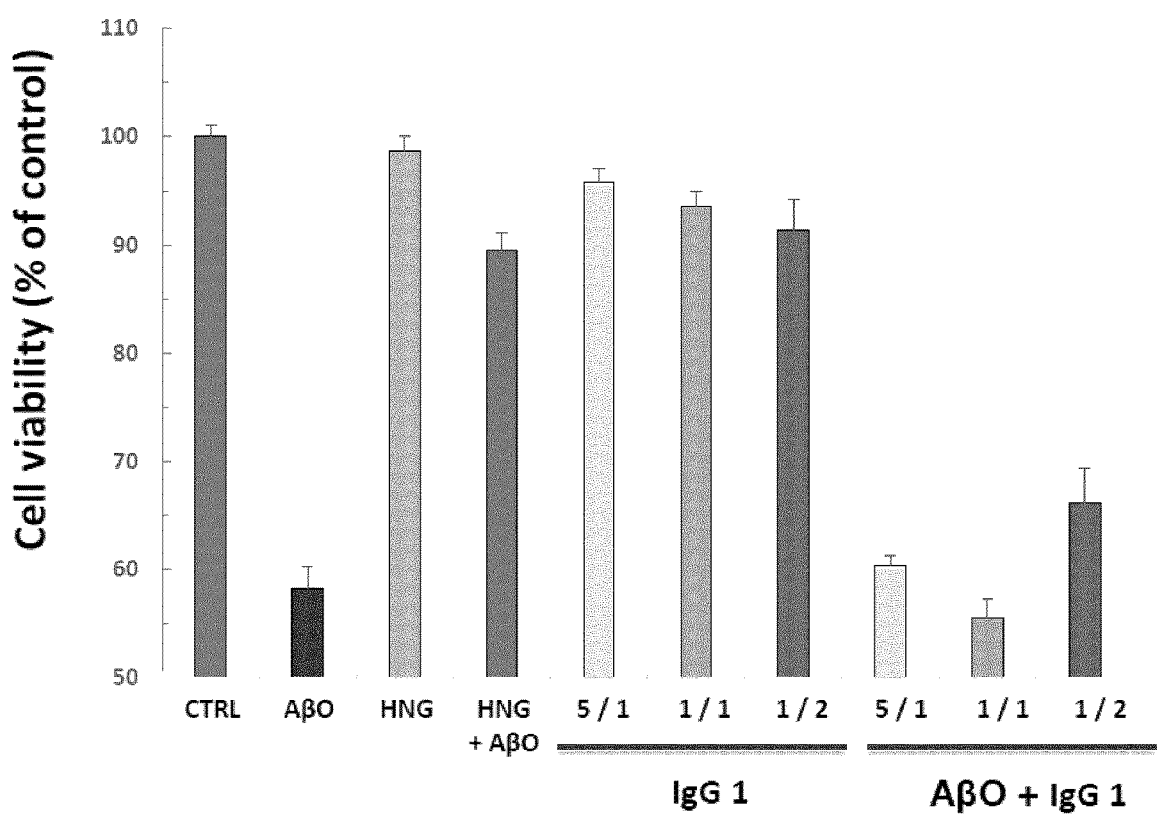
FIG. 22 A-B: A) A plot showing the viability of rat primary cortical neurons exposed to toxic A-beta oligomers (AβO) in the presence or absence of different molar ratios of a negative isotype control (A) or an antibody (B) raised against cyclo(CGQKLVG (SEQ ID NO: 3). Controls include neurons cultured alone (CTRL), neurons incubated with antibody without oligomers and neurons cultured with the neuroprotective humanin peptide (HNG) with or without Aβ oligomers Table 1 shows the binding properties of selected tissue culture supernatant clones.
Figure 22:
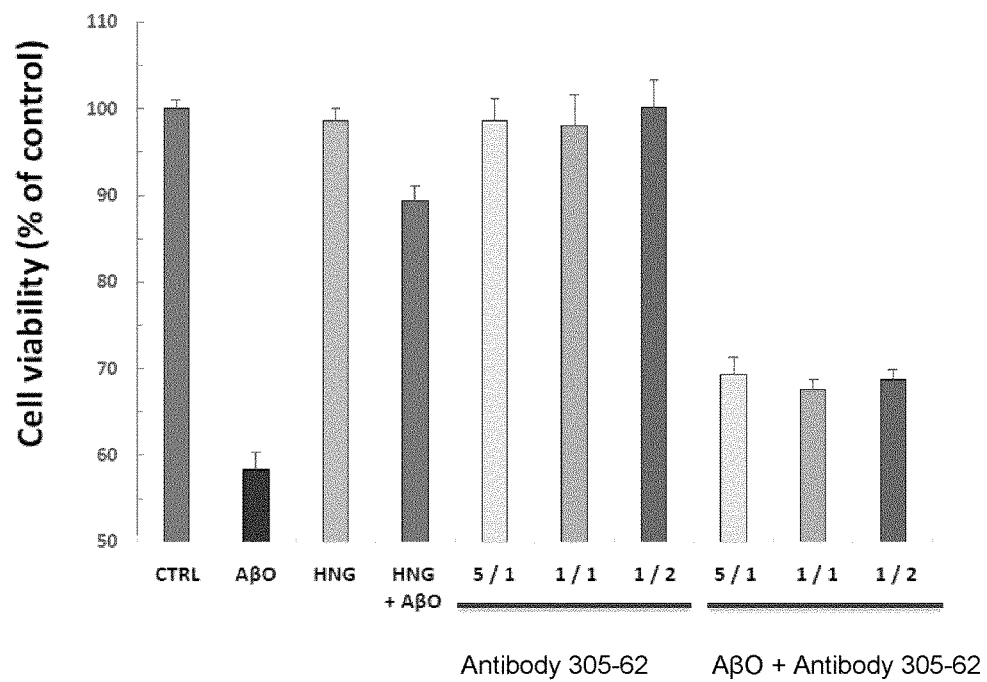

It is demonstrated herein that antibodies raised against cycloCGQKLVG (SEQ ID NO: 2), can specifically and/or selectively bind A-beta oligomers and lack A-beta plaque staining. Oligomeric A-beta species are believed to be the toxic propagating species in AD. Further as shown in FIG. 21, antibodies raised using cyclo(CGQKLVG) (SEQ ID NO: 3) and specific for oligomers, inhibited A-beta aggregation and A-beta oligomer propagation. In addition, such antibodies inhibited the toxicity of A-beta oligomers on neural cells in an in vitro assay (FIG. 22) Accordingly, also provided are methods of inhibiting A-beta oligomer propagation, the method comprising contacting a cell or tissue expressing A-beta with or administering to a subject in need thereof an effective amount of an A-beta oligomer specific or selective antibody described herein to inhibit A-beta aggregation and/or oligomer propagation. In vitro the assay can be monitored as described in Example 10.

The antibodies may also be useful for treating AD and/or other A-beta amyloid related diseases. For example, variants of Lewy body dementia and in inclusion body myositis (a muscle disease) exhibit similar plaques as AD and A-beta can also form aggregates implicated in cerebral amyloid angiopathy. As mentioned, antibodies raised to cyclo (CGQKLVG) (SEQ ID NO: 3) bind oligomeric A-beta which is believed to be a toxigenic species of A-beta in AD and inhibit formation and propagation of toxigenic A-beta oligomers.

Accordingly a further aspect is a method of treating AD and/or other A-beta amyloid related diseases, the method comprising administering to a subject in need thereof i) an effective amount of an antibody described herein, optionally an A-beta oligomer specific or selective or a pharmaceutical composition comprising said antibody; or 2) administering an isolated cyclic compound comprising QKLV (SEQ ID NO: 1) or a related epitope sequence or immunogen or pharmaceutical composition comprising said cyclic compound, to a subject in need thereof.

In an embodiment, a biological sample from the subject to be treated is assessed for the presence or levels of A-beta using an antibody described herein. In an embodiment, a subject with detectable A-beta levels (e.g. A-beta antibody complexes measured in vitro or measured by imaging) is treated with the antibody.

The antibody and immunogens can for example be comprised in a pharmaceutical composition as described herein, and formulated for example in vesicles for improving delivery.

One or more antibodies targeting cycloCGQKLVG (SEQ ID NO: 3) and/or related antibodies can be administered in combination. In addition the antibodies disclosed herein can be administered with one or more other treatments such as a beta-secretase inhibitor or a cholinesterase inhibitor.

In an embodiment, the antibody is a conformation specific/selective antibody, optionally that specifically or selectively binds A-beta oligomer.

Also provided are uses of the compositions, antibodies, isolated peptides, immunogens and nucleic acids for treating AD.

The compositions, compounds, antibodies, isolated peptides, immunogens and nucleic acids, vectors etc. described herein can be administered for example, by parenteral, intravenous, subcutaneous, intramuscular, intracranial, intraventricular, intrathecal, intraorbital, ophthalmic, intraspinal, intracisternal, intraperitoneal, intranasal, aerosol or oral administration.

In certain embodiments, the pharmaceutical composition is administered systemically.

In other embodiments, the pharmaceutical composition is administered directly to the brain or other portion of the CNS. For example such methods include the use of an implantable catheter and a pump, which would serve to discharge a pre-determined dose through the catheter to the infusion site. A person skilled in the art would further recognize that the catheter may be implanted by surgical techniques that permit visualization of the catheter so as to position the catheter adjacent to the desired site of administration or infusion in the brain. Such techniques are described in Elsberry et al. U.S. Pat. No. 5,814,014 "Techniques of Treating Neurodegenerative Disorders by Brain Infusion", which is herein incorporated by reference. Also contemplated are methods such as those described in US patent application 20060129126 (Kaplitt and During "Infusion device and method for infusing material into the brain of a patient". Devices for delivering drugs to the brain and other parts of the CNS are commercially available (eg. SynchroMed® EL Infusion System; Medtronic, Minneapolis, Minn.)

In another embodiment, the pharmaceutical composition is administered to the brain using methods such as modifying the compounds to be administered to allow receptor-mediated transport across the blood brain barrier.

Other embodiments contemplate the co-administration of the compositions, compounds, antibodies, isolated peptides, immunogens and nucleic acids described herein with biologically active molecules known to facilitate the transport across the blood brain barrier.

Also contemplated in certain embodiments, are methods for administering the compositions, compounds, antibodies, isolated peptides, immunogens and nucleic acids described herein across the blood brain barrier such as those directed at transiently increasing the permeability of the blood brain barrier as described in U.S. Pat. No. 7,012,061 "Method for increasing the permeability of the blood brain barrier", herein incorporated by reference.

A person skilled in the art will recognize the variety of suitable methods for administering the compositions, compounds, antibodies, isolated peptides, immunogens and nucleic acids described herein directly to the brain or across the blood brain barrier and be able to modify these methods in order to safely administer the products described herein.

The above disclosure generally describes the present application. A more complete understanding can be obtained by reference to the following specific examples. These examples are described solely for the purpose of illustration and are not intended to limit the scope of the application. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Example 1

I. Gō Model Method for Predicting A-Beta Oligomer Specific Epitopes

One epitope prediction model is based on the free energy landscape of partial protein unfolding from the native state. The native state is taken to be an experimentally-derived fibril structure. When the protein is partially unfolded from the native state by a given amount of primary sequence, epitope candidates are contiguous sequence segments that cost the least free energy to disorder. The free energy of a given protein conformation arises from several contributions, including conformational entropy and solvation of polar functional groups that favor the unfolded state, as well as the loss of electrostatic and van der Waals intra-protein interactions that enthalpically stabilize the native state.

A. Gō-Like Model of Protein Partially Unfolding Landscape

An approximate model to account for the free energetic changes that take place during unfolding assigns a fixed energy to all contacts in the native state, where a contact is defined as a pair of heavy (non-hydrogen) atoms within a fixed cut-off distance $r_{cutoff}$. Go-like models have been successfully implemented in previous studies of protein folding. The Gō-like model isolates the effects arising from the topology of native protein interactions, and in practice the unfolding free energy landscape can be readily calculated from a single native state structure.

The total free energy cost of unfolding a segment depends on the number of interactions to be disrupted, together with the conformational entropy term of the unfolded region.

In the following equations, lower case variables refer to atoms, while upper case variables refer to residues. Let T be the set of all residues in the protein, U be the set of residues unfolded in the protein, and F be the subset of residues folded in the protein (thus T=U ∪F). The unfolding mechanism at high degrees of nativeness consists of multiple contiguous strands of disordered residues. Here the approximation of a single contiguous unfolded strand was adopted, and the free energy cost to disorder this contiguous strand was calculated.

The total free energy change $\Delta F_{G\bar{o}}(U)$ for unfolding the set of residues U is $$\Delta F_{G\bar{o}}(U) = E_{G\bar{o}}(U) - T\Delta S_{G\bar{o}}(U) \tag{1}$$

The unfolding enthalpy function $\Delta E_{G\bar{o}}(U)$ is given by the number of interactions disrupted by unfolding of the set of U residues:

$$\Delta E_{G\bar{o}}(\mathcal{U}) = a \sum \Theta(r_{cutoff} - |r_i - r_j|) \tag{2}$$

In Equation 2, the sum on i, j is over all unique pairs of heavy atoms that have either one or both atoms in the unfolded region, $r_i$ and $r_j$ are the coordinates of atoms i and j, $r_{cutoff}$ (taken to be 4.8 Å) is the interaction distance cut-off. $\Theta(x)$ is the Heaviside function defined by $\Theta(x)=1$ if x is positive and 0 otherwise. The energy per contact a may be chosen to recapitulate the overall experimental stability $\Delta F_{Exp}(U)|_{u=T}$ on completely unfolding the protein at room temperature:

$$a = \frac{\Delta F_{Exp}(\mathcal{U})|_{\mathcal{U}=\mathcal{T}} + T\Delta S_{G\bar{o}}(\mathcal{U})|_{\mathcal{U}=\mathcal{T}}}{\sum_{i,j\in}^{i>j} \Theta(r_{cutoff} - |r_i - r_j|)} \tag{3}$$

The results do not depend on this value; it merely sets the overall global energy scale in the problem. In the present model, this free energy was taken to be a constant number equal to 4.6 kcal/mol. This value is not a primary concern as it is the relative free energy cost for the different regions of the same protein that is sought to be disordered in the method of epitope prediction.

The calculation of the unfolding entropy term $\Delta S_{G\bar{o}}(U)$ is discussed in B below.

B. Entropy Calculation

The number of microstates accessible to the protein in the unfolded state is much greater than the number accessible in the native state, so there is a favorable gain of conformational entropy on unfolding. The total entropy of the unfolding segment U by summing over all the residues K in the unfolded region is calculated $$\Delta S_{G\bar{o}}(\mathcal{U}) = \sum \left( \Delta S_{bb,K} - \left(1 - \frac{A_{\mathcal{U},K}}{A_{\mathcal{U},K}}\right) \Delta S_{bu\to ex,K} + \Delta S_{ex\to sol,K} \right) \tag{4}$$

where $\Delta S_{bb,K}$, $\Delta S_{bu\to ex,K}$, $\Delta S_{ex\to sol,K}$ are the three conformational entropic components of residue K as listed in reference [3]: $\Delta S_{bb,K}$ is the backbone entropy change from native state to unfolded state, $\Delta S_{bu\to ex,K}$ is the entropy change for side-chain from buried inside protein to the surface of the protein, and, and $\Delta S_{ex\to sol,K}$ is the entropy obtained for the side-chain from the surface to the solution.

A correction is applied to the unfolded state conformational entropies, since in the single sequence approximation the end points of the partially unfolded strand are fixed in their positions in the native structure. This means that there is a loop entropy penalty to be paid for constraining the ends in the partially unfolded structure, which is not present in the fully unfolded state $$S_{return} = -k_B \ln(f_w(R|N)\Delta T) \tag{5}$$

Here $f_w(R|N)_{\Delta T}$ is found by calculating the probability an ideal random walk returns to a box of volume $\Delta T$ centered at position R after N steps, without penetrating back into the protein during the walk. For strand lengths shorter than about n≈20 residues, the size of the melted strand is much smaller than the protein diameter and the steric excluded volume of the protein is well treated as an impenetrable plane. The number of polymeric states of the melted strand must be multiplied by the fraction of random walks that travel from an origin on the surface of the protein to a location where the melted polymer re-enters the protein without touching or crossing the impenetrable plane. The above fraction of states can be written in the following form:

$$f_w(R|N) = \frac{a}{N^{5/2}} \exp\left(-\frac{3R^2}{2Nl^2} - \frac{N^2 V_c}{2R^3}\right) \tag{6}$$

where R is the end to end distance between the exit and entrance locations, N is the number of residues of the melted region, and a, l, $V_C$ are parameters determined by fitting to unfolded polypeptide simulations. The parameter l is the effective arc length between two $C_\alpha$ atoms, and $V_C$ is the average excluded volumes for each residue. By fitting the Equation 6 into the simulation results, the values of the parameters a=0.0217, l=4.867, $V_C$=3.291 are obtained. This entropy penalty is general and independent of the sequence.

Disulfide bonds require additional consideration in the loop entropy term since they further restrict the motion of the unfolded segment. When present, the disulfide is treated as an additional node through which the loop must pass, in effect dividing the full loop into two smaller loops both subject to the boundary conditions described above.

C. Epitope Prediction from Free Energy Landscape

Once the free energy landscape of partially unfolding the protein is obtained, a variable energy threshold $E_{th}$ is applied, and the segments that contains no fewer than 3 amino acids and with free energy cost below the threshold are predicted as epitope candidates. The prediction is stable with respect to varying the threshold value $E_{th}$.

II. Epitopes Predictions from A-Beta Disrupted Fibril Structures

From the native structure in 2M4J, the unfolding free energy landscape using the Gō-like model as described in I A was calculated. The result is shown in FIG. 1. The epitope QKLV (SEQ ID NO: 1) emerges as a candidate epitope in this analysis.

The free energy cost in cal/mol is shown, for all epitopes with free energy cost less than 10 kcal/mol. The epitope marked with a box giving the x,y,z values is centered at residue ID 17 (x-axis), and has length 4 (y-axis), thus consisting of residue 15-18 or QKLV (SEQ ID NO: 1). For even-numbered epitopes, the "center" is defined by convention as the residue to the right of the numerical center, simply for purposes of plotting the figure.

FIG. 1 shows the top view of the free energy landscape below a threshold Eth=10 kcal/mol, where the x-axis is the center of the segment, y-axis is the length of the segment, and the depth of color represents the free energy needed to melt the corresponding segment. From FIG. 1, at the energy scale of 10 kcal/mol, the epitope consisting of residues 15-18 or sequence QKLV (SEQ ID NO: 1) emerges as a predicted epitope in chains A, B and C of the structure PDB 2M4J.

The fibril model contains chains "A" to "I". For example, the determined structure of the fibril consists of a repeating unit of 9 chains, which are identified as chains A-I. The identified epitope presents for chains A, B, and C.

Figure 2:
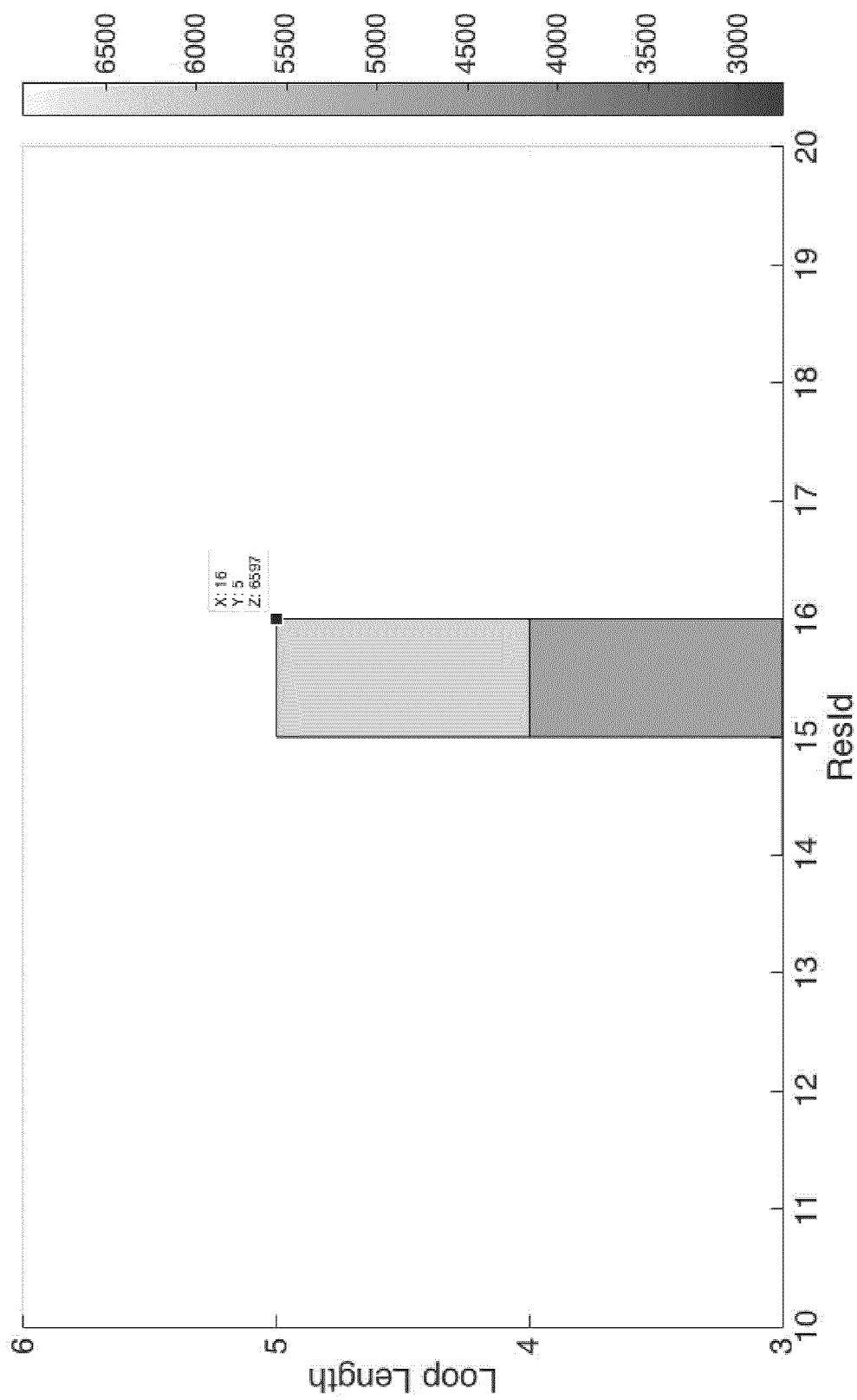
FIG. 2 is a landscape graph of partially unfolding 2MXU, threshold 7 kcal/mol.

Likewise for structure A-beta fibril structure 2MXU, an epitope of sequences 14-18 emerges for chain A (sequence HQKLV; FIG. 2). HQKLV (SEQ ID NO: 2) is consistent with an increased solvent exposure of Q and/or QK in the alternate conformation compared to monomeric or fibrillary A-beta.

Example 2

Iii. Collective Coordinates Predictions

A second method for predicting misfolded epitopes is provided by a method referred to as "Collective Coordinates biasing" which is described in U.S. Patent Application Ser. No. 62/253,044, SYSTEMS AND METHODS FOR PREDICTING MISFOLDED PROTEIN EPITOPES BY COLLECTIVE COORDINATE BIASING filed Nov. 9, 2015, and is incorporated herein by reference. As described therein, the method uses molecular-dynamics-based simulations which impose a global coordinate bias on a protein (or peptide-aggregate) to force the protein (or peptide-aggregate) to misfold and then predict the most likely unfolded regions of the partially unstructured protein (or peptide aggregate). Biasing simulations were performed and the solvent accessible surface area (SASA) corresponding to each residue index (compared to that of the initial structure of the protein under consideration). SASA represents a surface area that is accessible to H2O. A positive change in SASA (compared to that of the initial structure of the protein under consideration) may be considered to be indicative of unfolding in the region of the associated residue index. The method was applied to three A-beta strains, each with its own morphology: a three-fold symmetric structure of Aβ-40 peptides (or monomers) (PDB entry 2M4J), a two-fold symmetric structure of Aβ-40 monomers (PDB entry 2LMN), and a single-chain, parallel in-register (e.g. a repeated beta sheet where the residues from one chain interact with the same residues from the neighboring chains) structure of Aβ-42 monomers (PDB entry 2MXU).

Simulations were performed for each initial structure using the collective coordinates method as described in U.S. Patent Application Ser. No. 62/253,044, SYSTEMS AND METHODS FOR PREDICTING MISFOLDED PROTEIN EPITOPES BY COLLECTIVE COORDINATE BIASING and the CHARMM force-field parameters described in: K. Vanommeslaeghe, E. Hatcher, C. Acharya, S. Kundu, S. Zhong, J. Shim, E. Darian, O. Guvench, P. Lopes, I. Vorobyov, and A. D. Mackerell. Charmm general force field: A force field for drug-like molecules compatible with the charmm all-atom additive biological force fields. *Journal of Computational Chemistry*, 31(4):671-690, 2010; and P. Bjelkmar, P. Larsson, M. A. Cuendet, B. Hess, and E. Lindahl. Implementation of the CHARMM force field in GROMACS: analysis of protein stability effects from correlation maps, virtual interaction sites, and water models. *J. Chem. Theo. Comp.*, 6:459-466, 2010, both of which are hereby incorporated herein by reference, with TIP3P water.

Figure 8:
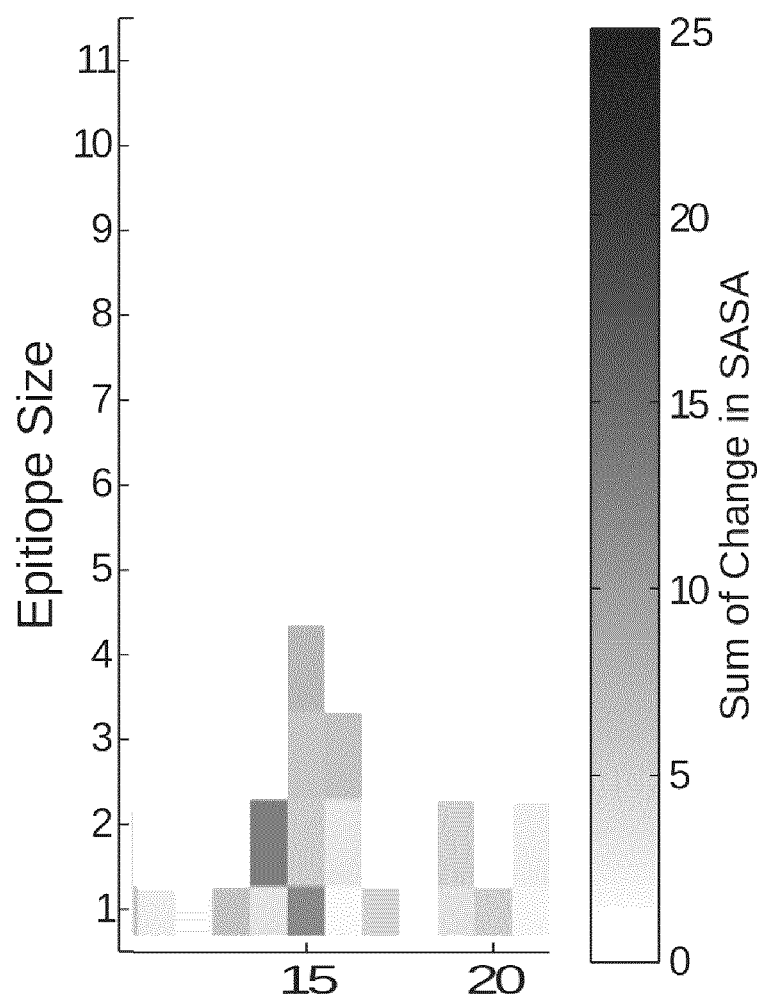
FIG. 8 is a graph showing the likelihood of exposure as a function of sequence, as determined by the collective coordinates method. A peak emerges around centered residue 17.
Figure 9:
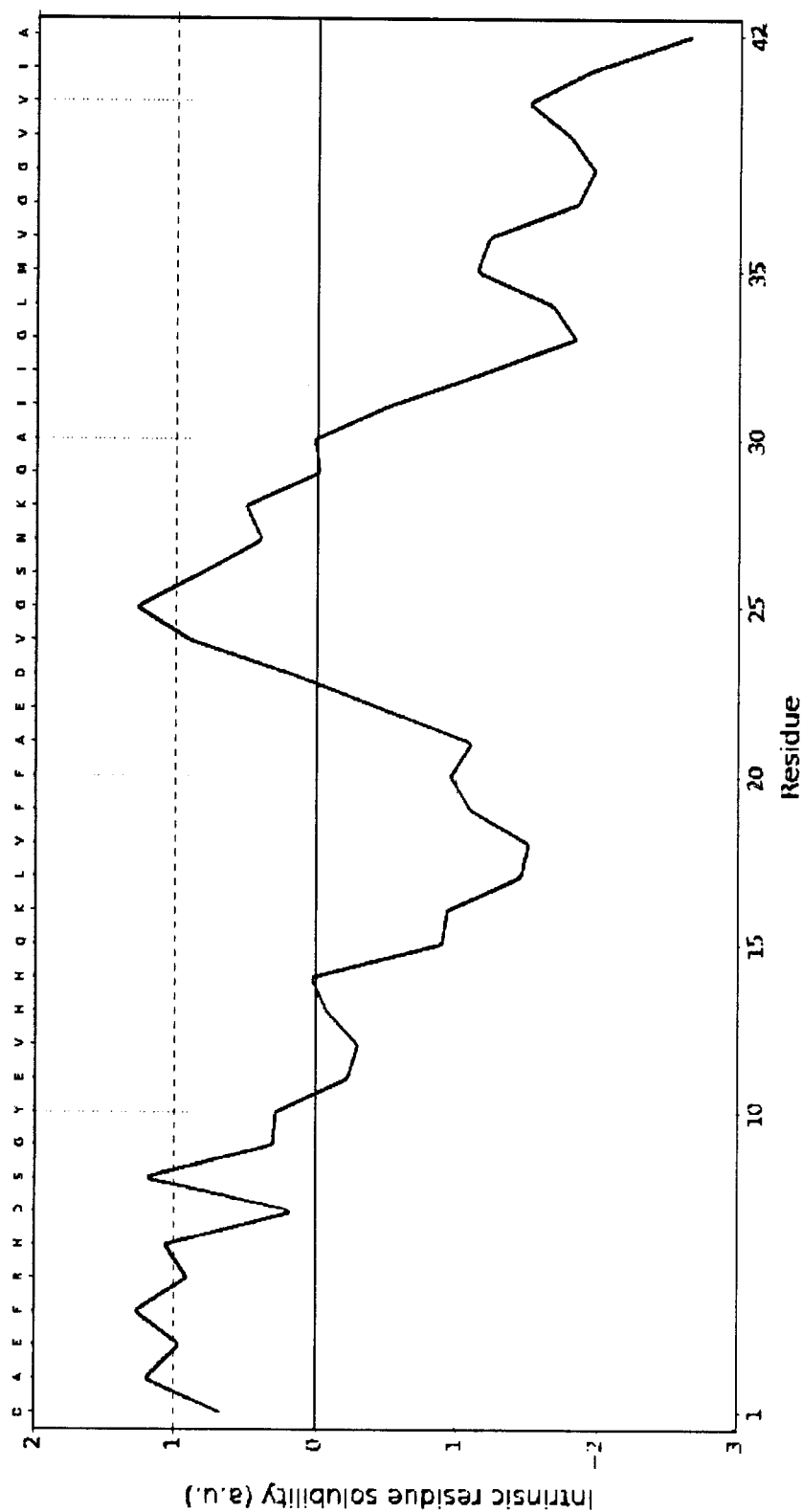
FIG. 9 is a graph showing the solubility vs residue index for A-beta 42 peptide.

The SASA of amino acid side chains as a function of residue index, for one monomer of the 3 fold symmetric A-beta structure 2M4J, after biasing to 80% of its initial structure was analysed. One region that emerged with reliably increased SASA was residues 14-17, corresponding to residues HQKL, and shown in FIG. 8. HQKL is consistent with an increased solvent exposure of Q and/or QK in the alternate conformation compared to monomeric or fibrillary A-beta.

An epitope consisting of residues 14-17 was predicted for the 3-fold A-beta40 (2M4J) and 2 fold A-beta 40 (2LMN) structures.

An epitope consisting of residues 15-19 was predicted from A-beta40 (2MXU) and an epitope consisting of residues 15-20 was predicted for A-beta42 constrained ends.

Different biasing demonstrates that the general structure of the predicted epitopes does depend significantly on the degree of biasing.

FIG. 13 is a plot of the entropy with respect to the fibril for both a linear peptide CGQKLVG (SEQ ID NO: 3) and a cyclic peptide cyclo(CGQKLVG) (SEQ ID NO: 3). As shown therein the side chain entropy is reduced for the cyclic compound as compared to the linear peptide, indicating that the side-chains are more conformationally-constrained than when the side-chains are in the linear peptide, i.e. than in free A-beta monomer.

Example 3

Constrained peptide structures comprising QKLV (SEQ ID NO: 1) may mimic the conformational epitope identified using the prediction programs described. Cyclic structures were designed and assessed including structures shown in FIG. 12. The cyclic structure shown in FIG. 12A was assessed as described in Example 4.

Example 4

Determination of Structures Comprising the Conformational Epitope QKLV (SEQ ID NO: 1) that Approximates its Predicted Orientation in A-Beta Oligomers A cyclic compound comprising the QKLV (SEQ ID NO: 1) epitope (as shown in FIG. 5A) was assessed for providing an epitope with conformational relatedness or dissimilarity to the epitope orientation in A-beta fibril and monomers.

I. Curvature of the Cyclic Peptide

The curvature of the cyclic peptide compound backbone shown in FIG. 12(a) has a profile different—it is larger—from either that of the fibril or that of the monomer, implying that an antibody directed against the cyclic peptide may show selectivity for a species presenting a different conformational ensemble than that of either the monomer or fibril. The curvature profiles are shown in FIG. 3.

FIG. 3 is a plot showing curvature as a function of residue index. The average curvature in the equilibrium ensembles for the cyclic peptide CGQKLVG (SEQ ID NO: 3) is shown (long arrow), along with the curvature for the linear peptide (short arrow), and the curvature of the various monomers in the fibril (thin curves length of peptide), and the average curvature for the fibril (thick curve length of peptide).

The curvature as used herein refers to the backbone curvature and is defined as the rate of change of the tangent vector as one moves along the backbone. This can be quantified by taking the unit tangent vector between consecutive C_alpha atoms and then noting how it changes from one tangent to the next. The precise mathematical definition used here is a discrete version of the traditional definition of the curvature of a space curve in differential geometry: $K_{i+1}$-arccos($t_i \cdot t_{i+1}$), where t, is the unit tangent vector from C_alpha(i) to C_alpha(i+1). The curvature is then simply an angle in radians that may vary in principle from 0 (parallel) to π (antiparallel), depending on the backbone configuration.

The values of the curvature were determined for Q, K, L, V in cyclo(CGQKLVG) (SEQ ID NO: 3), linear CGQKLVG (SEQ ID NO: 3), and QKLV (SEQ ID NO: 1) in the context of the fibril respectively as:
Cyclic peptide: 1.248 1.566 1.422 1.46
Linear Peptide: 0.870 1.355 0.931 1.303
Fibril: 0.740 1.159 0.796 1.188
The averages of these are:
Cyclic peptide: 1.42
Linear peptide: 1.11
Fibril: 0.97

For the plots of curvature, and dihedral angle distributions below, the data are obtained from equilibrium simulations in explicit solvent (SPC) using the Charmm27. cyclic peptide ensemble: simulation time 1 ns, containing 500 frames linear peptide ensemble: simulation time 10 ns, containing 1000 frames 2m4j ensemble: 680 ps, containing 68 frames.

Because the curvature of the cyclic epitope is larger, a hypothetical turn on the oligomer containing these residues would have a backbone orientation that is distinct from that in the fibril or monomer, however the degree of curvature would not be unphysical—values of curvature characterizing the cyclic peptide are obtained in several locations of the fibril.

II. Dihedral Angle Distributions

As further computational support that the identified epitope may define an oligomer-specifc epitope in A-beta, the dihedral angle distributions in the cyclic peptide of FIG. 12 a) which may be a proxy for an exposed epitope in the oligomer—are substantially different from the corresponding distributions in either the fibril or monomer.

Distributions of dihedral angles for Q15 are substantially different in the cyclic peptide from either the monomer or fibril distributions (FIG. 4A), for many of the side-chain dihedrals.

FIG. 4B shows an image for the cyclic peptide CGQKLVG (SEQ ID NO: 3); image taken from an equilibrium molecular dynamics simulation. In this image, the glutamine (Q) residue has sidechain rendered with the $C_\alpha$, $C_\beta$, $C_x$, and $C_\delta$ atoms shown as black beads, and the corresponding dihedral bond shown in black. This dihedral has significantly different dihedral distribution in the cyclic peptide than the corresponding dihedral distributions explored by either the linear peptide or by the residue in the context of the fibril (see FIG. 4A, panel Res-Q:CA-CB-CG-CD).

Likewise, dihedral distributions can be examined for K, L, and V. The dihedral distributions are shown for K16 in FIG. 5. The differences for K are less apparent than they are for Q.

The dihedral distributions are shown for L17 in FIG. 6.

The dihedral distributions are shown for V18 in FIG. 7.

Though L17 shows some discrepancies from linear peptide distributions, particularly for dihedrals involving backbone atoms that differentiate linear from cyclic conformations, the residue showing the most significant difference from either linear or fibril distributions is Q15.

Q15-K16 for example in the context of QKL or QKLV may be key residues on the epitope. Further support for the importance of these residues is provided by a surface area and solubility analysis described herein.

III. Solubility and Antigenicity of the Epitope

The solubility of the residues of A-beta 42 according to the CamSol prediction scheme [4] is shown in the FIG. 9. Residues QKLV (SEQ ID NO: 1) in FIG. 9 have values of −0.899, −0.936, −1.46, and −1.51 respectively. The solubility decreases as one continues towards the C-terminus.

The more soluble a residue is, the more likely it is to be encountered on the surface of any species of A-beta, and in particular it is more likely to be on or near the surface of the oligomer. A residue will be solvated on the surface of unstructured monomer, and may not be solvated on the surface of fibrils (because of an organized structure). Oligomers will be partially and dynamically structured so that the exposure of specific residues which are not solvent-accessible in the fibril, optionally in combination with one or more conformational features, may distinguish the oligomer from the fibril.

A relative solubility factor $\sigma_i$ for residue i, can be defined as $$\sigma_i = \frac{s_i - s_{min}}{s_{max} - s_{min}}$$

where s, is the solubility of residue i, and $s_{max}$ and $s_{min}$ are the maximum and minimum values of the solubility in a given range of residues. Here, simply to set a scale for plotting values, the range of residues is arbitrarily chosen to be HQKLVF (SEQ ID NO: 9), so that $s_{max}$=0.0302 and $s_{min}$=−1.51.

When SASA is weighted by the solubility of the residue, more emphasis is put on the N-terminal residues in the group QKLV (SEQ ID NO: 1). FIG. 10 plots the solvent accessible surface area (SASA), the SASA weighted by the solubility factor for each residue, σi·SASAi, and σi·SASAi minus the value in the fibril, i.e. the increase in this quantity in the monomer and cyclic peptide over the fibril, σi·ΔSASAi.

Weighting by the solubility results in the Q and K residues having the most likelihood of differential exposure and antigenicity on the surface of oligomers.

Dissection of Solvent-Accessible Surface Area Based on Residue Side-Chain Moieties Separating sidechains of the various residues into atomic groups, shown in FIG. 11, shows that there is a general trend towards larger solvent exposure as one approaches the termini of the side-chains. E.g. Q15 is subdivided into $C_\beta$—$H_2$, $C_\gamma$—$H_2$, $C_\delta$—$O_\epsilon$, and $N_\epsilon$—$H_2$, with the $N_\varepsilon$—$H_2$ having the most SASA in the cyclic peptide as compared to the fibril or monomer. The deviation in solvent exposure w.r.t. the fibril also has a tendency to increase for moieties near the termini of the side chains.

Example 5

Cyclic Compound Construction Comprising a Conformationally Constrained Epitope

Peptides comprising QKLV (SEQ ID NO: 1) such as Cyclo(CGQKLVG) (SEQ ID NO: 3) can be cyclized head to tail.

A linear peptide comprising QKLV (SEQ ID NO: 1) and a linker, preferably comprising 2, 3, or 4 amino acids and/or PEG units, can be synthesized using known methods such as Fmoc based solid phase peptide synthesis alone or in combination with other methods. PEG molecules can be coupled to amine groups at the N terminus for example using coupling chemistries described in Hamley 2014 [6] and Roberts et al 2012 [7], each incorporated herein by reference. The linear peptide compound may be cyclized by covalently bonding 1) the amino terminus and the carboxy terminus of the peptide+linker to form a peptide bond (e.g. cyclizing the backbone), 2) the amino or carboxy terminus with a side chain in the peptide+linker or 3) two side chains in the peptide+linker.

The bonds in the cyclic compound may be all regular peptide bonds (homodetic cyclic peptide) or include other types of bonds such as ester, ether, amide or disulfide linkages (heterodetic cyclic peptide).

Peptides may be cyclized by oxidation of thiol- or mercaptan-containing residues at the N-terminus or C-terminus, or internal to the peptide, including for example cysteine and homocysteine. For example two cysteine residues flanking the peptide may be oxidized to form a disulphide bond. Oxidative reagents that may be employed include, for example, oxygen (air), dimethyl sulphoxide, oxidized glutathione, cystine, copper (II) chloride, potassium ferricyanide, thallium(III) trifluro acetate, or other oxidative reagents such as may be known to those of skill in the art and used with such methods as are known to those of skill in the art.

Methods and compositions related to cyclic peptide synthesis are described in US Patent Publication 2009/0215172. US Patent publication 2010/0240865, US Patent Publication 2010/0137559, and U.S. Pat. No. 7,569,541 describe various methods for cyclization. Other examples are described in PCT Publication WO01/92466, and Andreu et al., 1994. Methods in Molecular Biology 35:91-169.

More specifically, a cyclic peptide comprising the QKLV (SEQ ID NO: 1) epitope can be constructed by adding a linker comprising a spacer with cysteine residues flanking and/or inserted in the spacer. The peptide can be structured into a cyclic conformation by creating a disulfide linkage between the non-native cysteines residues added to the N- and C-termini of the peptide. It can also be synthesized into a cyclic compound by forming a peptide bond between the N- and C-termini amino acids (e.g. head to tail cyclization).

Peptide synthesis is performed by CPC Scientific Inc. (Sunnyvale Calif., USA) following standard manufacturing procedures.

For example Cyclo(CGQKLVC) cyclic peptide comprising the conformational epitope QKLV (SEQ ID NO: 1) is constructed in a constrained cyclic conformation using a disulfide linkage between cysteine residues added to the N- and C-termini of a peptide comprising QKLV (SEQ ID NO: 1). Two non-native cysteine residues were added to GQKLV (SEQ ID NO: 4) one at the C-terminus and one at the N-terminus. The two cysteines are oxidized under controlled conditions to form a disulfide bridge or reacted head to tail to produce a peptide bond.

As described above, the structure of the cyclic peptide was designed to mimic the conformation and orientation of the amino acid side changes of QKLV (SEQ ID NO: 1) in A-beta oligomer.

Cyclo(CGQKLVG)

A linear peptide comprising spacer GCG and epitope peptide QKLV (SEQ ID NO: 1) is synthesized for example using Fmoc based solid-phase peptide synthesis. The solid phase can be on a rink amide resin or on a 2-chlorotrityl resin.

Cyclo(CGQKLVG) (SEQ ID NO: 3) can be prepared by amide condensation of the linear peptide CGQKLVG (SEQ ID NO: 3).

Cyclo(C-PEG2-QKLVG) can be prepared by amide condensation of the linear compound C-PEG2-QKLVG.

Immunogen Construction

The cyclic compound containing the constrained epitope peptide is optionally conjugated to an immunogenicity enhancing agent such as Keyhole Limpet Hemocyanin (KLH) or a carrier such bovine serum albumin (BSA) using for example the method described in Lateef et al 2007, herein incorporated by reference.

Example 6

Antibody Generation and Selection

A conformational constrained compound optionally a cyclic compound such as a cyclic peptide comprising QKLV (SEQ ID NO: 1) such as cyclo(CGQKLVG) (SEQ ID NO: 3) peptide is linked to Keyhole Limpet Hemocyanin (KLH). The cyclopeptide is sent for mouse monoclonal antibody production (ImmunoPrecise Antibodies LTD (Victoria BC, Canada), following protocols approved by the Canadian Council on Animal Care. Mouse sera are screened using either the conformational peptide used for producing the antibodies or a related peptide e.g. cyclo(CGQKLV-peptide) (SEQ ID NO: 3), linked to BSA. Positive IgG-secreting clones are subjected to large-scale production.

Hybridomas were made using an immunogen comprising cyclo(CGQKLVG) (SEQ ID NO: 3) as further described in Example 8. Hybridoma supernatants were screened by ELISA and SPR for preferential binding to cyclo (CGQKLVG) (SEQ ID NO: 3) peptide vs linear (unstructured) peptide as described herein. Positive IgG-secreting clones are subjected to large-scale production and further purification using Protein G.

Example 7

Assessing Binding or Lack thereof to Plaques/Fibrils

For immunostaining, antibodies described herein, positive control 6E10 (1 µg/ml) and isotype control IgG1, IgG2a, IgG2b, or IgG3 (1 µg/ml, Abcam) are used as primary antibodies. Sections are incubated overnight at 4° C., and washed 3×5 min in TBS-T. Anti-Mouse IgG Horseradish Peroxidase conjugated (1:1000, ECL) is applied to sections and incubated 45 min, then washed 3×5 min in TBS-T. DAB chromogen reagent (Vector Laboratories, Burlington ON, Canada) is applied and sections rinsed with distilled water when the desired level of target to background staining is achieved. Sections are counterstained with Mayer's haematoxylin, dehydrated and cover slips were applied. Slides are examined under a light microscope (Zeiss Axiovert 200M, Carl Zeiss Canada, Toronto ON, Canada) and representative images captured at 50, 200 and 400× magnification using a Leica DC300 digital camera and software (Leica Microsystems Canada Inc., Richmond Hill, ON).

Example 8

Methods and Materials

Immunogen

Cyclic and linear peptides were generated at CPC Scientific, Sunnyvale, Calif., USA. Peptides were conjugated to KLH (for immunizing) and BSA (for screening) using a trifluoroacetate counter ion protocol. Peptides were desalted and checked by MS and HPLC and deemed 95% pure.

Peptides were shipped to IPA for use in production of monoclonal antibodies in mouse.

Antibodies

A number of hybridomas and monoclonal antibodies were generated to cyclo(CGQKLVG) (SEQ ID NO: 3) linked to Keyhole Limpet Hemocyanin (KLH).

Fifty day old female BALB/c mice (Charles River Laboratories, Quebec) were immunized. A series of subcutaneous aqueous injections containing antigen but no adjuvant were given over a period of 19 days. Mice were immunized with 100 µg of peptide per mouse per injection of a 0.5 mg/mL solution in sterile saline of cyclic peptide-KLH. Mice were housed in a ventilated rack system from Lab Products. All 4 mice were euthanized on Day 19 and lymphocytes were harvested for hybridoma cell line generation.

Fusion/Hybridoma Development

Lymphocytes were isolated and fused with murine SP2/0 myeloma cells in the presence of poly-ethylene glycol (PEG 1500). Fused cells were cultured using HAT selection. This method uses a semi-solid methylcellulose-based HAT selective medium to combine the hybridoma selection and cloning into one step. Single cell-derived hybridomas grow to form monoclonal colonies on the semi-solid media. 10 days after the fusion event, resulting hybridoma clones were transferred to 96-well tissue culture plates and grown in HT containing medium until mid-log growth was reached (5 days).

Hybridoma Analysis (Screening)

Tissue culture supernatants from the hybridomas were tested by indirect ELISA on screening antigen (cyclic peptide-BSA) (Primary Screening) and probed for both IgG and IgM antibodies using a Goat anti-IgG/IgM(H&L)-HRP secondary and developed with TMB substrate. Clones >0.2 OD in this assay were taken to the next round of testing. Positive cultures were retested on screening antigen to confirm secretion and on an irrelevant antigen (Human Transferrin) to eliminate non-specific mAbs and rule out false positives. All clones of interest were isotyped by antibody trapping ELISA to determine if they are IgG or IgM isotype. All clones of interest were also tested by indirect ELISA on other cyclic peptide-BSA conjugates as well as linear peptide-BSA conjugates to evaluate cross-reactivity.

Mouse hybridoma antibodies were screened by Indirect ELISA using cyclo(CGQKLVG) (SEQ ID NO: 3) conjugated to BSA.

ELISA Antibody Screening

Briefly, the ELISA plates were coated with 0.1 µg/well cyclo(CGQKLVG)—conjugated-BSA (SEQ ID NO: 3) at 100 uL/well in carbonate coating buffer (pH 9.6) O/N at 4 C and blocked with 3% skim milk powder in PBS for 1 hour at room temperature. Primary Antibody: Hybridoma supernatant at 100 uL/well incubated for 1 hour at 37 C with shaking. Secondary Antibody 1:10,000 Goat anti-mouse IgG/IgM(H+L)-HRP at 100 uL/well in PBS-Tween for 1 hour at 37 C with shaking. All washing steps were performed for 30 mins with PBS-Tween. The substrate 3,3',5,5'-tetramethylbenzidine (TMB) was added at 50 uL/well, developed in the dark and stopped with equal volume 1M HCl.

Positive clones were selected for further testing. Positive clones of mouse hybridomas were tested for reactivity to cyclo(CGQKLVG) (SEQ ID NO: 3) conjugated BSA and human transferrin (HT) by indirect ELISA. Plates were coated with 1) 0.1 ug/well cyclo(CGQKLVG)—conjugated-BSA (SEQ ID NO: 3) at 100 uL/well in carbonate coating buffer (pH 9.6) O/N at 4 C; or 2) 0.25 ug/well HT Antigen at 50 uL/well in dH2O/N at 37 C. Primary Antibody: Hybridoma supernatant at 100 uL/well incubated for 1 hour at 37 C with shaking. Secondary Antibody 1:10,000 Goat anti-mouse IgG/IgM(H+L)-HRP at 100 uL/well in PBS-Tween for 1 hour at 37 C with shaking. All washing steps were performed for 30 mins with PBS-Tween. The substrate 3,3',5,5'-tetramethylbenzidine (TMB) was added at 50 uL/well, developed in the dark and stopped with equal volume 1M HCl.

ELISA Cyclo vs Linear CGQKLVG (SEQ ID NO: 3) Compound Selectivity

ELISA plates were coated with 1) 0.1 ug/well cyclo (CGQKLVG)—conjugated-BSA (SEQ ID NO:3) at 100 uL/well in carbonate coating buffer (pH 9.6) O/N at 4 C; 2) 0.1 ug/well linear CGQKLVG—conjugated-BSA (SEQ ID NO:3) at 100 uL/well in carbonate coating buffer (pH 9.6) O/N at 4 C; or 3) 0.1 ug/well Negative-Peptide at 100 uL/well in carbonate coating buffer (pH 9.6) O/N at 4 C. Primary Antibody: Hybridoma supernatant at 100 uL/well incubated for 1 hour at 37 C with shaking. Secondary Antibody 1:10,000 Goat anti-mouse IgG/IgM(H+L)-HRP at 100 uL/well in PBS-Tween for 1 hour at 37 C with shaking. All washing steps were performed for 30 mins with PBS-Tween. The substrate TMB was added at 50 uL/well, developed in the dark and stopped with equal volume 1M HCl.

Isotyping

The hybridoma antibodies were isotyped using antibody trap experiments. Trap plates were coated with 1:10,000 Goat anti-mouse IgG/IgM(H&L) antibody at 100 uL/well carbonate coating buffer pH9.6 overnight at 4 C. No blocking step was used. Primary antibody (hybridoma supernatants) was added (100 ug/mL). Secondary Antibody 1:5,000 Goat anti-mouse IgGγ-HRP or 1:10,000 Goat anti-mouse IgMµ-HRP at 100 uL/well in PBS-Tween for 1 hour at 37 C with shaking. All washing steps were performed for 30 mins with PBS-Tween. The substrate TMB was added at 50 uL/well, developed in the dark and stopped with equal volume 1M HCl.

SPR Binding Assays—Primary and Secondary Screens

SPR Analysis of Antibody Binding to A-Beta Monomers and Oligomers

A-Beta Monomer and Oligomer Preparation

Recombinant A-beta40 and 42 peptides (California Peptide, Salt Lake City Utah, USA) were dissolved in ice-cold hexafluoroisopropanol (HFIP). The HFIP was removed by evaporation overnight and dried in a SpeedVac centrifuge. To prepare monomers, the peptide film was reconstituted in DMSO to 5 mM, diluted further to 100 µM in dH2O and used immediately. Oligomers were prepared by diluting the 5 mM DMSO peptide solution in phenol red-free F12 medium (Life Technologies Inc., Burlington ON, Canada) to a final concentration of 100 µM and incubated for 24 hours to 7 days at 4° C.

SPR Analysis All SPR measurements were performed using a Molecular Affinity Screening System (MASS-1) (Sierra Sensors GmbH, Hamburg, Germany), an analytical biosensor that employs high intensity laser light and high speed optical scanning to monitor binding interactions in real time. The primary screening of tissue culture supernatants was performed using an SPR direct binding assay, whereby BSA-conjugated peptides, A-beta42 Monomer and A-beta42 Oligomer are covalently immobilized on individual flow cells of a High Amine Capacity (HAC) sensorchip (Sierra Sensors GmbH, Hamburg, Germany) and antibodies flowed over the surface. Protein G purified mAbs were analyzed in a secondary screen using an SPR indirect (capture) binding assay, whereby the antibodies were captured on a protein A-derivatized sensorchip (XanTec Bioanalytics GmbH, Duesseldorf, Germany) and A-beta40 Monomer, A-beta42 Oligomer, soluble brain extracts and cerebrospinal fluid flowed over the surface. The specificity of the antibodies was verified in an SPR direct binding assay by covalently immobilizing A-beta42 Monomer and A-beta42 Oligomer on individual flow cells of a HAC sensorchip and flowing purified mAbs.

SPR Analysis of Soluble Brain Extracts and CSF Samples

Soluble Brain Extract and CSF Preparation

Human brain tissues and CSFs were obtained from patients assessed at the UBC Alzheimer's and Related Disorders Clinic. Clinical diagnosis of probable AD is based on NINCDS-ADRDA criteria [5]. CSFs are collected in polypropylene tubes, processed, aliquoted into 100 µL polypropylene vials, and stored at −80° C. within 1 hour after lumbar puncture.

Homogenization:

Human brain tissue samples were weighed and subsequently submersed in a volume of fresh, ice cold TBS (supplemented with EDTA-free protease inhibitor cocktail from Roche Diagnostics, Laval QC, Canada) such that the final concentration of brain tissue is 20% (w/v). Tissue is homogenized in this buffer using a mechanical probe homogenizer (3×30 sec pulses with 30 sec pauses in between, all performed on ice). TBS homogenized samples are then subjected to ultracentrifugation (70,000×g for 90 min). Supernatants are collected, aliquoted and stored at −80° C. The protein concentration of TBS homogenates is determined using a BCA protein assay (Pierce Biotechnology Inc, Rockford Ill., USA).

SPR Analysis

Brain extracts from 4 AD patients and 4 age-matched controls, and CSF samples from 9 AD patients and 9 age-matched controls were pooled and analyzed. Purified mAbs were captured on separate flow cells of a protein A-derivatized sensor chip and diluted samples injected over the surfaces for 180 seconds, followed by 120 seconds of dissociation in buffer and surface regeneration. Binding responses were double-referenced by subtraction of mouse control IgG monoclonal antibody reference surface binding and assay buffer, and the different groups of samples compared Assessing Binding or Lack thereof to A-Beta Monomers In the primary screen of tissue culture supernatants, A-beta42 monomers and A-beta42 oligomers were used in a direct binding assay. In the secondary screen, A-beta40 monomers and A-beta42 oligomers soluble brain extracts and CSF samples were used in an indirect (capture) binding assay.

Primary Screen

Tissue culture supernatants were screened for the presence of antibody binding against their cognate cyclic peptide. Each sample was diluted and injected in duplicate over the immobilized peptide and BSA reference surfaces for 120 seconds, followed by injection of running buffer only for a 300-second dissociation phase. After every analytical cycle, the sensor chip surfaces were regenerated. Sensorgrams were double-referenced by subtracting out binding from the BSA reference surfaces and blank running buffer injections, and binding response report points collected in the dissociation phase.

Oligomer Binding Assay

Next synthetic A-beta 42 oligomers were generated and immobilized as above, antibody binding responses analyzed. Antibody binding responses to A-beta 42 oligomers were compared to binding responses to cyclic.

Verifying Binding to A-Beta Oligomers

To further verify and validate A-beta42 Oligomer binding, antibodies were covalently immobilized, followed by the injection over the surface of commercially-prepared stable A-beta42 Oligomers (SynAging SAS, Vandceuvre-lés-Nancy, France).

Results

ELISA testing found that the majority of hybridoma clones bound the cyclopeptide.

Next clones were tested by ELISA for their binding selectivity for cyclo- and linear-CGQKLVG (SEQ ID NO: 3) compounds. A number of clones preferentially bound cyclo(CGQKLVG)—conjugated-BSA (SEQ ID NO: 3) compared to linear CGQKLVG—conjugated-BSA (SEQ ID NO: 3).

Isotyping revealed that the majority of clones were IgG including IgG1, IgG2a and IgG3 clones. Several IgM and IgA clones were also identified, but not pursued further.

A direct binding analysis using surface plasmon resonance was performed to screen for antibodies in tissue culture supernatants that bind to the cyclic peptide of SEQ ID NO: 3.

Figure 16:
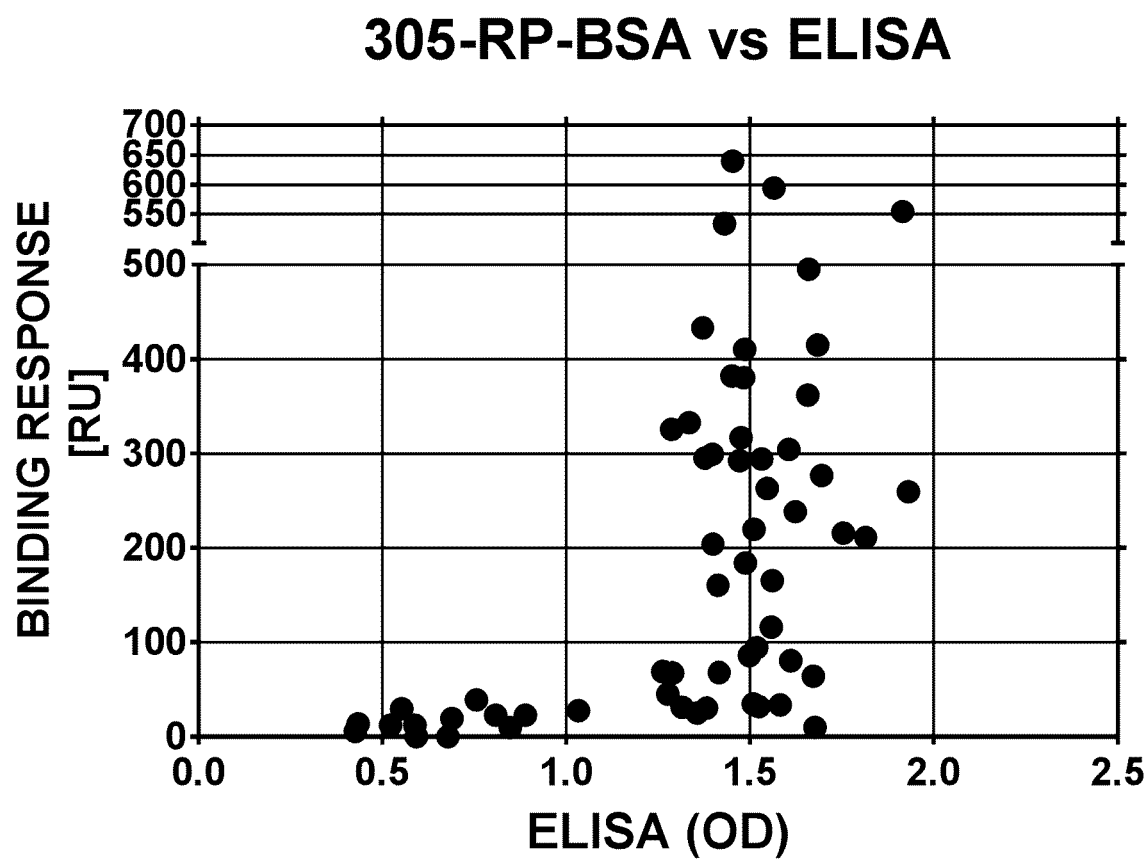
FIG. 16: Plot comparing tissue culture supernatant clone binding in SPR direct binding assay versus ELISA.

FIG. 16 plots the SPR direct binding assay data versus the ELISA binding data, and shows that there is a correlation between the SPR direct binding and ELISA results. Strong binding in SPR only occurs when there is strong binding in ELISA.

Clones were tested for their ability to bind cyclic peptide, linear peptide, A-beta 1-42 monomer and A-beta 1-42 oligomers prepared as described above. Binding assays were performed using MASS-1 as described above (Direct binding assays). A number of clones were selected based on the binding assays performed as shown in Table 1.

The selected clones were IgG mAb. Negative numbers in the primary screen are indicative of no binding (e.g. less than isotype control).

TABLE 1

| | 305 | | | |
|---|---|---|---|---|
| | Cyclic-Peptide (RU) | Linear-Peptide (RU) | A β 42 Monomer (RU) | A β 42 Oligomer (RU) |
| 2A8 | 333.1 | −6.1 | −13.5 | 76.6 |
| 3D8 | 639.7 | 5.7 | −20.9 | 45 |
| 4C2 | 362.2 | −4.3 | −34 | 161.6 |
| 4C12 | 433.3 | | 24.7 | 73.1 |
| 5D3 | 292.7 | 19.1 | −12.8 | 47.4 |
| 5G1 | 295.5 | 120.5 | −17.6 | 46.2 |
| 6E3 | 211 | 12.4 | −36.6 | 77.5 |
| 7E9 | 495.4 | 7.7 | −55.1 | 86 |
| 8H10 | 533.7 | 83.8 | −32.8 | 68.5 |
| 9F3 | 304.6 | 36.4 | −7.2 | 56.6 |
| 10B6 | 263.3 | 9.3 | −13.4 | 71.9 |
| 12D5 | 259.8 | −3.2 | −7 | 31.7 |
| 12F4 | 554.8 | −0.8 | 38.7 | 89.2 |

ELISA Prescreen

The ELISA prescreen of hybridoma supernatants identified clones that showed increased binding to the cyclic peptides compared to the linear peptide. A proportion of the clones were reactive to KLH-epitope linker peptide. These were excluded from further investigation. The majority of the clones were determined to be of the IgG isotype using the isotyping procedure described herein.

Direct Binding Measured by Surface Plasmon Resonance—Primary Screen

Using surface plasmon resonance the antibody clone containing tissue culture supernatants were tested for direct binding to cyclic peptide, linear peptide, A-beta oligomer and A-beta monomer.

Figure 15:
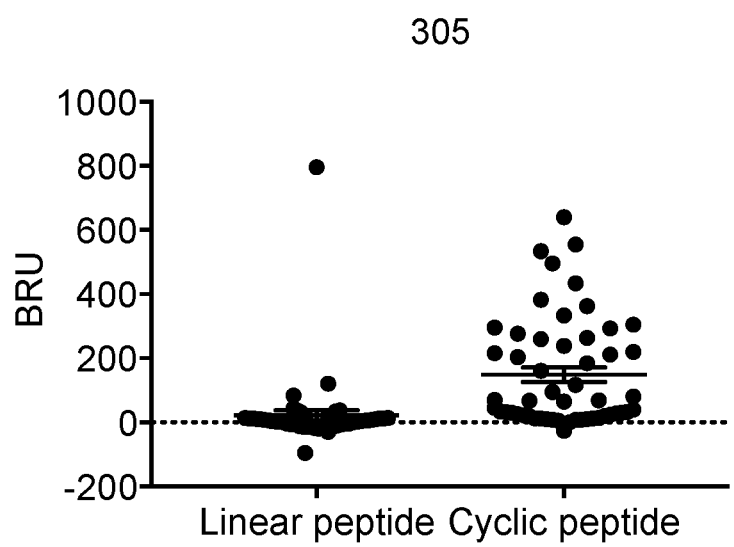
FIG. 15: Surface plasmon resonance (SPR) direct binding assay of tissue culture supernatant clones to cyclic peptide and linear peptide in Panel A, and A-beta oligomer and A-beta monomer in Panel B.
Figure 15:
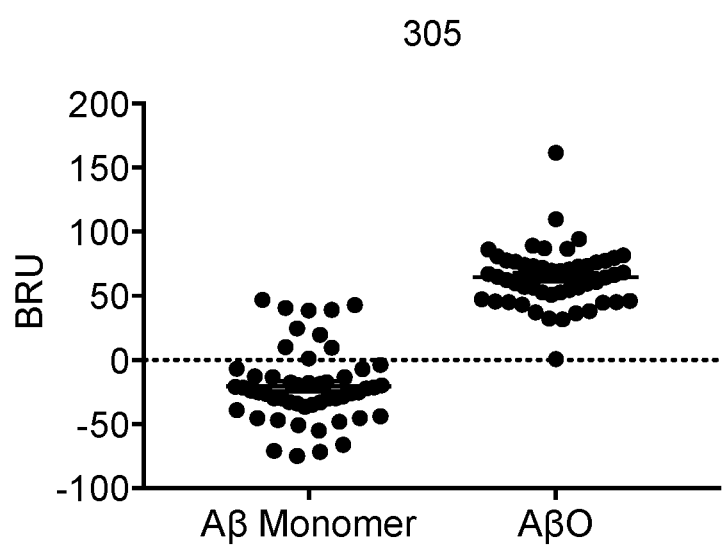

The results for are shown in FIG. 15. Panel A shows antibody binding to cyclic peptide and to linear peptide (unstructured), for IgG clones that are not reactive to the linker region. Panel B shows antibody binding to A-beta oligomer and A-beta monomer. A number of the clones have elevated reactivity to the cyclic peptide and all clones have minimal or no reactivity to linear peptide, except for one. There is a general selectivity for A-beta oligomer binding.

Figure 17:
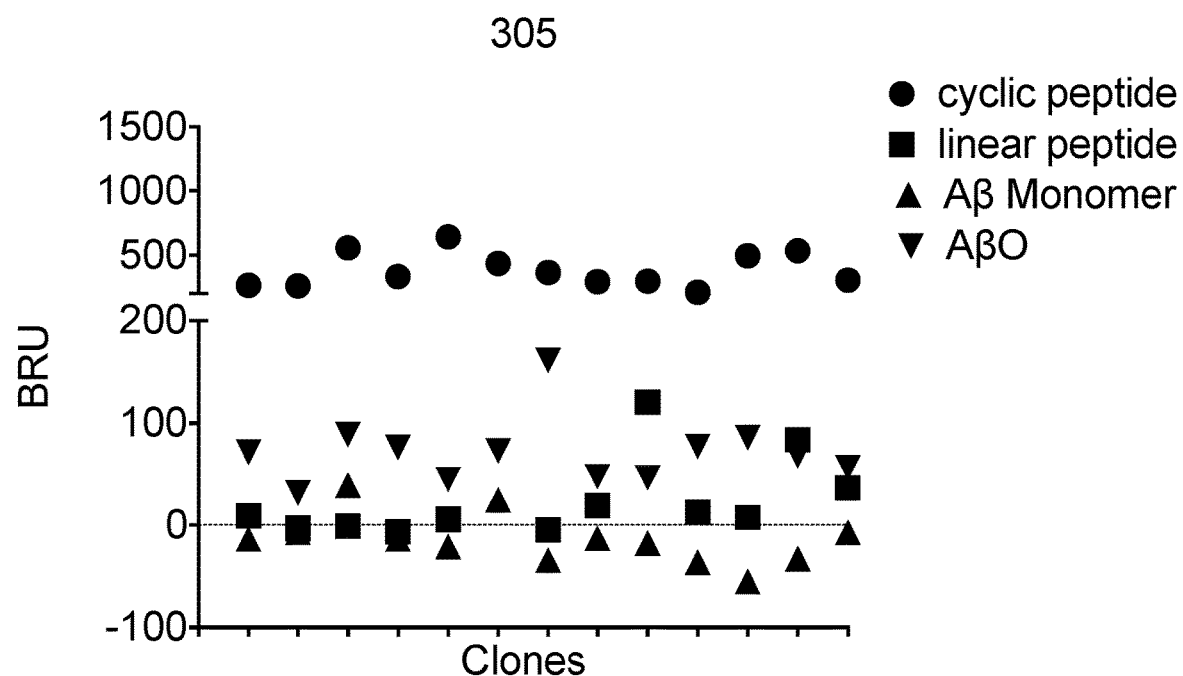
FIG. 17: SPR direct binding assay of select clones to cyclic peptide, linear peptide, A-beta monomer, and A-beta oligomer.

For select clones comparative binding profile is shown in FIG. 17. Each clone is assessed for direct binding using surface plasmon resonance against specific epitope in the context of cyclic peptide (circle), linear peptide (square), A-beta (Aβ) monomer (upright triangle), and A-beta oligomer (AβO) (upside-down triangle).

Example 9

Secondary Screen
Immunohistochemistry

Immunohistochemistry was performed on frozen human brain sections, with no fixation or antigen retrieval. In a humidified chamber, non-specific staining was blocked by incubation with serum-free protein blocking reagent (Dako Canada Inc., Mississauga, ON, Canada) for 1 h. The following primary antibodies were used for immunostaining: mouse monoclonal isotype controls IgG1, IgG2a, and IgG2b, and anti-amyloidβ 6E10, all purchased from Biolegend, and selected purified clones reactive to the cyclopeptide. All antibodies were used at 1 μg/mL. Sections were incubated at room temperature for 1 h, and washed 3×5 min in TBS-T. Anti-Mouse IgG Horseradish Peroxidase conjugated (1:1000, ECL) was applied to sections and incubated 45 min, then washed 3×5 min in TBS-T. DAB chromogen reagent (Vector Laboratories, Burlington ON, Canada) was applied and sections rinsed with distilled water when the desired level of target to background staining was achieved. Sections were counterstained with Mayer's haematoxylin, dehydrated and cover slips were applied. Slides were examined under a light microscope (Zeiss Axiovert 200M, Carl Zeiss Canada, Toronto ON, Canada) and representative images captured at 20 and 40× magnification using a Leica DC300 digital camera and software (Leica Microsystems Canada Inc., Richmond Hill, ON). Images were optimized in Adobe Photoshop using Levels Auto Correction.

CSF and Brain Extracts

Human brain tissues were obtained from the University of Maryland Brain and Tissue Bank upon approval from the UBC Clinical Research Ethics Board (C04-0595). CSFs were obtained from patients assessed at the UBC Hospital Clinic for Alzheimer's and Related Disorders. The study was approved by the UBC Clinical Research Ethics Board, and written consent from the participant or legal next of kin was obtained prior to collection of CSF samples. Clinical diagnosis of probable AD was based on NINCDS-ADRDA criteria. CSFs were collected in polypropylene tubes, processed, aliquoted into 100 μL polypropylene vials, and stored at −80° C. within 1 hour after lumbar puncture.

Homogenization: Human brain tissue samples were weighed and subsequently submersed in a volume of fresh, ice cold TBS and EDTA-free protease inhibitor cocktail from Roche Diagnostics (Laval QC, Canada) such that the final concentration of brain tissue was 20% (w/v). Tissue was homogenized in this buffer using a mechanical probe homogenizer (3×30 sec pulses with 30 sec pauses in between, all performed on ice). TBS homogenized samples were then subjected to ultracentrifugation (70,000×g for 90 min). Supernatants were collected, aliquoted and stored at −80° C. The protein concentration of TBS homogenates was determined using a BCA protein assay (Pierce Biotechnology Inc, Rockford Ill., USA).

CSF: CSF was pooled from 9 donors with AD and 9 donors without AD. Samples were analyzed by SPR using purified IgG at a concentration of 30 micrograms/ml for all antibodies. Mouse IgG was used as an antibody control and all experiments were repeated at least 2 times.

Positive binding in CSF and brain extracts was confirmed using antibody 6E10.

SPR Analysis: 4 brain extracts from AD patients and 4 brain extracts from age-matched controls were pooled and analyzed. Brain samples, homogenized in TBS, included frontal cortex Brodmann area 9. All experiments were performed using a Molecular Affinity Screening System (MASS-1) (Sierra Sensors GmbH, Hamburg, Germany), an analytical biosensor that employs high intensity laser light and high speed optical scanning to monitor binding interactions in real time as described in Example 6. Purified antibodies generated for cyclopeptides described herein were captured on separate flow cells of a protein A-derivatized sensor chip and diluted samples injected over the surfaces for 180 seconds, followed by 120 seconds of dissociation in buffer and surface regeneration. Binding responses were double-referenced by subtraction of mouse control IgG reference surface binding and assay buffer, and the different groups of samples compared.

Results

CSF Brain Extracts and Immunohistochemistry

Several clones were tested for their ability to bind A-beta in CSF, soluble brain extracts and tissue samples of cavaderic AD brains are shown in Table 2. Strength of positivity in Table 2 is shown by the number plus signs.

Table 2 and Table 3 provide data for selected clone's binding selectivity for oligomers over monomer measured as described herein by SPR.

IHC results are also summarized in Table 2 where "+/−" denotes staining similar to or distinct from isotype control but without clear plaque morphology.

Figure 18:
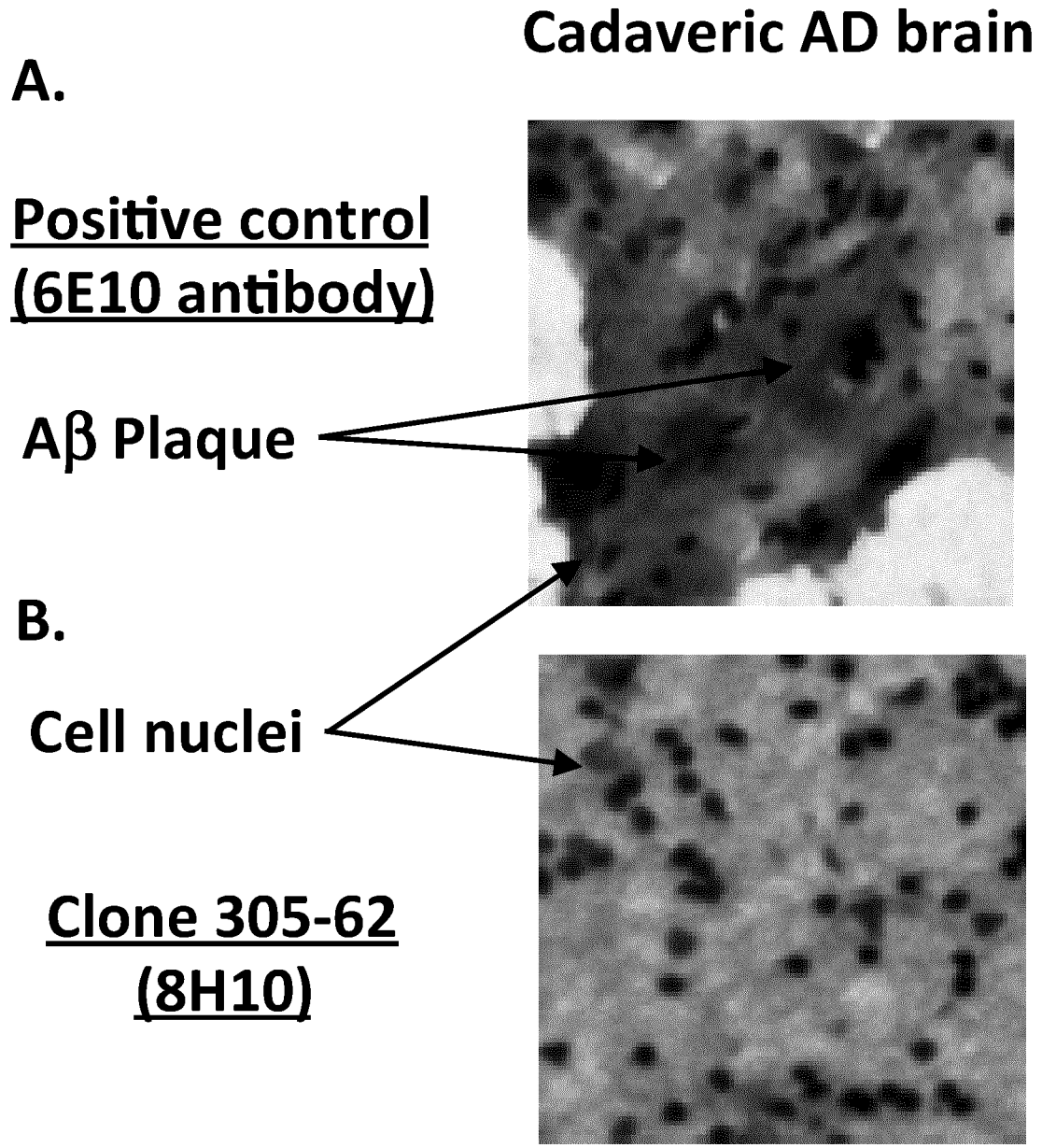
FIG. 18: Immunohistochemical staining of plaque from cadaveric AD brain using 6E10 positive control antibody (A) and a selected and purified antibody (305-62, 8H10) raised against cyclo(CGQKLVG) (SEQ ID NO: 3) (B).

FIG. 18 shows an example of the lack of plaque staining on fresh frozen sections with clone 8H10 (62) compared to the positive plaque staining seen with 6E10 antibody.

Figure 19:
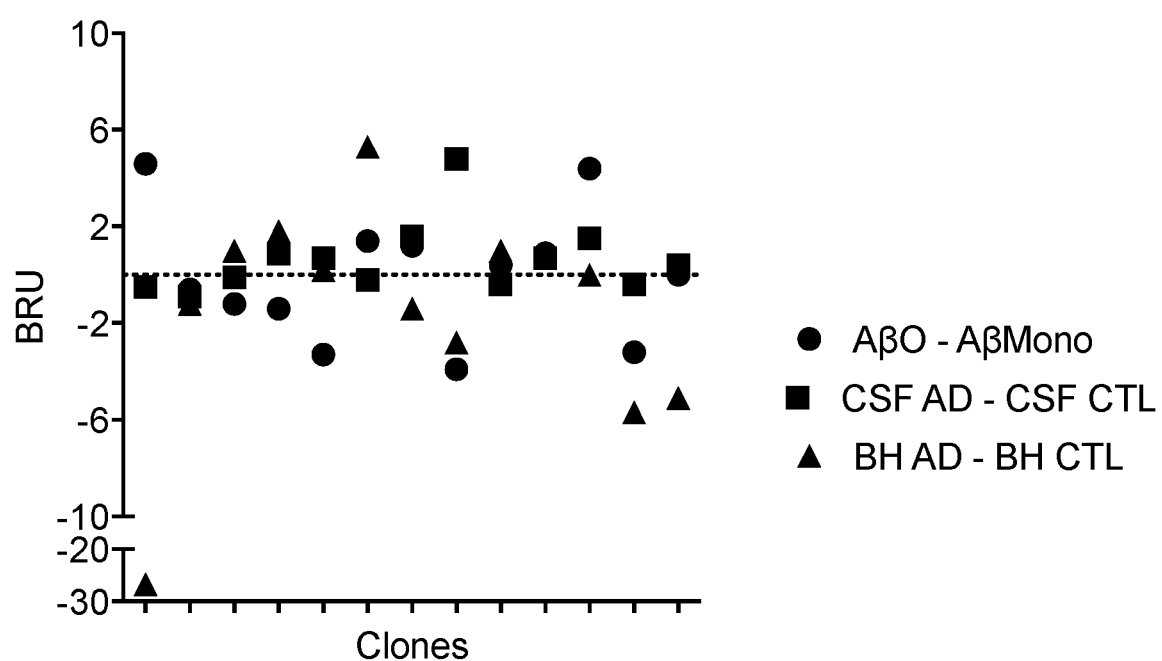
FIG. 19: Secondary screening of selected and purified antibodies using an SPR indirect (capture) binding assay. SPR binding response of A-beta oligomer to captured antibody minus binding response of A-beta monomer to captured antibody (circle); SPR binding response of pooled soluble brain extract (BH) from AD patients to captured antibody minus binding response of pooled brain extract from non-AD controls to captured antibody (triangle); SPR binding response of pooled cerebrospinal fluid (CSF) from AD patients to captured antibody minus binding response of pooled CSF from non-AD controls to captured antibody (square).

FIG. 19 shows, antibodies raised to the cyclopeptide comprising QKLV (SEQ ID NO: 1) bound A-beta oligomer preferentially over monomer and also preferentially bound A-beta in brain extracts and/or CSF of AD patients.

As shown in Tables 2, 3 and FIGS. 18 and 19, antibodies raised to the cyclopeptide comprising QKLV (SEQ ID NO: 1) included clones that bound A-beta in brain extracts and/or CSF, but did not appreciably bind to monomers on SPR, and did not appreciably bind to plaque fibrils by IHC.

TABLE 2

Summary of binding characteristics

| | Clone # | Oligomers/ Monomers | CSF AD/Non-AD | Brain Extract AD/Non-AD | IHC - Plaque Staining |
|---|---|---|---|---|---|
| cyclo (CGQKLVG) (SEQ ID NO: 3) | 305-59 (5G1) | + | − | ++ | +/− |
| | 305-61 (7E9) | − | ++ | − | − |
| | 305-62 (8H10) | +/− | − | + | − |

*Scoring is relative to other clones in the same sample category.

TABLE 3

A-beta Oligomer binding RU values subtracted for monomer binding

| Clone tested | 305-62 (8H10) |
|---|---|
| RU | 0.4 |

Example 10

Synthetic Oligomer Binding

Figure 20:
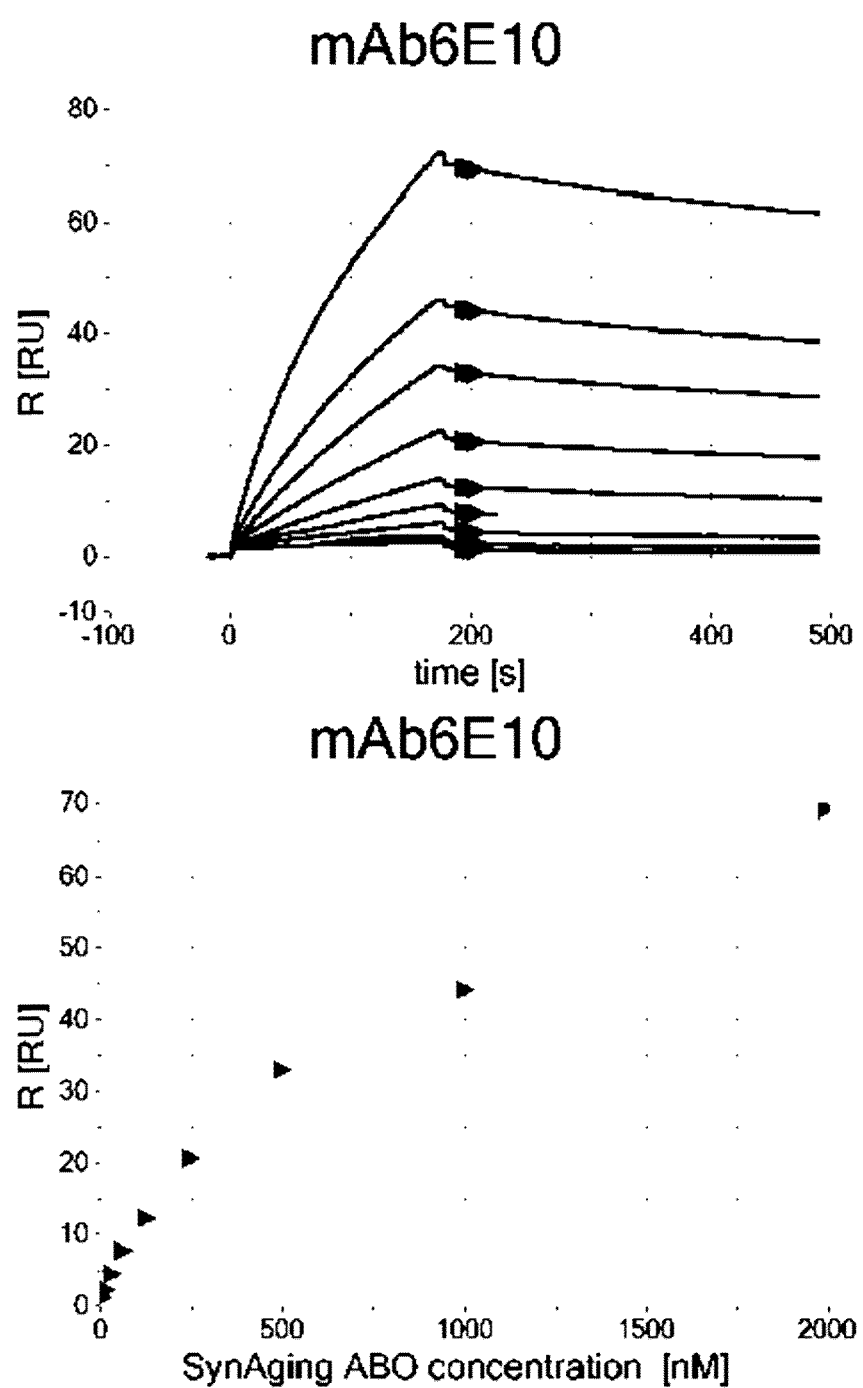
FIG. 20: Verification of antibody binding to stable A-beta oligomers. SPR sensorgrams and binding response plots of varying concentrations of commercially-prepared stable A-beta oligomers binding to immobilized antibodies. Panel A shows results with the positive control mAb6E10, Panel B with the negative isotype control and Panel C with antibody raised against cyclo (CGQKLVG) (SEQ ID NO: 3). Panel D plots binding of selected antibody clones raised against cyclic peptide comprising QKLV (SEQ ID No: 1), with A-beta oligomer at a concentration of 1 micromolar.
Figure 20:
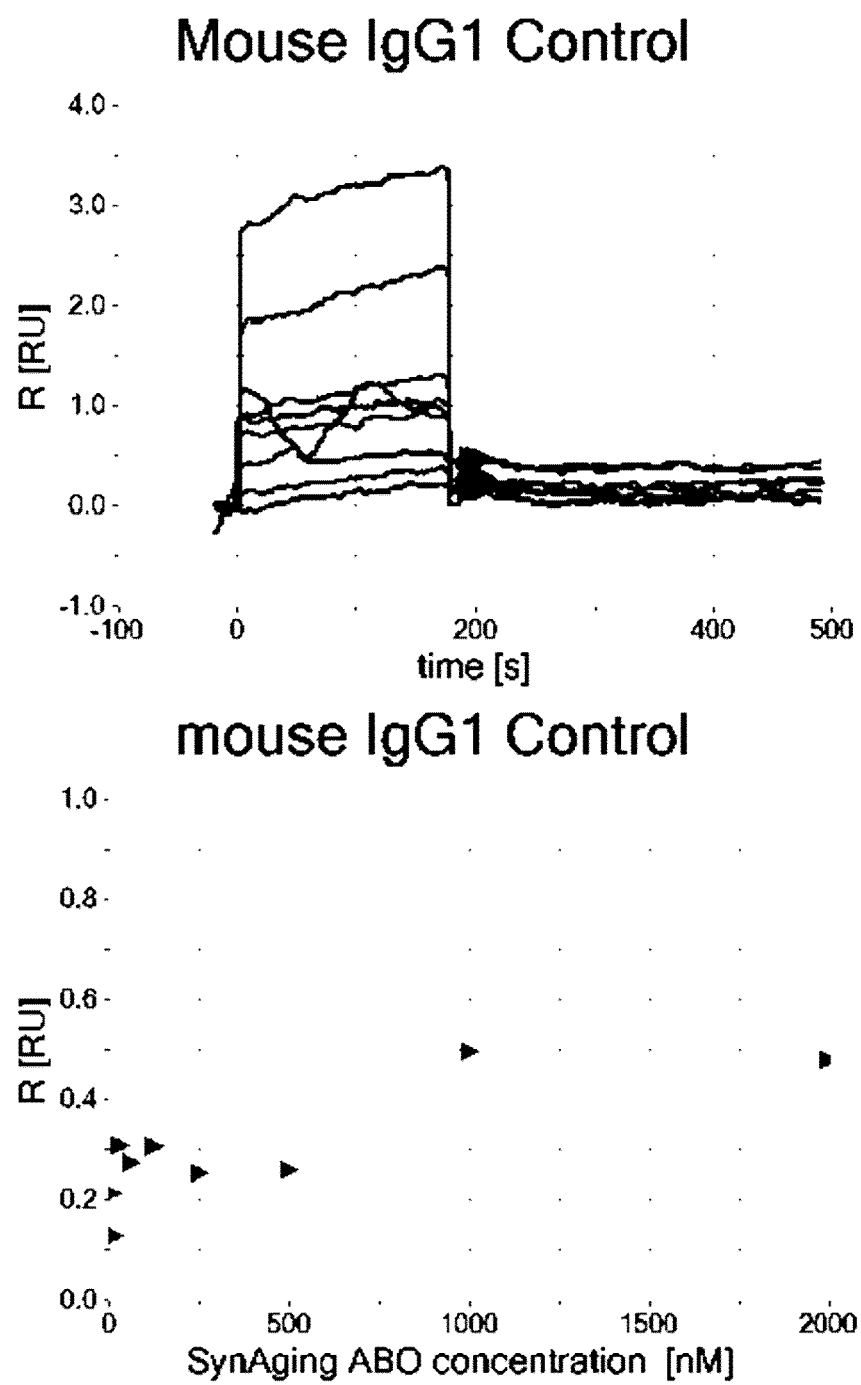
Figure 20:
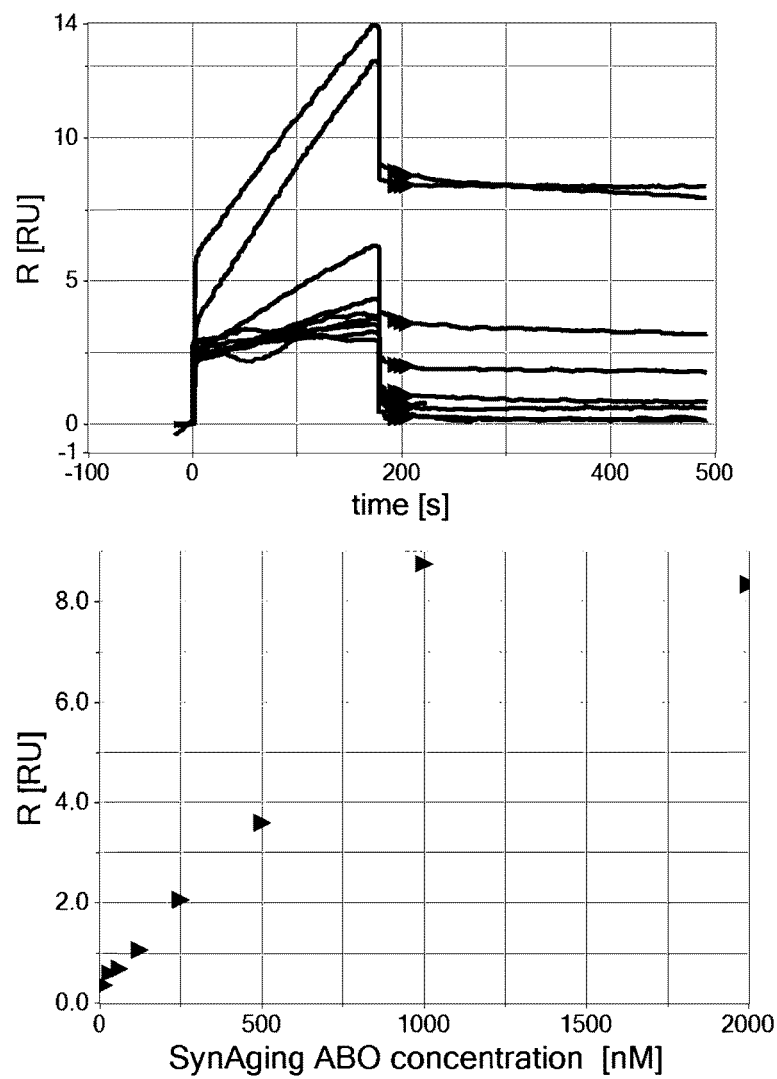
Figure 20:
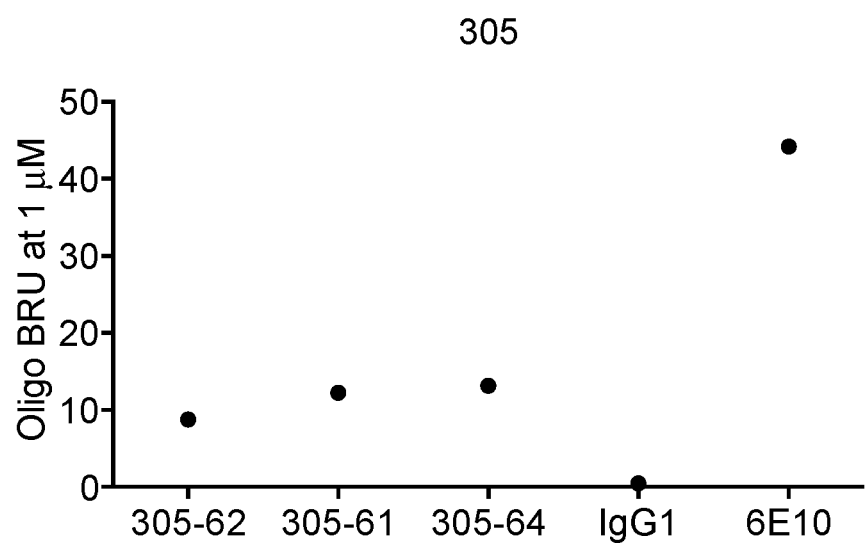

Serial 2-fold dilutions (7.8 nM to 2000 nM) of commercially-prepared synthetic amyloid beta oligomers (SynAging SAS, Vandceuvre-lés-Nancy, were tested for binding to covalently immobilized antibodies. Results for control antibody mAb6E10 is shown in FIG. 20A and mouse control IgG control is shown in FIG. 20B. FIG. 20 C shows results using an antibody raised against cyclo(CGQKLVG) (SEQ ID NO:3).

Example 11

Immunohistochemistry on Formalin Fixed Tissues

Human brain tissue was assessed using antibodies raised to cyclo CGQKLVG (SEQ ID NO: 3). The patient had been previously characterized and diagnosed with Alzheimer's disease with a tripartite approach: (i) Bielschowsky silver method to demonstrate senile plaques and neurofibrillary tangles, (ii) Congo red to demonstrate amyloid and (iii) tau immunohistochemistry to demonstrate tangles and to confirm the senile plaques are "neuritic". This tissue was used to test plaque reactivity of selected monoclonal antibody clones. The brain tissues were fixed in 10% buffered formalin for several days and paraffin processed in the Sakura VIP tissue processors. Tissue sections were probed with 1 μg/ml of antibody with and without microwave antigen retrieval (AR). The pan-amyloid beta reactive antibody 6E10 was included along with selected antibody clones as a positive control. Antibodies were diluted in Antibody Diluent (Ventana), color was developed with OptiView DAB (Ventana). The staining was performed on the Ventana Benchmark XT IHC stainer. Images were obtained with an Olympus BX45 microscope. Images were analyzed blind by a professional pathologist with expertise in neuropathology.

As shown in Table 4 below, using fixed tissue, the tested antibodies were negative for specific staining of senile plaque amyloid with or without antigen retrieval. 6E10 was used as the positive control.

TABLE 4

| | | Convincing evidence of specific staining of senile plaque amyloid | |
|---|---|---|---|
| Epitope | Antibodies to test | Without AR | Plus AR |
| 305 | 59 (5G1) | possible weak staining | Neg |
| | 61 (7E9) | Neg | Neg |
| | 62 (8H10) | Neg | Neg |
| Positive Control | 6E10 | Strongly positive | Strongly positive |

Example 12

Inhibition of Oligomer Propagation

The biological functionality of antibodies was tested in vitro by examining their effects on Amyloid Beta (Aβ) aggregation using the Thioflavin T (ThT) binding assay. Aβ aggregation is induced by and propagated through nuclei of preformed small Aβ oligomers, and the complete process from monomeric Aβ to soluble oligomers to insoluble fibrils is accompanied by concomitantly increasing beta sheet formation. This can be monitored by ThT, a benzothiazole salt, whose excitation and emission maxima shifts from 385 to 450 nm and from 445 to 482 nm respectively when bound to beta sheet-rich structures and resulting in increased fluorescence Briefly, Aβ 1-42 (Bachem Americas Inc., Torrance, Calif.) was solubilized, sonicated, diluted in Tris-EDTA buffer (pH 7.4) and added to wells of a black 96-well microtitre plate (Greiner Bio-One, Monroe, N.C.) to which equal volumes of cyclopeptide raised antibody or irrelevant mouse IgG antibody isotype controls were added, resulting in a 1:5 molar ratio of Aβ1-42 peptide to antibody. ThT was added and plates incubated at room temperature for 24 hours, with ThT fluorescence measurements (excitation at 440 nm, emission at 486 nm) recorded every hour using a Wallac Victor3v 1420 Multilabel Counter (PerkinElmer, Waltham, Mass.). Fluorescent readings from background buffer were subtracted from all wells, and readings from antibody only wells were further subtracted from the corresponding wells. As shown in FIG. 21, Aβ42 aggregation, as monitored by ThT fluorescence, demonstrated a sigmoidal shape characterized by an initial lag phase with minimal fluorescence, an exponential phase with a rapid increase in fluorescence and finally a plateau phase during which the Aβ molecular species are at equilibrium and during which there is no increase in fluorescence. Co-incubation of Aβ42 with an irrelevant mouse antibody did not have any significant effect on the aggregation process. In contrast, co-incubation of Aβ42 with the test antibodies completely inhibited all phases of the aggregation process. Results obtained with antibody clones 61, 62 and 64 are shown in FIG. 21. As the ThT aggregation assay mimics the in vivo biophysical/ biochemical stages of Aβ propagation and aggregation from monomers, oligomers, protofibrils and fibrils that is pivotal in AD pathogenesis, the antibodies raised to cyclo CGQKLVG (SEQ ID NO: 3) demonstrate the potential to completely abrogate this process. Isotype control performed using mouse IgG control showed no inhibition

Example 13

Achieving the optimal profile for Alzheimer's immunotherapy: Rational generation of antibodies specific for toxic A-beta oligomers Objective: Generate antibodies specific for toxic amyloid-β oligomers (AβO)

Background: Current evidence suggests that propagating prion-like strains of AβO, as opposed to monomers and fibrils, are preferentially toxic to neurons and trigger tau pathology in Alzheimer's disease (AD). In addition, dose-limiting adverse effects have been associated with Aβ fibril recognition in clinical trials. These observations suggest that specific neutralization of toxic AβOs may be desirable for safety and efficacy.

Design/Methods: Computational simulations were employed as described herein, using molecular dynamics with standardized force-fields to perturb atomic-level structures of Aβ fibrils deposited in the Protein Data Base. It was hypothesized that weakly-stable regions are likely to be exposed in nascent protofibrils or oligomers. Clustering analysis, curvature, exposure to solvent, solubility, dihedral angle distribution, and Ramachandran angle distributions were all used to characterize the conformational properties of predicted epitopes, which quantify differences in the antigenic profile when presented in the context of the oligomer vs the monomer or fibril. The candidate peptide epitopes were synthesized in a cyclic format that may mimic regional AβO conformation, conjugated to a carrier protein, and used to generate monoclonal antibodies in mice. Purified antibodies were screened by SPR and immunohistochemistry.

Results

Sixty-six IgG clones against 5 predicted epitopes were selected for purification based on their ability to recognize the cognate structured peptide and synthetic AβO, with little or no binding to unstructured peptide, linker peptide, or Aβ monomers. Additional screening identified antibodies that preferentially bound to native soluble AβO in CSF and brain extracts of AD patients compared to controls. Immunohistochemical analysis of AD brain allowed for selection of antibody clones that do not react with plaque.

Conclusion: Computationally identified AβO epitopes allowed for the generation of antibodies with the desired target profile of selective binding to native AD AβOs with no significant cross-reactivity to monomers or fibrils.

Example 14

Toxicity Inhibition Assay

The inhibition of toxicity of A-beta42 oligomers by antibodies raised to the cyclopeptide can be tested in a rat primary cortical neuron assay.

Antibody and control IgG are each adjusted to a concentration such as 2 mg/mL. Various molar ratios of A-beta oligomer and antibody are tested along with a vehicle control, A-beta oligomer alone and a positive control such as the neuroprotective peptide humanin HNG.

An exemplary set up is shown in Table 5.

Following preincubation for 10 minutes at room temperature, the volume is adjusted to 840 microlitres with culture medium. The solution is incubated for 5 min at 37 C. The solution is then added directly to the primary cortical neurons and cells are incubated for 24 h. Cell viability can be determined using the MTT assay.

TABLE 5

| AβO/AB molar ratio | AβO (μL) | AβO (μM) | AB (μM) | AB (μL) | Medium (μL) | Final volume (μL) |
|---|---|---|---|---|---|---|
| 5/1 | 1.68 | 4.2 | 0.84 | 12.73 | 185.6 | 200 |
| 1/1 | 1.68 | 4.2 | 4.20 | 63.64 | 134.7 | 200 |
| 1/2 | 1.68 | 4.2 | 8.4 | 127.27 | 71.1 | 200 |

AβO working solution: 2.2 mg/mL-500 μM
CTRL vehicle: 1.68 μL of oligomer buffer + 127.3 μL PBS + 711 μL culture medium
CTRL AβO: 1.68 μL of AβO + 127.3 μL PBS + 711 μL culture medium
CTRL HNG: 1.68 μL of AβO + 8.4 μL HNG (100 nM final) + 127.3 μL PBS + 702.6 μL culture medium This test was conducted using 305 antibody clone 62. The antibody alone showed no toxicity (FIG. 22A). Dosage-independent inhibition of A-beta oligomer toxicity was observed for all concentrations of antibody to oligomer: 1:5, 1:1 and 2:1 (FIG. 22B).

Example 15

In Vivo Toxicity Inhibition Assay

The inhibition of toxicity of A-beta42 oligomers by antibodies raised to the cyclopeptide can be tested in vivo in mouse behavioral assays.

The antibody and an isotype control are each pre-mixed with A-beta42 oligomers at 2 or more different molar ratios prior to intracerebroventricular (ICV) injection into mice. Control groups include mice injected with vehicle alone, oligomers alone, antibody alone, and a positive control such as the neuroprotective peptide humanin. Alternatively, the antibodies can be administered systemically prior to, during, and/or after ICV injection of the oligomers. Starting approximately 4-7 days post ICV injection of oligomers, cognition is assessed in behavioral assays of learning and memory such as the mouse spatial recognition test (SRT), Y-Maze assay, Morris water maze model and novel object recognition model (NOR).

The mouse spatial recognition test (SRT) assesses topographical memory, a measure of hippocampal function (SynAging). The model uses a two-chamber apparatus, in which the chambers differ in shape, pattern and color (i.e. topographical difference). The chambers are connected by a clear Plexiglass corridor. Individual mice are first placed in the apparatus for a 5 min exploration phase where access to only one of the chambers is allowed. Mice are then returned to their home cage for 30 min and are placed back in the apparatus for a 5 min "choice" phase during which they have access to both chambers. Mice with normal cognitive function remember the previously explored chamber and spend more time in the novel chamber. A discrimination index (DI) is calculated as follows: DI=(TN−TF)/(TN+TF), in which TN is the amount of time spent in the novel chamber and TF is the amount of time spent in the familiar chamber. Toxic A-beta oligomers cause a decrease in DI which can be partially rescued by the humanin positive control. Performance of this assay at different time points post ICV injection can be used to evaluate the potential of antibodies raised to the cyclopeptide to inhibit A-beta oligomer toxicity in vivo.

The Y-maze assay (SynAging) is a test of spatial working memory which is mainly mediated by the prefrontal cortex (working memory) and the hippocampus (spatial component). Mice are placed in a Y-shaped maze where they can explore 2 arms. Mice with intact short-term memory will alternate between the 2 arms in successive trials. Mice injected ICV with toxic A-beta oligomers are cognitively impaired and show random behavior with alternation close to a random value of 50% (versus ~70% in normal animals). This impairment is partially or completely reversed by the cholinesterase inhibitor donepezil (Aricept) or humanin, respectively. This assay provides another in vivo assessment of the protective activity of test antibodies against A-beta oligomer toxicity.

The Morris water maze is another widely accepted cognition model, investigating spatial learning and long-term topographical memory, largely dependent on hippocampal function (SynAging). Mice are trained to find a platform hidden under an opaque water surface in multiple trials. Their learning performance in recalling the platform location is based on visual clues and video recorded. Their learning speed, which is the steadily reduced time from their release into the water until finding the platform, is measured over multiple days. Cognitively normal mice require less and less time to find the platform on successive days (learning). For analyzing long-term memory, the test is repeated multiple days after training: the platform is taken away and the number of crossings over the former platform location, or the time of the first crossing, are used as measures to evaluate long-term memory. Mice injected ICV with toxic A-beta oligomers show deficits in both learning and long-term memory and provide a model for evaluating the protective activity of test antibodies.

The Novel Object Recognition (NOR) model utilizes the normal behavior of rodents to investigate novel objects for a significantly longer time than known objects, largely dependent on perirhinal cortex function (SynAging). Mice or rats are allowed to explore two identical objects in the acquisition trial. Following a short inter-trial interval, one of the objects is replaced by a novel object. The animals are returned to the arena and the time spent actively exploring each object is recorded. Normal rodents recall the familiar object and will spend significantly more time exploring the novel object. In contrast, A-beta oligomer-treated rodents exhibit clear cognitive impairment and will spend a similar amount of time investigating both the 'familiar' and 'novel' object. This can be transiently reversed with known clinical cognitive enhancers (e.g. donepezil). The NOR assay can be performed multiple times in longitudinal studies to assess the potential cognitive benefit of test antibodies.

In addition to behavioral assays, brain tissue can be collected and analyzed for levels of synaptic markers (PSD95, SNAP25, synaptophysin) and inflammation markers (IL-1-beta). Mice are sacrificed at ~14 days post-ICV injection of oligomers and perfused with saline. Hippocampi are collected, snap frozen and stored at −80° C. until analyzed. Protein concentrations of homogenized samples are determined by BCA. Concentration of synaptic markers are determined using ELISA kits (Cloud-Clone Corp, USA). Typically, synaptic markers are reduced by 25-30% in mice injected with A-beta oligomers and restored to 90-100% by the humanin positive control. Concentrations of the IL-1-beta inflammatory markers are increased approximately 3-fold in mice injected with A-beta oligomers and this increase is largely prevented by humanin. These assays provide another measure of the protective activity of test antibodies at the molecular level.

Example 16

In vivo Propagation Inhibition Assay

In vivo propagation of A-beta toxic oligomers and associated pathology can be studied in various rodent models of Alzheimer's disease (AD). For example, mice transgenic for human APP (e.g. APP23 mice) or human APP and PSEN1 (APPPS1 mice) express elevated levels of A-beta and exhibit gradual amyloid deposition with age accompanied by inflammation and neuronal damage. Intracerebral inoculation of oligomer-containing brain extracts can significantly accelerate this process13, 14). These models provide a system to study inhibition of A-beta oligomer propagation by test antibodies administered intracerebrally or systemically.

Example 17

CDR Sequencing-305-7E9.1

305-7E9.1 which was determined to have an IgG3 heavy chain and a kappa light chain was selected for CDR and variable regions of the heavy and light chains.

RT-PCR was carried out using 5' RACE and gene specific reverse primers which amplify the appropriate mouse immunoglobulin heavy chain (IgG1/IgG3/IgG2A) and light chain (kappa) variable region sequences.

The specific bands were excised and cloned into pCR-Blunt II-TOPO vector for sequencing, and the constructs were transformed into E. coli At least 8 colonies of each chain were picked & PCR screened for the presence of amplified regions prior to sequencing. Selected PCR positive clones were sequenced.

The CDR sequences are in Table 6. The consensus DNA sequence and protein sequences of the variable portion of the heavy and light chain are provided in Table 7.

TABLE 6

| Chain | CDR | Sequence | SEQ ID NO |
|---|---|---|---|
| Heavy | CDR-H1 | GYTFTDYE | 11 |
|  | CDR-H2 | IDPETGDT | 12 |
|  | CDR-H3 | TSPIYYDYDWFAY | 13 |
| Light | CDR-L1 | QSLLNNRTRKNY | 14 |
|  | CDR-L2 | WAS | 15 |
|  | CDR-L3 | KQSYNLRT | 16 |

TABLE 7

Consensus DNA sequence and translated protein sequences of the variable region. The complementarity determining regions (CDRs) are underlined according to IMTG/LIGM-DB.

| Isotype | Consensus DNA Sequence | Protein sequence |
|---|---|---|
| IgG3<br>SEQ ID NO:<br>17, 18 | ATGGAATGGAGCTGGGTCTTTCTCTTCCTCCTGTCAGTAATTGCAGGTG<br>TCCAATCCCAGGTTCAACTGCAGCAGTCTGGGGCTGAGCTGGTGAGGC<br>CTGGGGCTTCAGTGACGCTGTCCTGCAAGGCTTCGGGCTACACATTTA<br>CTGACTATGAAATGCACTGGGTGAAGCAGACACCTGTGCATGGCCTGG<br>AATGGATTGGAGCTATTGATCCTGAAACTGGTGATACTGCCTACAATC<br>AGGAGTTCAAGGGCAAGGCCACACTGACTGCAGACAAATCCTCCAGCA<br>CAGCCTACATGGAGCTCCGCAGCCTGACATCTGAGGACTCTGCCGTCT<br>ATTACTGTACAAGCCCCATCTACTATGATTACGACTGGTTTGCTTACTG<br>GGGCCACGGGACTCTGGTCACTGTCTCTGCAGCTACAACAACAGCCCC<br>ATCT | MEWSWVFLFLLSVIAGV<br>QSQVQLQQSGAELVRPG<br>ASVTLSCKASGYTFTDYE<br>MHWVKQTPVHGLEWIG<br>AIDPETGDTAYNQEFKGK<br>ATLTADKSSSTAYMELRSL<br>TSEDSAVYYCTSPIYYDYD<br>WFAYWGHGTLVTVSAAT<br>TTAPS |
| Kappa<br>SEQ ID NO:<br>19, 20 | ATGGATTCACAGGCCCAGGTTCTTATATTGCTGCTGCTATGGGTATCTG<br>GTACCTGTGGGGACATTGTGATGTCACAGTCTCCATCCTCCCTGGCTGT<br>GTCAGCAGGAGAGAAGGTCACTATGAGCTGCAAATCCAGTCAGAGTC<br>TGCTCAACAATAGAACCCGAAAGAACTACTTGGCTTGGTACCAGCAG<br>AAACCAGGGCAGTCTCCTAAACTGCTGATCTACTGGGCATCCACTAGG<br>GAATCTGGGGTCCCTGATCGCTTCACAGGCAGTGGATCTGGGACAGAT<br>TTCACTCTCACCATCAGCAGTGTGCAGGCTGAAGACCTGGCAGTTTATT<br>ACTGCAAGCAATCTTATAATCTTCGGACGTTCGGTGGAGGCACCAAGC<br>TGGAAATCAAACGGGCTGATGCT | MDSQAQVLILLLLWVSGT<br>CGDIVMSQSPSSLAVSAG<br>EKVTMSCKSSQSLLNNRT<br>RKNYLAWYQQKPGQSPK<br>LLIYWASTRESGVPDRFT<br>GSGSGTDFTLTISSVQAED<br>LAVYYCKQSYNLRTFGGG<br>TKLEIKRADA |

Example 9

CDR sequencing—305-8H10

305-8H10 which was determined to have an IgG1 heavy chain and a kappa light chain was selected for sequencing CDR and variable regions of the heavy and light chains.

RT-PCR was carried out using 5' RACE and gene specific reverse primers which amplify the appropriate mouse immunoglobulin heavy chain (IgG1/IgG3/IgG2A) and light chain (kappa) variable region sequences.

The specific bands were excised and cloned into pCR-Blunt II-TOPO vector for sequencing, and the constructs were transformed into E. coli At least 8 colonies of each chain were picked & PCR screened for the presence of amplified regions prior to sequencing. Selected PCR positive clones were sequenced.

The CDR sequences are in Table 8. The consensus DNA sequence and protein sequences of the variable portion of the heavy and light chain are provided in Table 9.

TABLE 8

| Chain | CDR | Sequence | SEQ ID NO |
|---|---|---|---|
| Heavy | CDR-H1 | GFSLSTSGMG | 21 |
| | CDR-H2 | IWWDDDK | 22 |
| | CDR-H3 | ARSITTVVATPFDY | 23 |
| Light | CDR-L1 | QNVRSA | 24 |
| | CDR-L2 | LAS | 25 |
| | CDR-L3 | LQHWNSPFT | 26 |

TABLE 9

Consensus DNA sequence and translated protein sequences of the variable region. The complementarity determining regions (CDRs) are underlined according to IMTG/LIGM-DB.

| Isotype | Consensus DNA Sequence | Protein sequence |
|---|---|---|
| IgG1<br>SEQ ID NO:<br>27, 28 | ATGGACAGGCTTACTTCTTCATTCCTGCTGCTGATTGTCCCTGCA<br>TATGTCTTGTCCCAAGTTACTCTAAAAGAGTCTGGCCCTGGGATA<br>TTGAAGCCCTCACAGACCCTCAGTCTGACTTGTTCTTTCTCTGGG<br>TTTTCACTGAGCACTTCTGGTATGGGTGTAGGCTGGATTCGTCAG<br>CCTTCAGGGAAGGGTCTGGAGTGGCTGGCACACATTTGGTGGGAT<br>GATGATAAGTACTATAACCCATCCCTGAAGAGCCAGCTCACAATC<br>TCCAAGGATACCTCCAGAAACCAGGTATTCCTCAAGATCACCAGT<br>GTGGACACTGCAGATACTGCCACTTACTACTGTGCTCGAAGTATT<br>ACTACGGTAGTAGCTACGCCCTTTGACTACTGGGGCCAAGGCACC<br>ACTCTCACAGTCTCCTCAGCCAAAACGACAC | MDRLTSSFLLLIVPAY<br>VLSQVTLKESGPGILK<br>PSQTLSLTCSFSGFSL<br>STSGMGVGWIRQPSGK<br>GLEWLAHIWWDDDKYY<br>NPSLKSQLTISKDTSR<br>NQVFLKITSVDTADTA<br>TYYCARSITTVVATPF<br>DYWGQGTTLTVSSAKT<br>T |
| Kappa<br>SEQ ID NO:<br>29, 30 | ATGGGCATCAAGATGGAGTTTCAGACCCAGGTCTTTGTATTCGTG<br>TTGCTCTGGTTGTCTGGTGTTGATGGAGACATTGTGATGACCCAG<br>TCTCAAAAATTCATGTCCACATCAGTAGGAGACAGGGTCAGCATC<br>ACCTGCAAGGCCAGTCAGAATGTTCGTTCTGCTGTAGCCTGGTAT<br>CAACAGAAACCAGGGCAGTCTCCTAAAGCACTGATTTACCTGGCA<br>TCCAACCGGCACACTGGAGTCCCTGATCGCTTCACAGGCAGTGGA<br>TCTGGGACAGATTTCACTCTCACCATTAGCAATGTGCATTCTGAA | MGIKMEFQTQVFVFVL<br>LWLSGVDGDIVMTQSQ<br>KFMSTSVGDRVSITCK<br>ASQNVRSAVAWYQQKP<br>GQSPKALIYLASNRHT<br>GVPDRFTGSGSGTDFT<br>LTISNVHSEDLTDYFC |

TABLE 9-continued

Consensus DNA sequence and translated protein sequences of the variable region. The complementarity determining regions (CDRs) are underlined according to IMTG/LIGM-DB.

| Isotype | Consensus DNA Sequence | Protein sequence |
|---|---|---|
| | GACCTGACAGATTATTTCTGTCTGCAACATTGGAATTCTCCGTTC ACGTTCGGAGGGGGGACCAAGCTGGAAATAAAACGGGCTGATGCT | LQHWNSPFTFGGGTKL EIKRADA |

TABLE 10

A-beta Sequences and A beta sequences with linker

QKLV (SEQ ID NO: 1)

HQKLV (SEQ ID NO: 2)

CGQKLVG, cycloCGQKLVG (SEQ ID NO: 3)

GQKLV (SEQ ID NO: 4)

GQKLVG (SEQ ID NO: 5)

GGQKLVG (SEQ ID NO: 6)

GQKLVGG (SEQ ID NO: 7)

CGQKLVGC (SEQ ID NO: 8)

HQKLVF (SEQ ID NO: 9)

QKLVF (SEQ ID NO: 10)

TABLE 11

Full A-beta 1-42

DAEFRHDSGYEVHHQKLVFFAEDVGSNKGAIIGLMVGGVVIA (SEQ ID NO: 31)

While the present application has been described with reference to what are presently considered to be the preferred examples, it is to be understood that the application is not limited to the disclosed examples. To the contrary, the application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Specifically, the sequences associated with each accession numbers provided herein including for example accession numbers and/or biomarker sequences (e.g. protein and/or nucleic acid) provided in the Tables or elsewhere, are incorporated by reference in its entirety.

The scope of the claims should not be limited by the preferred embodiments and examples, but should be given the broadest interpretation consistent with the description as a whole.

CITATIONS FOR REFERENCES REFERRED TO IN THE SPECIFICATION

[1] SCIENTIFIC REPORTS|5: 9649|DOI: 10.1038/srep09649

[2] Vincent J. Hilser and Ernesto Freire. Structure-based calculation of the equilibrium folding pathway of proteins. correlation with hydrogen exchange protection factors. J. Mol. Biol., 262:756-772, 1996. The COREX approach.

[3] Samuel I. A. Cohen, Sara Linse, Leila M. Luheshi, Erik Hellstrand, Duncan A. White, Luke Rajah, Daniel E. Otzen, Michele Vendruscolo, Christopher M. Dobson, and Tuomas P. J. Knowles. Proliferation of amyloid-β42 aggregates occurs through a secondary nucleation mechanism. Proc. Natl. I Acad. Sci. USA, 110(24):9758-9763, 2013.

[4] Pietro Sormanni, Francesco A. Aprile, and Michele Vendruscolo. The camsol method of rational design of protein mutants with enhanced solubility. Journal of Molecular Biology, 427(2):478-490, 2015.

[5] Deborah Blacker, MD, ScD; Marilyn S. Albert, PhD; Susan S. Bassett, PhD; Rodney C. P. Go, PhD; Lindy E. Harrell, MD, PhD; Marshai F. Folstein, MD Reliability and Validity of NINCDS-ADRDA Criteria for Alzheimer's Disease The National Institute of Mental Health Genetics Initiative. Arch Neurol. 1994; 51(12):1198-1204. doi:10.1001/archneur.1994.00540240042014.

[6] Hamley, I. W. PEG-Peptide Conjugates 2014; 15, 1543-1559; dx.doi.org/10.1021/bm500246w

[7] Roberts, M J et al Chemistry for peptide and protein PEGylation 64: 116-127.

The invention claimed is:

1. An isolated antibody or antigen-binding fragment thereof that specifically binds to a cyclic A-beta peptide comprising the amino acid sequence of SEQ ID NO: 3, the antibody or antigen-binding fragment thereof comprising a light chain variable region and a heavy chain variable region, the heavy chain variable region comprising complementarity determining regions CDR-H1, CDR-H2 and CDR-H3, the light chain variable region comprising complementarity determining region CDR-L1, CDR-L2 and CDR-L3 and with the amino acid sequences of said CDRs comprising the sequences of either:
   A. CDR-H1 GYTFTDYE (SEQ ID NO: 11)
      CDR-H2 IDPETGDT (SEQ ID NO: 12)
      CDR-H3 TSPIYYDYDWFAY (SEQ ID NO: 13)
      CDR-L1 QSLLNNRTRKNY (SEQ ID NO: 14)
      CDR-L2 WAS (SEQ ID NO: 15) and
      DR-L3 KQSYNLRT (SEQ ID NO: 16); or
   B. CDR-H1 GFSLSTSGMG (SEQ ID NO: 21)
      CDR-H2 IWWDDDK (SEQ ID NO: 22)
      CDR-H3 ARSITTVVATPFDY (SEQ ID NO: 23)
      CDR-L1 QNVRSA (SEQ ID NO: 24)
      CDR-L2 LAS (SEQ ID NO: 25) and
      CDR-L3 LQHWNSPFT (SEQ ID NO: 26).

2. The isolated antibody or antigen-binding fragment thereof of claim 1, wherein the heavy chain variable region of the antibody A according to claim 1 comprises the amino acid sequence of SEQ ID NO: 18 and the light chain variable region of the antibody A according to claim 1 comprises the amino acid sequence of SEQ ID NO: 20.

3. The isolated antibody or antigen-binding fragment thereof of claim 1, wherein the heavy chain variable region of the antibody B according to claim 1 comprises the amino acid sequence of SEQ ID NO: 28 and the light chain variable region of the antibody B according to claim 1 comprises the amino acid sequence of SEQ ID NO:30.

4. The antibody or antigen-binding fragment thereof of claim 1, wherein the light chain variable region and the heavy chain variable region of the antibody A or B according to claim 1 are fused.

5. The antibody or antigen-binding fragment thereof of claim 1, wherein the antibody is monoclonal or humanized.

6. The antibody or antigen-binding fragment thereof of claim 1, wherein the antigen-binding fragment is a Fab, Fab', F(ab')2, scFv, dsFv, ds-scFv, nanobody, minibody, diabody of the antibody according to claim 1 or a dimer or multimer thereof.

7. An immunoconjugate comprising the antibody or antigen-binding fragment thereof of claim 1 and a detectable label or cytotoxic agent.

8. The immunoconjugate of claim 7, wherein the detectable label comprises a positron emitting radionuclide.

9. A composition comprising the antibody or antigen-binding fragment thereof of claim 1, or the immunoconjugate of claim 7, optionally with a diluent.

* * * * *

SEQUENCE LISTING

<160> NUMBER OF SEQ ID NOS: 31

<210> SEQ ID NO 1
<211> LENGTH: 4
<212> TYPE: PRT
<213> ORGANISM: Homo sapiens

<400> SEQUENCE: 1

Gln Lys Leu Val
1

```
<210> SEQ ID NO 2
<211> LENGTH: 5
<212> TYPE: PRT
<213> ORGANISM: Homo sapiens

<400> SEQUENCE: 2

His Gln Lys Leu Val
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic Construct

<400> SEQUENCE: 3

Cys Gly Gln Lys Leu Val Gly
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic Construct

<400> SEQUENCE: 4

Gly Gln Lys Leu Val
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic Construct

<400> SEQUENCE: 5

Gly Gln Lys Leu Val Gly
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic Construct

<400> SEQUENCE: 6

Gly Gly Gln Lys Leu Val Gly
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic Construct

<400> SEQUENCE: 7

Gly Gln Lys Leu Val Gly Gly
1               5

<210> SEQ ID NO 8
<211> LENGTH: 8
<212> TYPE: PRT
```

<213> ORGANISM: Artificial Sequence
<220> FEATURE:
<223> OTHER INFORMATION: Synthetic Construct

<400> SEQUENCE: 8

Cys Gly Gln Lys Leu Val Gly Cys
1               5

<210> SEQ ID NO 9
<211> LENGTH: 6
<212> TYPE: PRT
<213> ORGANISM: Homo sapiens

<400> SEQUENCE: 9

His Gln Lys Leu Val Phe
1               5

<210> SEQ ID NO 10
<211> LENGTH: 5
<212> TYPE: PRT
<213> ORGANISM: Homo sapiens

<400> SEQUENCE: 10

Gln Lys Leu Val Phe
1               5

<210> SEQ ID NO 11
<211> LENGTH: 8
<212> TYPE: PRT
<213> ORGANISM: Mus musculus

<400> SEQUENCE: 11

Gly Tyr Thr Phe Thr Asp Tyr Glu
1               5

<210> SEQ ID NO 12
<211> LENGTH: 8
<212> TYPE: PRT
<213> ORGANISM: Mus musculus

<400> SEQUENCE: 12

Ile Asp Pro Glu Thr Gly Asp Thr
1               5

<210> SEQ ID NO 13
<211> LENGTH: 13
<212> TYPE: PRT
<213> ORGANISM: Mus musculus

<400> SEQUENCE: 13

Thr Ser Pro Ile Tyr Tyr Asp Tyr Asp Trp Phe Ala Tyr
1               5                   10

<210> SEQ ID NO 14
<211> LENGTH: 12
<212> TYPE: PRT
<213> ORGANISM: Mus musculus

<400> SEQUENCE: 14

Gln Ser Leu Leu Asn Asn Arg Thr Arg Lys Asn Tyr
1               5                   10

<210> SEQ ID NO 15
<211> LENGTH: 3
<212> TYPE: PRT

<213> ORGANISM: Mus musculus

<400> SEQUENCE: 15

Trp Ala Ser
1

<210> SEQ ID NO 16
<211> LENGTH: 8
<212> TYPE: PRT
<213> ORGANISM: Mus musculus

<400> SEQUENCE: 16

Lys Gln Ser Tyr Asn Leu Arg Thr
1               5

<210> SEQ ID NO 17
<211> LENGTH: 438
<212> TYPE: DNA
<213> ORGANISM: Mus musculus

<400> SEQUENCE: 17

```
atggaatgga gctgggtctt tctcttcctc ctgtcagtaa ttgcaggtgt ccaatcccag    60
gttcaactgc agcagtctgg ggctgagctg gtgaggcctg ggcttcagt gacgctgtcc   120
tgcaaggctt cgggctacac atttactgac tatgaaatgc actgggtgaa gcagacacct   180
gtgcatggcc tggaatggat tggagctatt gatcctgaaa ctggtgatac tgcctacaat   240
caggagttca gggcaaggc cacactgact gcagacaaat cctccagcac agcctacatg   300
gagctccgca gcctgacatc tgaggactct gccgtctatt actgtacaag ccccatctac   360
tatgattacg actggtttgc ttactggggc cacgggactc tggtcactgt ctctgcagct   420
acaacaacag ccccatct                                                  438
```

<210> SEQ ID NO 18
<211> LENGTH: 146
<212> TYPE: PRT
<213> ORGANISM: Mus musculus

<400> SEQUENCE: 18

Met Glu Trp Ser Trp Val Phe Leu Phe Leu Leu Ser Val Ile Ala Gly
1               5                   10                  15

Val Gln Ser Gln Val Gln Leu Gln Gln Ser Gly Ala Glu Leu Val Arg
            20                  25                  30

Pro Gly Ala Ser Val Thr Leu Ser Cys Lys Ala Ser Gly Tyr Thr Phe
        35                  40                  45

Thr Asp Tyr Glu Met His Trp Val Lys Gln Thr Pro Val His Gly Leu
    50                  55                  60

Glu Trp Ile Gly Ala Ile Asp Pro Glu Thr Gly Asp Thr Ala Tyr Asn
65                  70                  75                  80

Gln Glu Phe Lys Gly Lys Ala Thr Leu Thr Ala Asp Lys Ser Ser Ser
                85                  90                  95

Thr Ala Tyr Met Glu Leu Arg Ser Leu Thr Ser Glu Asp Ser Ala Val
            100                 105                 110

Tyr Tyr Cys Thr Ser Pro Ile Tyr Tyr Asp Tyr Asp Trp Phe Ala Tyr
        115                 120                 125

Trp Gly His Gly Thr Leu Val Thr Val Ser Ala Ala Thr Thr Thr Ala
    130                 135                 140

Pro Ser
145

<210> SEQ ID NO 19
<211> LENGTH: 438
<212> TYPE: DNA
<213> ORGANISM: Mus musculus

<400> SEQUENCE: 19

| | | | | | |
|---|---|---|---|---|---|
| atggaatgga | gctgggtctt | tctcttcctc | ctgtcagtaa | ttgcaggtgt | ccaatcccag | 60 |
| gttcaactgc | agcagtctgg | ggctgagctg | gtgaggcctg | gggcttcagt | gacgctgtcc | 120 |
| tgcaaggctt | cgggctacac | atttactgac | tatgaaatgc | actgggtgaa | gcagacacct | 180 |
| gtgcatggcc | tggaatggat | tggagctatt | gatcctgaaa | ctggtgatac | tgcctacaat | 240 |
| caggagttca | agggcaaggc | cacactgact | gcagacaaat | cctccagcac | agcctacatg | 300 |
| gagctccgca | gcctgacatc | tgaggactct | gccgtctatt | actgtacaag | ccccatctac | 360 |
| tatgattacg | actggtttgc | ttactggggc | cacgggactc | tggtcactgt | ctctgcagct | 420 |
| acaacaacag | ccccatct | | | | | 438 |

<210> SEQ ID NO 20
<211> LENGTH: 136
<212> TYPE: PRT
<213> ORGANISM: Mus musculus

<400> SEQUENCE: 20

Met Asp Ser Gln Ala Gln Val Leu Ile Leu Leu Leu Leu Trp Val Ser
1               5                   10                  15

Gly Thr Cys Gly Asp Ile Val Met Ser Gln Ser Pro Ser Ser Leu Ala
            20                  25                  30

Val Ser Ala Gly Glu Lys Val Thr Met Ser Cys Lys Ser Ser Gln Ser
        35                  40                  45

Leu Leu Asn Asn Arg Thr Arg Lys Asn Tyr Leu Ala Trp Tyr Gln Gln
    50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Gln Ala Glu Asp Leu Ala Val Tyr
            100                 105                 110

Tyr Cys Lys Gln Ser Tyr Asn Leu Arg Thr Phe Gly Gly Gly Thr Lys
        115                 120                 125

Leu Glu Ile Lys Arg Ala Asp Ala
    130                 135

<210> SEQ ID NO 21
<211> LENGTH: 10
<212> TYPE: PRT
<213> ORGANISM: Mus musculus

<400> SEQUENCE: 21

Gly Phe Ser Leu Ser Thr Ser Gly Met Gly
1               5                   10

<210> SEQ ID NO 22
<211> LENGTH: 7
<212> TYPE: PRT
<213> ORGANISM: Mus musculus

<400> SEQUENCE: 22

```
Ile Trp Trp Asp Asp Asp Lys
1               5

<210> SEQ ID NO 23
<211> LENGTH: 14
<212> TYPE: PRT
<213> ORGANISM: Mus musculus

<400> SEQUENCE: 23

Ala Arg Ser Ile Thr Thr Val Val Ala Thr Pro Phe Asp Tyr
1               5                   10

<210> SEQ ID NO 24
<211> LENGTH: 6
<212> TYPE: PRT
<213> ORGANISM: Mus musculus

<400> SEQUENCE: 24

Gln Asn Val Arg Ser Ala
1               5

<210> SEQ ID NO 25
<211> LENGTH: 3
<212> TYPE: PRT
<213> ORGANISM: Mus musculus

<400> SEQUENCE: 25

Leu Ala Ser
1

<210> SEQ ID NO 26
<211> LENGTH: 9
<212> TYPE: PRT
<213> ORGANISM: Mus musculus

<400> SEQUENCE: 26

Leu Gln His Trp Asn Ser Pro Phe Thr
1               5

<210> SEQ ID NO 27
<211> LENGTH: 436
<212> TYPE: DNA
<213> ORGANISM: Mus musculus

<400> SEQUENCE: 27
atggacaggc ttacttcttc attcctgctg ctgattgtcc ctgcatatgt cttgtcccaa      60
gttactctaa aagagtctgg ccctgggata ttgaagccct cacagaccct cagtctgact     120
tgttctttct ctgggttttc actgagcact tctggtatgg gtgtaggctg gattcgtcag     180
ccttcaggga agggtctgga gtggctggca cacatttggt gggatgatga taagtactat     240
aacccatccc tgaagagcca gctcacaatc tccaaggata cctccagaaa ccaggtattc     300
ctcaagatca ccagtgtgga cactgcagat actgccactt actactgtgc tcgaagtatt     360
actacggtag tagctacgcc ctttgactac tggggccaag caccactctc acagtctcc     420 tcagccaaaa cgacac                                                      436

<210> SEQ ID NO 28
<211> LENGTH: 145
<212> TYPE: PRT
<213> ORGANISM: Mus musculus

<400> SEQUENCE: 28
```

Met Asp Arg Leu Thr Ser Ser Phe Leu Leu Ile Val Pro Ala Tyr
1               5                   10                  15

Val Leu Ser Gln Val Thr Leu Lys Glu Ser Gly Pro Gly Ile Leu Lys
            20                  25                  30

Pro Ser Gln Thr Leu Ser Leu Thr Cys Ser Phe Ser Gly Phe Ser Leu
            35                  40                  45

Ser Thr Ser Gly Met Gly Val Gly Trp Ile Arg Gln Pro Ser Gly Lys
    50                  55                  60

Gly Leu Glu Trp Leu Ala His Ile Trp Trp Asp Asp Lys Tyr Tyr
65                  70                  75                  80

Asn Pro Ser Leu Lys Ser Gln Leu Thr Ile Ser Lys Asp Thr Ser Arg
                85                  90                  95

Asn Gln Val Phe Leu Lys Ile Thr Ser Val Asp Thr Ala Asp Thr Ala
            100                 105                 110

Thr Tyr Tyr Cys Ala Arg Ser Ile Thr Thr Val Val Ala Thr Pro Phe
            115                 120                 125

Asp Tyr Trp Gly Gln Gly Thr Thr Leu Thr Val Ser Ser Ala Lys Thr
            130                 135                 140

Thr
145

<210> SEQ ID NO 29
<211> LENGTH: 405
<212> TYPE: DNA
<213> ORGANISM: Mus musculus

<400> SEQUENCE: 29
atgggcatca agatggagtt tcagacccag gtctttgtat tcgtgttgct ctggttgtct      60
ggtgttgatg gagacattgt gatgacccag tctcaaaaat tcatgtccac atcagtagga    120
gacagggtca gcatcacctg caaggccagt cagaatgttc gttctgctgt agcctggtat    180
caacagaaac cagggcagtc tcctaaagca ctgatttacc tggcatccaa ccggcacact    240
ggagtccctg atcgcttcac aggcagtgga tctgggacag atttcactct caccattagc    300
aatgtgcatt ctgaagacct gacagattat ttctgtctgc aacattggaa ttctccgttc    360
acgttcggag gggggaccaa gctggaaata aaacgggctg atgct                    405

<210> SEQ ID NO 30
<211> LENGTH: 135
<212> TYPE: PRT
<213> ORGANISM: Mus musculus

<400> SEQUENCE: 30

Met Gly Ile Lys Met Glu Phe Gln Thr Gln Val Phe Val Phe Val Leu
1               5                   10                  15

Leu Trp Leu Ser Gly Val Asp Gly Asp Ile Val Met Thr Gln Ser Gln
            20                  25                  30

Lys Phe Met Ser Thr Ser Val Gly Asp Arg Val Ser Ile Thr Cys Lys
            35                  40                  45

Ala Ser Gln Asn Val Arg Ser Ala Val Ala Trp Tyr Gln Gln Lys Pro
    50                  55                  60

Gly Gln Ser Pro Lys Ala Leu Ile Tyr Leu Ala Ser Asn Arg His Thr
65                  70                  75                  80

Gly Val Pro Asp Arg Phe Thr Gly Ser Gly Ser Gly Thr Asp Phe Thr
            85                  90                  95

Leu Thr Ile Ser Asn Val His Ser Glu Asp Leu Thr Asp Tyr Phe Cys

```
                100                 105                 110
Leu Gln His Trp Asn Ser Pro Phe Thr Phe Gly Gly Gly Thr Lys Leu
            115                 120                 125

Glu Ile Lys Arg Ala Asp Ala
    130             135

<210> SEQ ID NO 31
<211> LENGTH: 42
<212> TYPE: PRT
<213> ORGANISM: Homo sapiens

<400> SEQUENCE: 31

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
            35                  40
```

UNITED STATES PATENT AND TRADEMARK OFFICE
CERTIFICATE OF CORRECTION

PATENT NO. : 10,759,837 B2 Page 1 of 1
APPLICATION NO. : 15/774778
DATED : September 1, 2020
INVENTOR(S) : Neil R. Cashman and Steven S. Plotkin It is certified that error appears in the above-identified patent and that said Letters Patent is hereby corrected as shown below:

In the Claims

Claim 1, Column 75, Line 42, delete "DR-L3" and insert --CDR-L3--.

Signed and Sealed this
Twenty-third Day of March, 2021

Drew Hirshfeld
*Performing the Functions and Duties of the*
*Under Secretary of Commerce for Intellectual Property and*
*Director of the United States Patent and Trademark Office*